: USOO5082539A

United States Patent [19]
Saji et al.

[11] Patent Number: 5,082,539
[45] Date of Patent: Jan. 21, 1992

[54] FERROCENE COMPOUNDS AND USES THEREOF

[75] Inventors: Tetsuo Saji; Katsuyoshi Hoshino, both of Tokyo, Japan

[73] Assignee: Idemitsu Kosan Company Limited, Tokyo, Japan

[21] Appl. No.: 469,299

[22] Filed: Jan. 24, 1990

Related U.S. Application Data

[63] Continuation-in-part of Ser. No. 265,678, Oct. 27, 1988, abandoned, and a continuation-in-part of Ser. No. 340,006, Apr. 6, 1989, abandoned.

[30] Foreign Application Priority Data

| Mar. 31, 1987 | [JP] | Japan | 62-075930 |
| Aug. 28, 1987 | [JP] | Japan | 62-212718 |
| Mar. 2, 1988 | [JP] | Japan | 63-047501 |
| Mar. 8, 1988 | [JP] | Japan | 63-052696 |
| Mar. 30, 1988 | [WO] | PCT Int'l Appl. | PCT/JP/00323 |
| Aug. 27, 1988 | [WO] | PCT Int'l Appl. | PCT/JP88/00855 |

[51] Int. Cl.$^5$ ............................ C25D 3/02; C25B 3/12
[52] U.S. Cl. ............................ 205/162; 204/59 QM; 204/72; 204/180.2; 556/143; 556/144; 252/352; 252/356; 252/357; 205/317
[58] Field of Search .............. 204/56.1, 590 H, 180.2, 204/181.4, 181.6, 181.7, 59 R, 72; 556/143, 144, 145; 252/351, 352, 357, 356

[56] References Cited

U.S. PATENT DOCUMENTS

| 4,132,608 | 1/1979 | Chandross et al. | 204/56.1 |
| 4,650,658 | 3/1987 | Frank | 204/DIG. 3 |
| 4,749,670 | 6/1988 | Simon et al. | 502/53 |

FOREIGN PATENT DOCUMENTS 234274   3/1986  German Democratic Rep. .
63-243290 11/1988  Japan .

OTHER PUBLICATIONS

Chemical Abstracts, vol. 92, No. 21, May 26, 1980.
Seiders, Reginald P. et al., 181326d, Israel J. Chem., 1979.
Journal of the Chemical Society, Chemical Communication, No. 13, Jul. 1, 1985, Saji, Tetsuo et al., pp. 865-866.
J. Am. Chem. Soc., vol. 109, No. 19, 1987, Hoshino, Katsuyoshi et al., pp. 5881-5883.
Chemistry Letters, No. 7, 1987, pp. 1439-1442.

Primary Examiner—John F. Niebling
Assistant Examiner—Kathryn Gorgos
Attorney, Agent, or Firm—Frishauf, Holtz, Goodman & Woodward

[57] ABSTRACT

Novel ferrocene derivatives represented by the general formula:

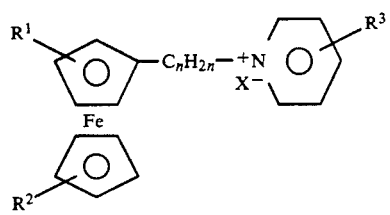

or the general formula:

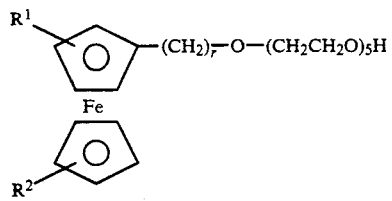

or the general formula:

(Abstract continued on next page.)

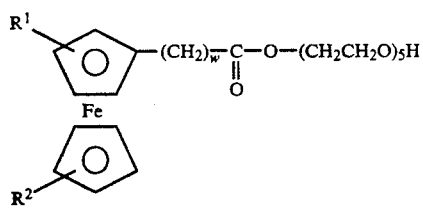
(wherein all the symbols are as described in the specification) are excellent as surfactants.
By application of an electrochemical method using the novel ferrocene derivatives or other ferrocene derivatives as a micelle forming agent (surfactant), an organic thin film of a hydrophobic organic substance can be efficiently produced.
62 Claims, 34 Drawing Sheets

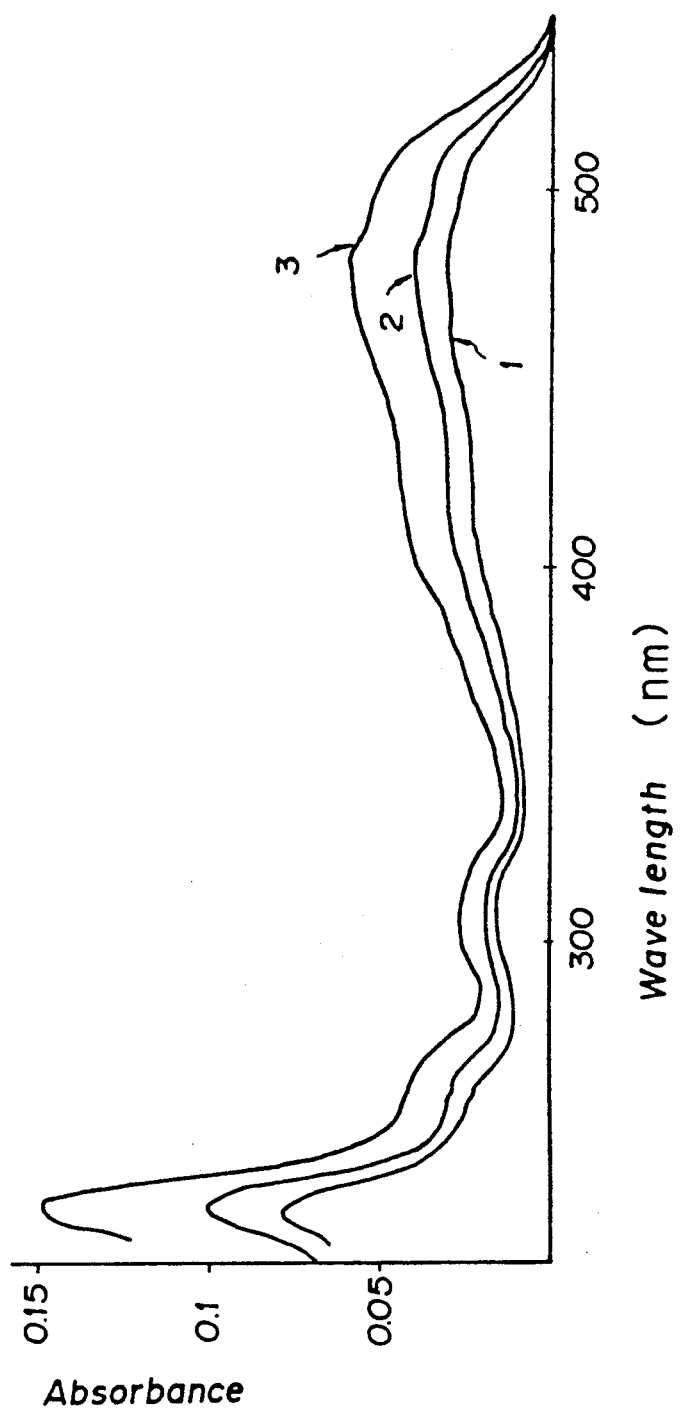

F I G. 12
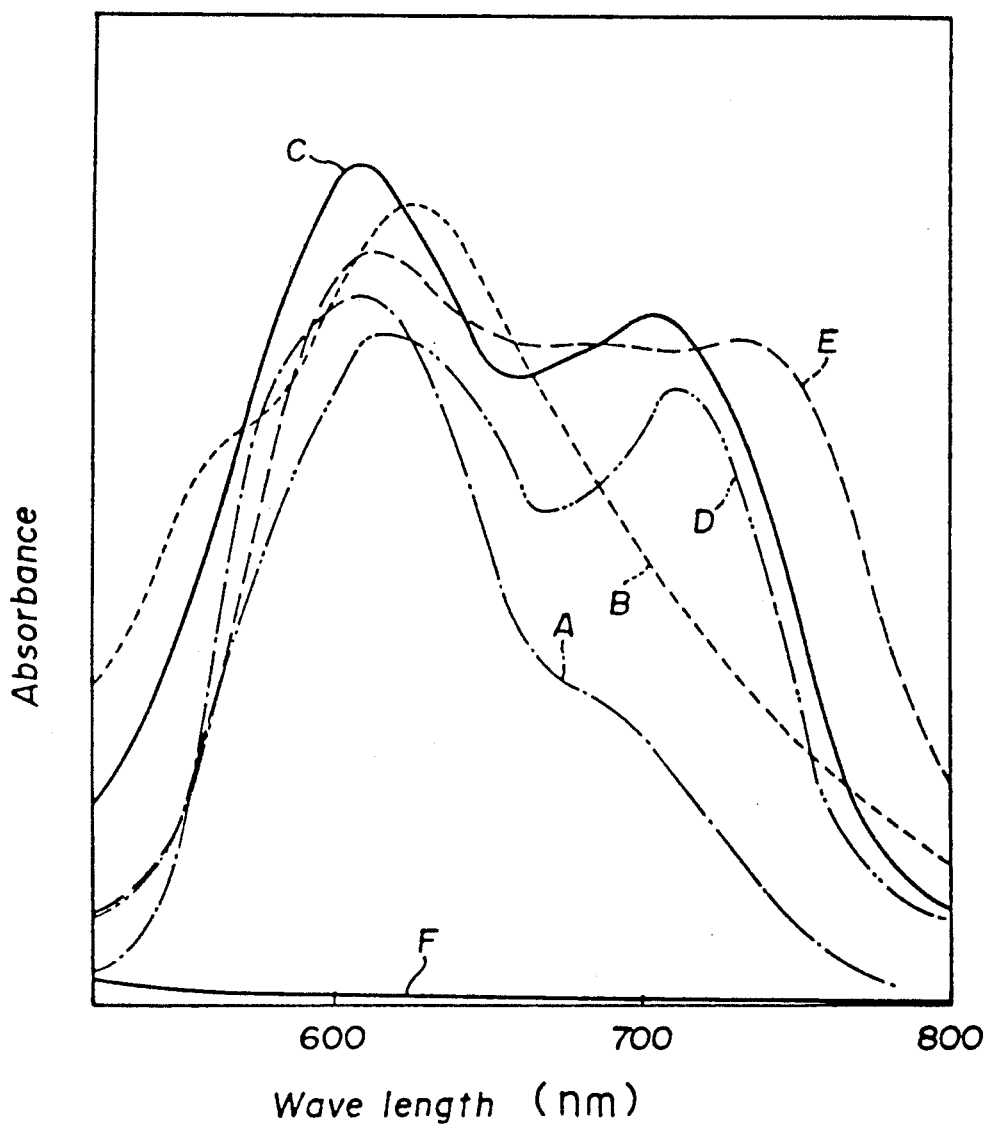

F I G.13
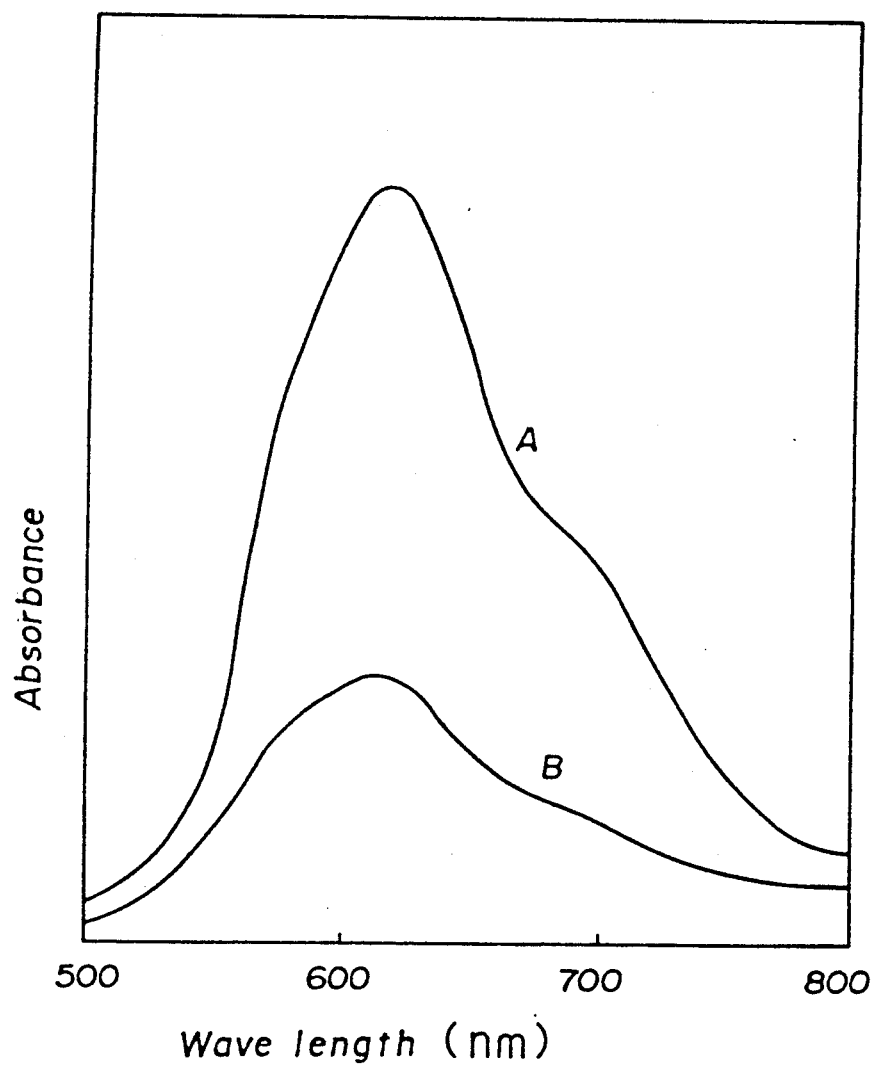

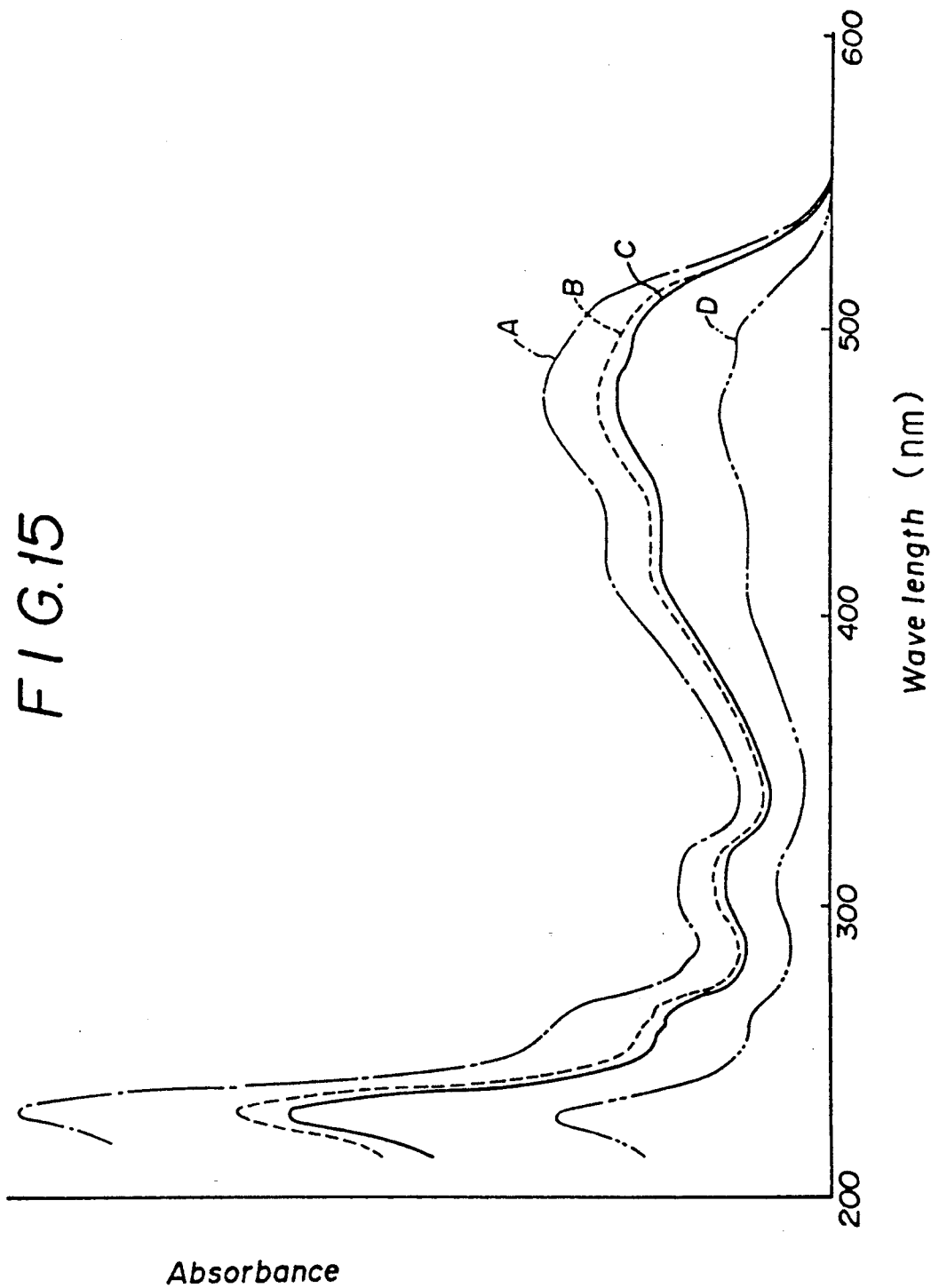

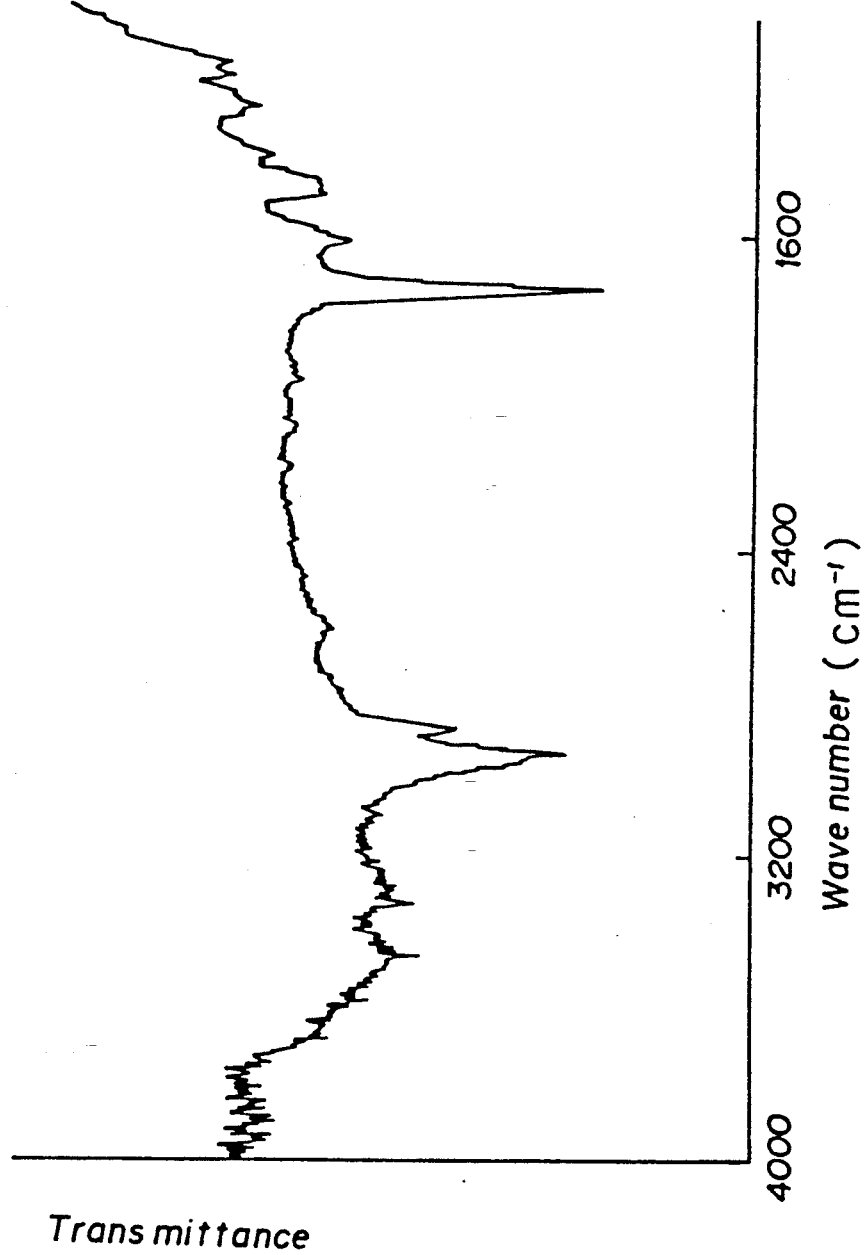

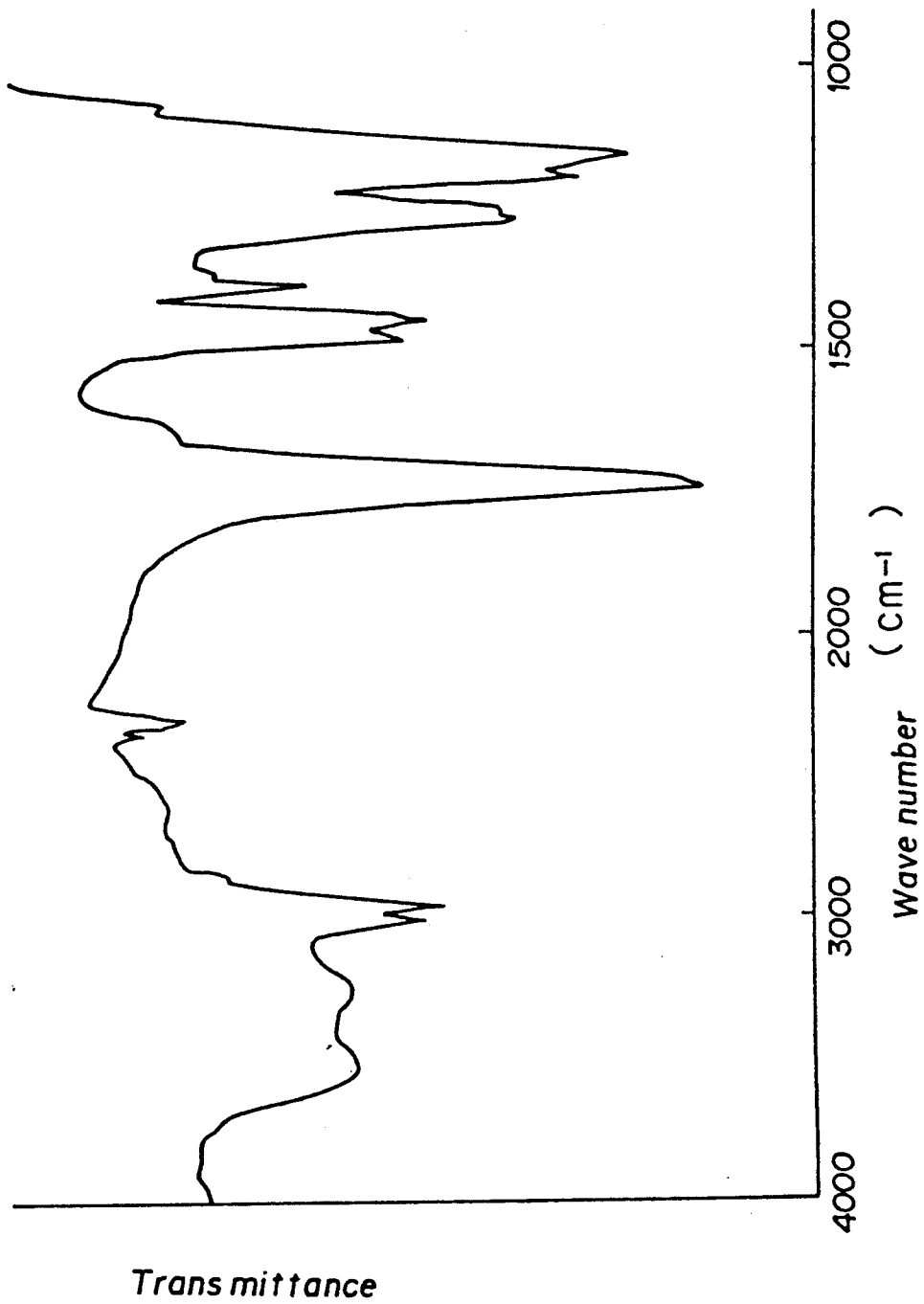

FERROCENE COMPOUNDS AND USES THEREOF

This application is a continuation-in-part application of Ser. No. 07/265,678 filed Oct. 27, 1988 now abandoned and of Ser. No. 07/340,006 filed Apr. 6, 1989 now abandoned.

TECHNICAL FIELD

The present invention relates to ferrocene derivatives and a process for producing organic thin films, and more particularly to novel ferrocene derivatives, surfactants and solutions containing them and capable of making coloring matter, e.g., phthalocyanine, soluble, and a process for producing organic thin films using various ferrocene derivatives including said novel ferrocene derivatives.

BACKGROUND ART

In general, coloring matters such as phthalocyanine or its derivatives and the like are insoluble in water, and although they are soluble in organic solvents such as dimethylformamide (DMF), tetrahydrofuran (THF) and the like, their soluble amounts are small and the solubility is only several milligrams (mg).

Surfactants to make the phthalocyanine and the like soluble in water have heretofore been investigated, but no satisfactory surfactant has been developed. It is reported that functional group-substituted phthalocyanine derivatives can be dissolved in water to some extent by the use of sulfone-based surfactants. However, the solubility is not always sufficiently high and further unsubstituted phthalocyanine cannot be dissolved at all.

In connection with polymers insoluble in water, surfactants to make them soluble in water have been investigated in the same manner as described above. In fact, however, no satisfactory results have been obtained.

The present inventors have made extensive investigations to develop surfactants to make coloring matters such as phthalocyanine or its derivatives and the like, or water-insoluble polymers and the like, soluble in water.

In the course of study, it has been found that ferrocene derivatives are promising as surfactants having the aforementioned performance. As a result of further investigations based on the above findings, the present inventors have discovered that new ferrocene derivatives derived by introducing a specified substituent containing a polyoxyethylene chain or pyridinium ion, in ferrocene or its derivatives can achieve the object. At the same time, they have discovered that a water-insoluble (hydrophobic) organic thin film can be efficiently produced from various ferrocene derivatives including the new ferrocene derivatives by electrochemical techniques.

An object of the present invention is to provide novel ferrocene derivatives. Another object of the present invention is to provide surfactants having superior performance, containing the novel ferrocene derivatives. Another object of the present invention is to provide a process for efficiently producing thin films of hydrophobic organic substances.

SUMMARY OF THE INVENTION

That is, the present invention provides ferrocene derivatives represented by the general formula:

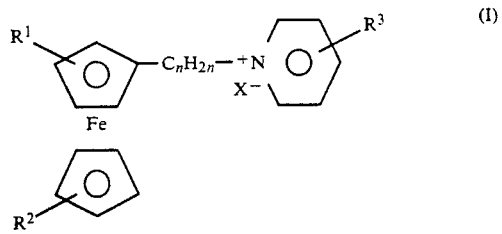

(wherein $R^1$ and $R^2$ are each independently a hydrogen, a methyl group, an ethyl group, a methoxy group or a carbomethoxy group, $R^3$ is hydrogen, a methyl group, an ethyl group, a methoxy group, a carbomethoxy group, a hydroxyl group, a carboxyl group or a sulfonic acid group, and X is a halogen, and $C_nH_{2n}$ is a straight chain or branched chain hydrocarbon group having 4 to 16 carbon atoms), the general formula:

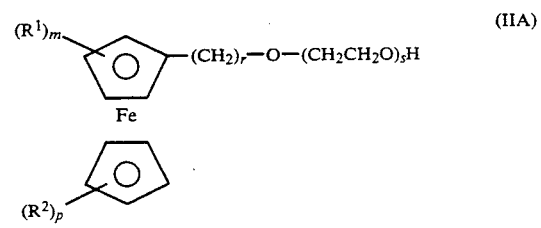

(wherein m is an integer of 1 to 4, p is an integer of 1 to 5, r is an integer of 11 to 18, s is a real number of 2.0 to 70, preferably 2 to 50, and $R^1$ and $R^2$ are the same as described above), or the general formula:

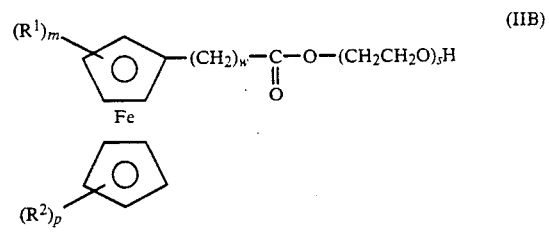

(wherein w is an integer of 2 to 20, and m, p, s, $R^1$ and $R^2$ are the same as described above).

The present invention further provides surfactants containing the ferrocene derivatives represented by the above general formula (I), (IIA), or (IIB).

The present invention further provides a process for producing organic thin films which comprises making hydrophobic organic substances soluble in an aqueous medium by the use of surfactants (micelle forming agents) comprising ferrocene derivatives represented by the general formula (I), (IIA) or (IIB), or ferrocene derivatives represented by the general formula (IIA'):

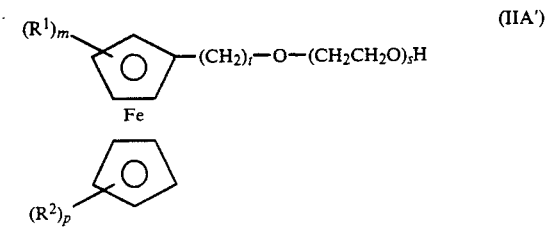

(wherein t is an integer of 2 to 10, and $R^1$, $R^2$, m, p and s are the same as above), and electrolyzing the resulting micelle solution thus obtained to form a thin film of the above hydrophobic organic substance on an electrode.

The novel ferrocene derivatives of the present invention are the novel compounds represented by the general formula (I), (IIA) or (IIB). In accordance with the process of the present invention, using these novel ferrocene derivatives or other ferrocene derivatives as surfactants, thin films of hydrophobic organic substances can be formed efficiently and further in the desired thickness.

BRIEF DESCRIPTION OF DRAWINGS

FIG. 7 indicates ultraviolet (UV) absorption spectra of the ethanol solutions of the thin films formed in Examples 3 and 4.

FIG. 12 indicates visible (VIS) absorption spectra of the supernatants obtained in Examples 8 to 12.

FIG. 13 indicates visible absorption spectra of the coloring matter thin films on ITO as obtained in Examples 13 and 14.

FIG. 15 indicates UV absorption spectra of the ethanol solutions of the thin films formed in Examples 4, 15 and 16.

FIG. 20 is a Fourier transformation infrared absorption spectrum of the thin film formed in Example 20.

FIG. 21 is a IR absorption spectrum using a KBr pellet of the polymer used in Example 20.

DETAILED DESCRIPTION OF THE INVENTION

Figure 1:
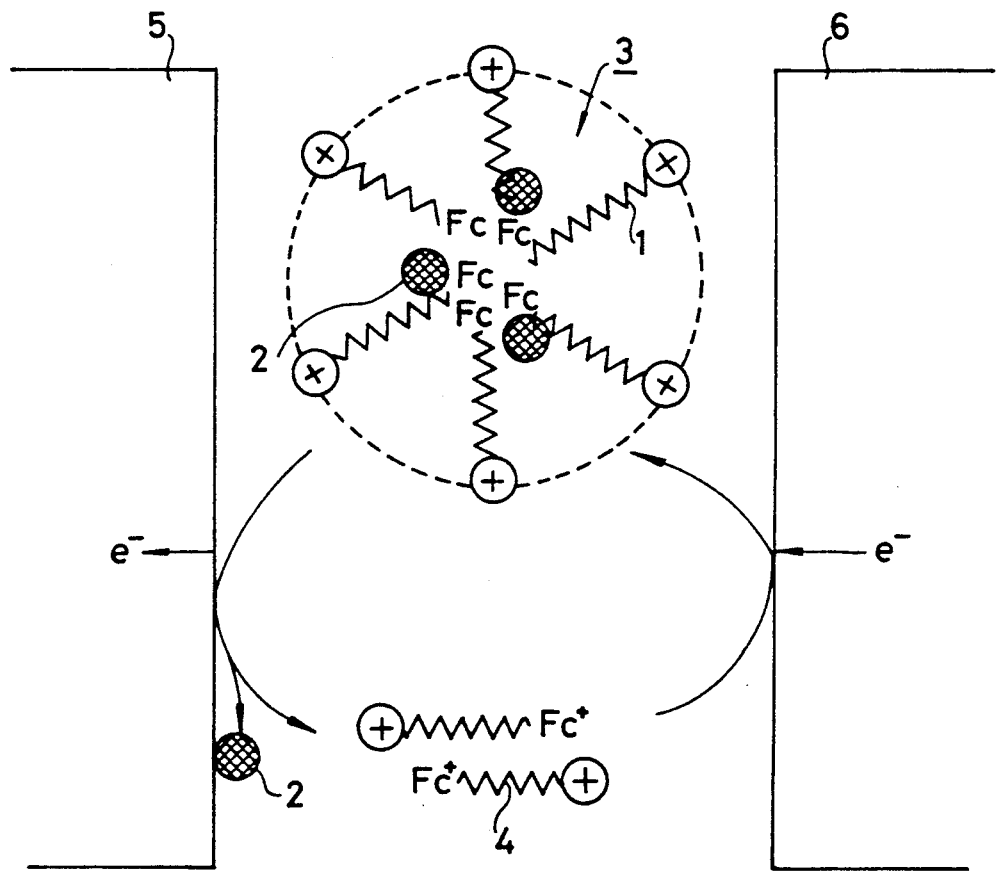
FIG. 1 is a view schematically illustrating the principle of the process of the present invention, wherein 1 indicates a ferrocene derivative; 2, a hydrophobic organic substance; 3, micelle; 4, an oxidized ferrocene derivative; 5, an anode; 6, a cathode; Fc, ferrocene; and $e^-$, an electron.

The novel ferrocene derivatives of the present invention are represented by the general formula (I), (IIA) or (IIB). In the general formula (I), $R^1$ and $R^2$ are each independently a hydrogen, a methyl group, an ethyl group, a methoxy group or a carbomethoxy group, $R^3$ is a hydrogen, a methyl group, an ethyl group, a methoxy group, a carbomethoxy group, a hydroxyl group, a carboxyl group or a sulfonic acid group, and X is a halogen, that is, chlorine, bromine, iodine, fluorine and the like. The formula $C_nH_{2n}$ indicates a straight or branched hydrocarbon group having 4 to 16 carbon atoms (that is, n is an integer of 4 to 16). Specific examples are straight hydrocarbon groups exemplified by polymethylene groups: $(CH_2)_n$, such as a tetramethylene group, a pentamethylene group, an octamethylene group, an undecamethylene group, a dodecamethylene group, a hexadecamethylene group and the like, or branched hydrocarbon groups such as a 2-methylundecamethylene group, a 4-ethylundecamethylene group and the like.

The ferrocene derivatives represented by the general formula (I) can be produced by various methods. For example, they can be produced by adding pyridine-based compounds represented by the general formula:

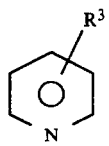
(I-b)

(wherein $R^3$ is the same as described above) to halogen-containing ferrocene derivatives represented by the general formula:

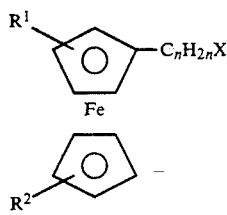
(I-a)

(wherein $R^1$, $R^2$, X and $C_nH_{2n}$ are the same as described above) and reacting them for about 1 to 5 hours in an atmosphere of inert gas such as nitrogen gas and the like at a temperature of 20° to 70° C. while sufficiently stirring. Thereafter, the product is washed with diethyl ether and the like and dried, and then dissolved in a polar solvent such as acetone, methanol, ethanol, tetrahydrofuran and the like. The resulting solution is poured in diethyl ether and the like to precipitate. This operation is repeated several times, and upon filtration, the ferrocene derivatives of the general formula (I) can be obtained in a high purity.

On the other hand, in the ferrocene derivatives represented by the general formula (IIA), m is an integer of 1 to 4, p is an integer of 1 to 5, r is an integer of 11 to 18, and s is a real number of 2.0 to 70, preferably 2 to 50. Since r is an integer of 11 to 18 as described above, hydrocarbon group (polymethylene group) having 11 to 18 carbon atoms, such as an undecamethylene group, a dodecamethylene group, a tridecamethylene group and the like, is present between a ring-forming carbon atom and an oxygen atom (oxygen atom nearest the ferrocene structure). The symbol s means not only an integer between 2.0 to 70 but also a real number including them, and indicates an average repeating number of the oxyethylene group ($-CH_2CH_2O-$) constituting the ferrocene derivative.

On the other hand, since w of the general formula (IIB) indicates an integer of 2 to 20, an alkylene group (polymethylene group) having 2 to 20 carbon atoms, e.g., an ethylene group or a propylene group is present between a ring-constituting carbon atom and an oxycarbonyl group. $R^1$, $R^2$, m, p and s are the same as described above.

The ferrocene derivatives of the general formula (IIA) or (IIB) can be produced by various methods. For example, the ferrocene derivatives represented by the general formula (IIA) are obtained by adding an alkali metal (metallic sodium, metallic potassium and the like) to polyethylene glycol represented by the general formula:

$$HO-CH_2CH_2O)_sH \qquad (II\text{-}a)$$

(wherein s is the same as described above), stirring the resulting mixture for several minutes to several days at a temperature of ordinary temperature to 200° C., adding a hydrogen-containing ferrocene compound represented by the general formula:

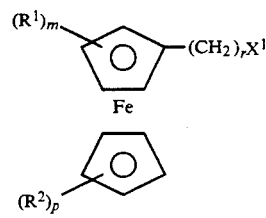
(II-b)

(wherein $R^1$, $R^2$, m, p and r are the same as described above, and $X^1$ is a halogen atom), and reacting them with stirring, and then extracting and purifying.

Thereafter, upon extraction and purification, a ferrocene derivative represented by the general formula (IIA) is obtained.

A halogen-containing ferrocene compound of the general formula (II-b) can be prepared, for example, by converting ω-halogenocarboxylic acid represented by the general formula: $HOOC(CH_2)_{r-1}X^1$ (wherein r and $X^1$ are the same as described above) into acid halide (acylated product) represented by the general formula: $X^2OC(CH_2)_{r-1}X^1$ (wherein $X^2$ is a halogen atom resulting from a halogenating agent, and r and $X^1$ are the same as described above) by the use of a suitable halogenating agent (thionyl chloride, etc.), reacting the acid halide with ferrocene or its derivative represented by the general formula:

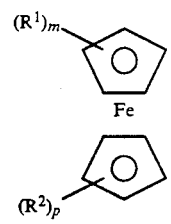
(III)

(wherein $R^1$, $R^2$, m and p are the same as described above) to obtain a ferrocenylketone derivative represented by the general formula:

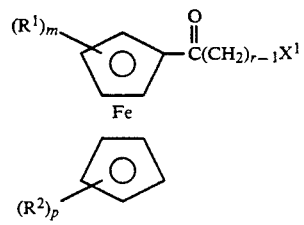
(VII)

(wherein $R^1$, $R^2$, m, p and r are the same as described above), and further reducing the ferrocenylketone derivative.

On the other hand, the ferrocene derivatives represented by the general formula (IIB) can be obtained by adding concentrated sulfuric acid to polyethylene glycol represented by the above general formula (II-a), stirring the resulting mixture for several minutes to several days at a temperature of ordinary temperature to 200° C., adding carboxyl group-containing ferrocene compounds represented by the general formula:

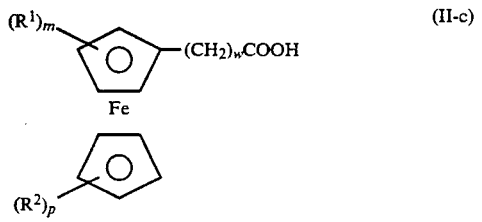

(II-c)

(wherein $R^1$, $R^2$, m, p and w are the same as described above), reacting with stirring, and then extracting and purifying. That is, in accordance with this method, the ferrocene derivatives represented by the general formula (IIB) are obtained.

A carboxyl group-containing ferrocene compound of the general formula (II-c) can be prepared, for example, as follows: that is, the carboxyl group-containing ferrocene compound represented by the general formula (II-c) can be prepared by reacting alkoxycarbonylic acid halide represented by the general formula: $X^3OC(CH_2)_{w-1}COOR$ (wherein $X^3$ is a halogen atom, R is an alkyl group, and w is the same as described above) with ferrocene or its derivative represented by the general formula (III) to obtain ferrocenoylcarboxylic acid ester represented by the general formula:

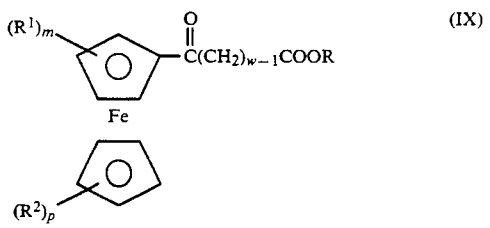

(IX)

(wherein $R^1$, $R^2$, m, p and w are the same as described above), then hydrolyzing to obtain the corresponding carboxylic acid, and then reducing or alternatively reducing and then hydrolyzing.

In producing the ferrocene derivatives represented by the general formulas (IIA) and (IIB), similar polyethers can be used respectively, in place of the polyethylene glycol of the general formula (II-a). It suffices that the extraction treatment after the reaction is carried out using alcohol, THF and the like, and the purification is carried out by chromatographic purification and the like.

The ferrocene derivatives of the present invention as represented by the general formula (I), (IIA) or (IIB) which are obtained by the methods as described above are effective as surfactants and can be used particularly as surfactants (micelle forming agents) to make hydrophobic organic substances soluble in water or an aqueous medium. In this case, ferrocene derivatives of the general formula (IIA) wherein m and p are 1, r is 11 to 15 and specifically 11 to 13, and s is 2 to 50 are preferred for use as surfactants. In the general formula (IIB), ferrocene derivatives in which m and p are 1, w is 7 to 15, and s is 2 to 50 are preferred for use as surfactants.

The surfactants of the present invention contain the ferrocene derivatives of the general formula (I), (IIA) or (IIB) as the major component, and other various additives can be added thereto, if necessary. When the surfactants of the present invention are used, various hydrophobic organic substances can be made soluble in water or in an aqueous medium.

A process for production of organic thin films of the present invention will hereinafter be explained. In the process of the present invention, the ferrocene derivatives are used as surfactants (micelle forming agents). As the ferrocene derivatives, not only the ferrocene derivatives of the above general formula (I), (IIA) or (IIB), but also various ferrocene derivatives can be used.

Examples of such ferrocene derivatives include, as well as those represented by the general formula (I), (IIA) or (IIB), ferrocene derivatives of the general formula (IIA') wherein m and p are 1, s is 2 to 50, t is 2 to 10, and ferrocene derivatives in which a ferrocene compound (ferrocene or ferrocene having a suitable substituent (an alkyl group, an acetyl group and the like)) is bonded to a cationic surfactant of the ammonium type (preferably the quaternary ammonium type) having a main chain having 4 to 16 carbon atoms (preferably 8 to 14). If the number of carbon atoms in the main chain is too small, no micelle is formed, and if it is too large, the resulting ferrocene derivatives are not soluble in water. The ferrocene compound is bonded to the surfactant in various embodiments. Main embodiments are an embodiment in which the ferrocene compound is bonded to the terminal of the main chain of the surfactant, an embodiment in which the ferrocene compound is bonded to an intermediate point of the main chain, directly or through an alkyl group, and an embodiment in which the ferrocene compound is incorporated in the main chain. Ferrocene derivatives of this type are represented by the general formula:

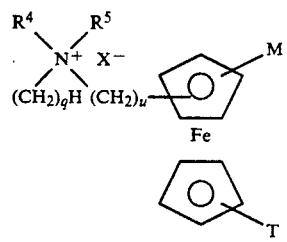

(wherein $R^4$ and $R^5$ are each a hydrogen or an alkyl group having 1 to 4 carbon atoms (but not exceeding q as described hereinafter), M and T are each a hydrogen or a substituent, X is a halogen, and t and u are integers satisfying the requirements: $q \geq 0$, $u \geq 0$, and $4 \leq q + u \leq 16$), the general formula:

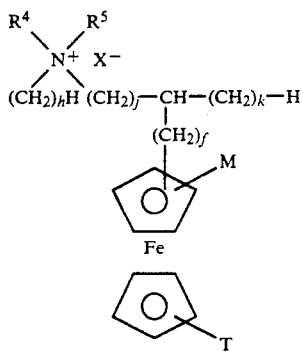

(wherein $R^4$, $R^5$, X, M and T are the same as described above, provided that the number of carbon atoms of $R^4$ and $R^5$ does not exceed h as described hereinafter), and f, h, j and k are integers satisfying the requirements: $h \geq 0$, $j \geq 0$, $k \geq 1$ $0 \leq f \leq k-1$ and $3 \leq h+j+k \leq 15$; the general formula:

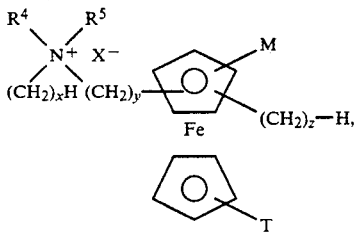

wherein $R^4$, $R^5$, X, M and T are the same as described above (provided that the number of carbon atoms of $R^4$ and $R^5$ does not exceed x as described hereinafter), and x, y and z are integers satisfying the requirements: $x \geq 0$, $y \geq 0$, $z \geq 1$, and $4 \leq x+y+z \leq 16$), or the general formula:

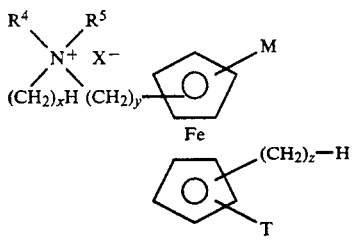

(wherein $R^4$, $R^5$, M, T, x, y and z are the same as described above).

In the process of the present invention, as ferrocene derivatives to be used as the micelle forming agent, those derived by replacing a part of the alkyl chain of the general surfactant (surface active agent) with ferrocene can be used.

Representative examples of ferrocene compounds as the micelle forming agent (surfactant) are shown below.

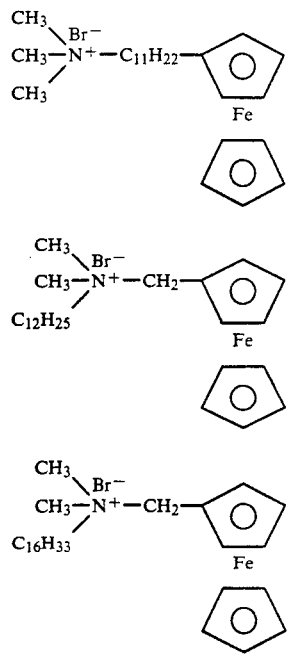

In the process of the present invention, a surfactant (micelle forming agent) comprising the aforementioned ferrocene derivatives, a supporting salt and a hydrophobic organic substance are introduced in an aqueous medium and thoroughly dispersed by the use of supersonic waves, a homogenizer, or a stirrer and the like to form a micelle and then, if necessary, an excess of the hydrophobic organic substance is removed and the micelle solution thus obtained is subjected to electrolytic treatment using the aforementioned electrode while allowing it to stand or somewhat stirring it. During the electrolytic treatment, the hydrophobic organic substance may be supplementarily added to the micelle solution, or there may be provided a recycle circuit in which the micelle solution in the vicinity of the anode is withdrawn out of the system, the hydrophobic organic substance is added to the withdrawn micelle solution and thoroughly stirred, and then the resulting solution is returned to the vicinity of the cathode. Electrolytic conditions are determined appropriately depending on various circumstances. Usually the liquid temperature is 0° to 70° C. and preferably 20° to 30° C., the voltage is 0.03 to 1.5 V and preferably 0.1 to 0.5 V, and the current density is not more than 10 mA/cm$^2$ and preferably 50 to 300 μA/cm$^2$.

On performing this electrolytic treatment, the reaction as illustrated in FIG. 1 proceeds. Explaining in connection with the behavior of Fe ion of the ferrocene derivative, $Fe^{2+}$ is converted into $Fe^{3+}$ on the anode 5, leading to break-down of the micelle, and particles (about 600 to 900 Å) of the hydrophobic organic substance are deposited on the anode. On the other hand, on the cathode 6, $Fe^{3+}$ oxidized on the anode 5 is reduced to $Fe^{2+}$, recovering the original micelle and, therefore, a film forming operation can be carried out repeatedly using the same solution.

Electrolytic treatment as described above forms a thin film comprised of about 600 to 900 Å particles of the desired hydrophobic organic substance on the anode.

The supporting salt (supporting electrolyte) to be used in the process of the present invention is added, if necessary, in order to control the electrical conductance of the aqueous medium. The amount of the supporting salt added is usually about 10 to 300 times and preferably about 50 to 200 times that of the above surfactant (micelle forming agent). The type of the supporting salt is not critical as long as it is able to control the electric conductance of the aqueous medium without inhibiting the formation of the micelle and the deposition of the above hydrophobic organic substance.

More specifically, sulfuric acid salts (salts of lithium, potassium, sodium, rubidium, aluminum and the like) and acetic acid salts (salts of lithium, potassium, sodium, rubidium, beryllium, magnesium, calcium, strontium, barium, aluminum and the like) are suitable.

The electrode to be used in the process of the present invention may be a metal more noble than the oxidation potential (against +0.15 V saturated calomel electrode) of ferrocene, or an electrically conductive substance. More specifically, ITO (mixed oxide of indium oxide and tin oxide), platinum, gold, silver, glassy carbon, an electrically conductive metal oxide, an electrically conductive organic polymer and the like can be used.

Various hydrophobic organic substances can be used in the production of organic thin films according to the process of the present invention. As well as coloring matters for optical memory and organic coloring matters, such as phthalocyanine, metal complexes thereof, and derivatives thereof, naphthalocyanine, metal complexes thereof and derivatives thereof, porphyrin, porphyrin derivatives (tetra phenyl porphyrin and the like) and its metal complexes, electrochromic materials such as 1,1,-diheptyl-4,4'-bipyridinium dibromide, 1,1'didodecyl-4,4'-bipyridinium dibromide and the like, light sensitive materials (photochromic materials) and light sensor materials, such as 6-nitro-1,3,3-trimethyl-spiro-(2'H-1'benzopyran-2,2'-indoline) (commonly called spiropyran) and the like, liquid crystal display coloring matters such as p-azoxyanisole and the like, electrically conductive organic materials and gas sensor materials, such as the 1:1 complex of 7,7,8,8-tetracyanoquinonedimethane (TCNQ) and tetrathiafulvalene (TTF), light curable paints such as pentaerythritol diacrylate and the like, insulating materials such as stearic acid and the like, diazo-type light-sensitive materials and paints such as 1-phenylazo-2-naphthol and the like, can be used. Other examples of water-insoluble polymers include general purpose polymers such as polycarbonate, polystyrene, polyethylene, polypropylene, polyamide, polyphenylene sulfide (PPS), polyphenylene oxide (PPO), polyacrylonitrile (PAN) and the like, polyphenylene, polypyrrole, polyaniline, polythiophene, acetyl cellulose, polyvinyl acetate, polyvinyl butyral, and various polymers (polyvinyl pyridine and the like) and copolymers (a copolymer of methyl methacrylate and methacrylic acid) and the like.

The present invention will hereinafter be explained in more detail with reference to Examples and Comparative Examples.

EXAMPLE 1

An amount of 0.5 g of 1-ferrocenyl-11-bromoundecane and 0.1 ml of pyridine were mixed and reacted for 120 hours in a nitrogen atmosphere while heating at 60° C. on a water bath. In 4 hours from the start of the reaction, at least 95% of the reaction was completed. This reaction mixture solidified with an advance of the reaction and finally solidified. This solid powder was well washed by adding 10 ml of dimethyl ether. After washing, the powder was separated by filtration. After the powder was fully dried, 10 ml of acetone was added thereto to dissolve it therein. Upon addition of 10 ml of dimethyl ether to the solution, a precipitate was obtained. This operation was repeated three times, and after drying, 0.22 g of a purified product was obtained (yield, 38%).

Figure 2:
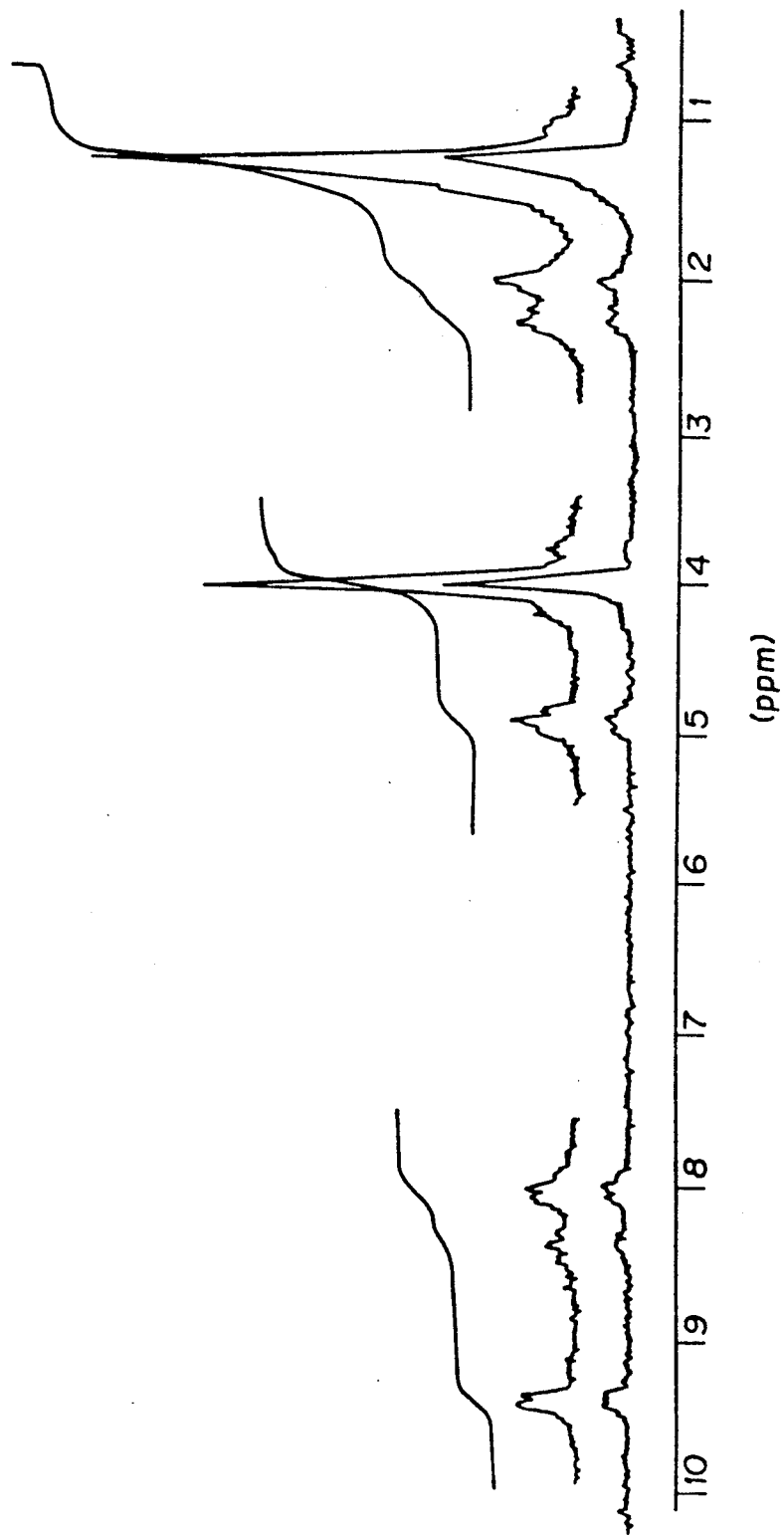
FIG. 2 is a proton nuclear magnetic resonance ($^1$HNMR) spectrum of the ferrocene derivative obtained in Example 1.
Figure 3:
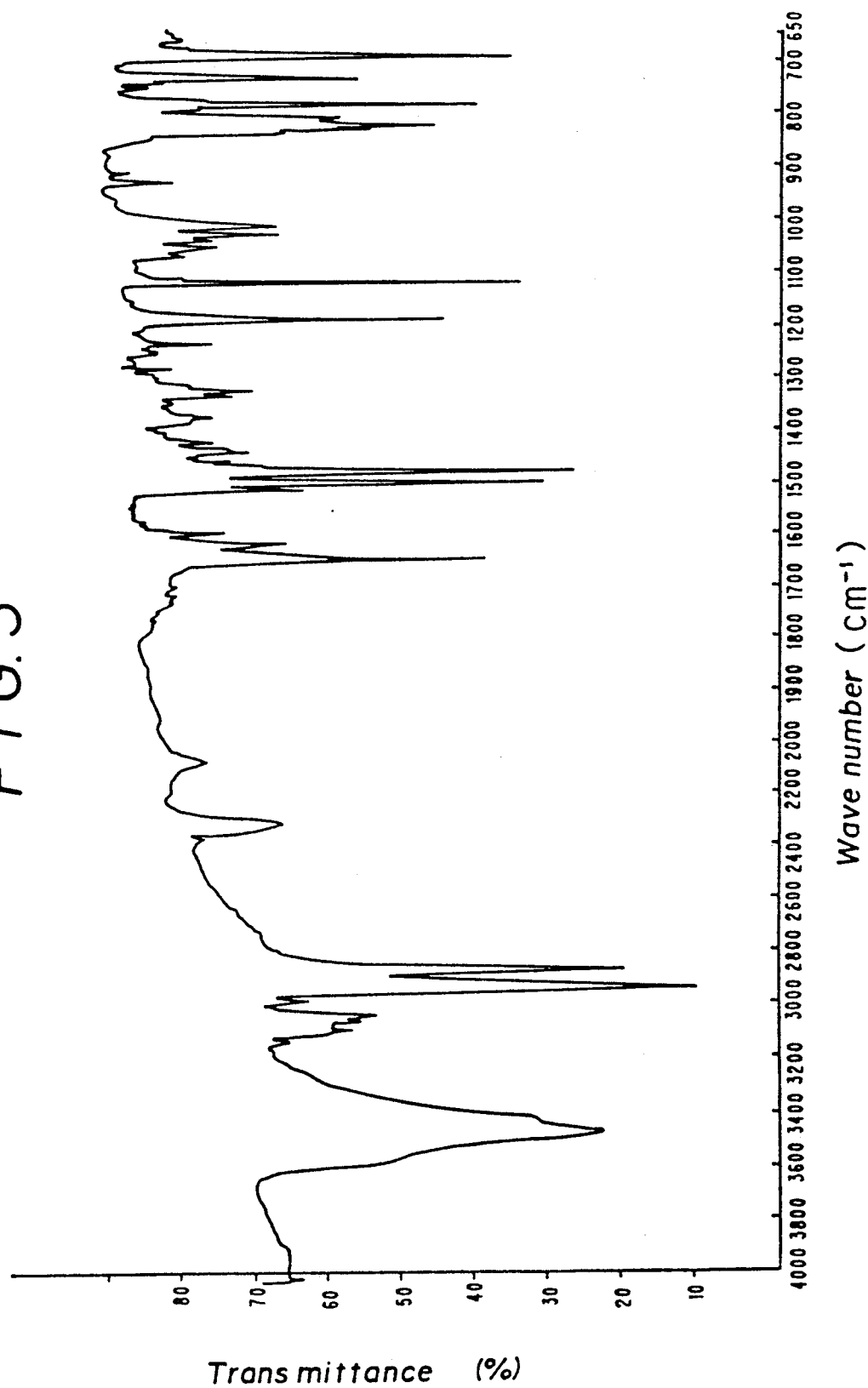
FIG. 3 is an infrared (IR) absorption spectrum of the ferrocene derivative obtained in Example 1.
Figure 4:
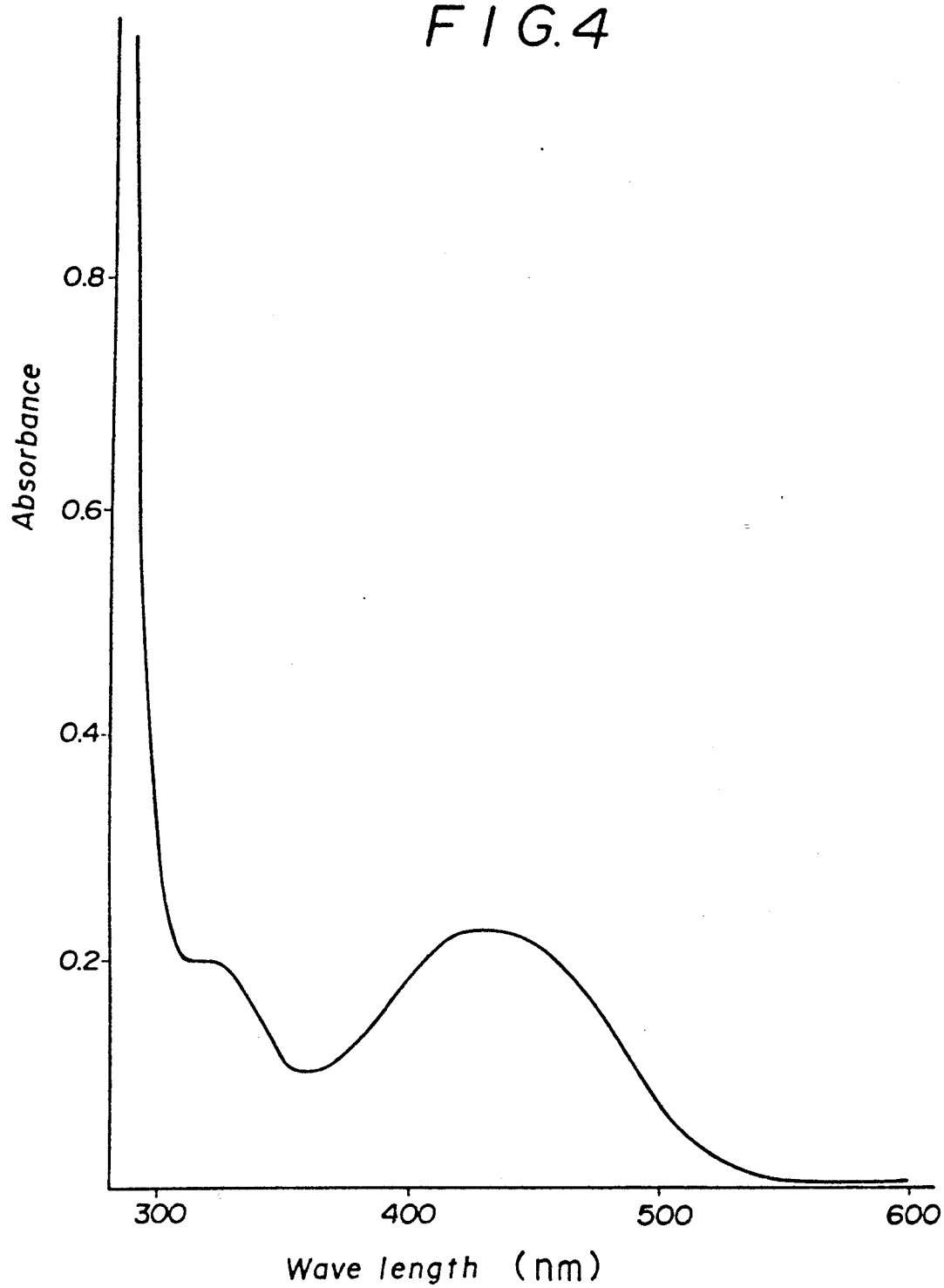
FIG. 4 is an ultraviolet-visible (UV-VIS) absorption spectrum of the ferrocene derivative of Example 1.

The elemental analytical values of the substance were as shown below. The results of measurement of proton nuclear magnetic resonance ($^1$H-NMR) spectrum (CDCl$_3$, TMS standard) are as shown in FIG. 2, the results of measurement of infrared (IR) absorption spectrum (KBr tablet method, 25° C.) are as shown in FIG. 3, and the results of measurement of ultraviolet-visible (UV-VIS) absorption spectrum are as shown in FIG. 4.

|  | Elemental Analytical Values (%) | | |
| --- | --- | --- | --- |
|  | Carbon | Hydrogen | Nitrogen |
| Calculated | 62.67 | 7.28 | 2.81 |
| Found | 62.08 | 7.65 | 2.73 |

The above results confirmed that the above substance was a ferrocene derivative represented by the formula:

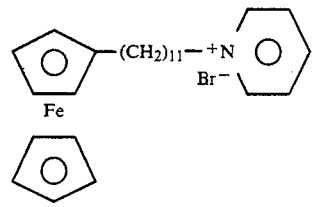

EXAMPLE 2

Figure 5:
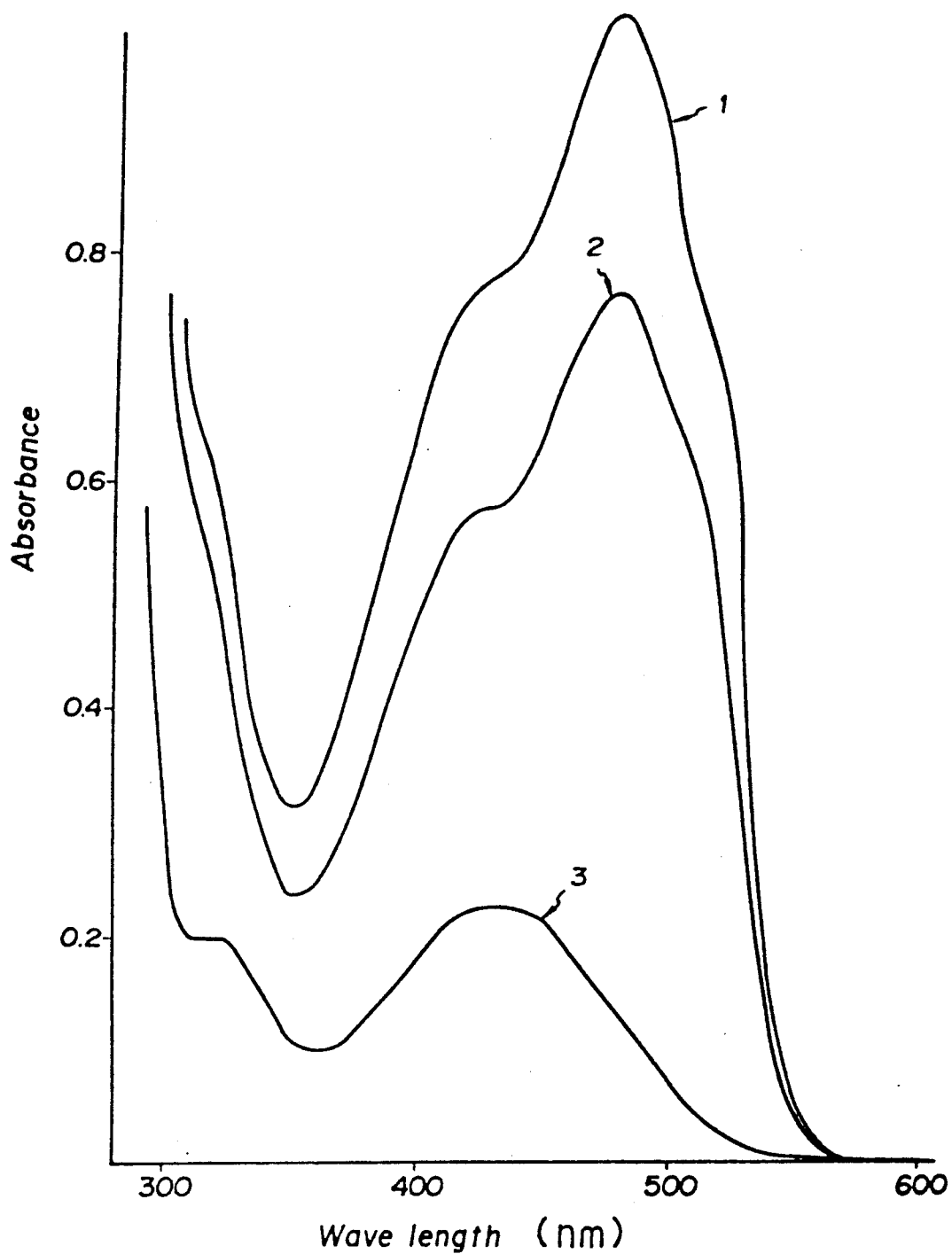
FIG. 5 indicates UV-VIS absorption spectra of the supernatants obtained in Example 2 and Comparative Example 1.

To 100 ml of water, 99.6 mg of the ferrocene derivative obtained in Example 1 as a surfactant (micelle forming agent) and 2.56 g of lithium sulfate as a supporting salt were added, and 10 mg of 1-phenylazo-2-naphthol was added and dispersed and dissolved by application of supersonic waves for 10 minutes. The resulting mixture was further stirred for two days and nights with a stirrer, and then the micelle solution thus obtained was subjected to centrifugal separation at 2,000 rpm for one hour. A UV-VIS absorption spectrum of the supernatant is shown in FIG. 5 (indicated by (1)). This confirmed that 1-phenylazo-2-naphthol was made soluble in the micelle solution. The solubility was 59 μM/2 mM micelle forming agent solution. For comparison, a solution of only the surfactant without addition of 1-phenylazo-2-naphthol was prepared, and its UV-VIS absorption spectrum is shown in FIG. 5 (indicated by (3)).

COMPARATIVE EXAMPLE 1

To 100 ml of water, 95.6 mg of a ferrocene derivative having the formula:

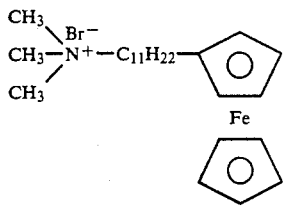

as a surfactant (micelle forming agent) and 2.56 g of lithium sulfate as a supporting salt were added, and 10 mg of 1-phenylazo-2-naphthol was added and dispersed and dissolved by application of supersonic waves for 10 minutes. The resulting mixture was further stirred for two days and nights by the use of a stirrer, and the micelle solution thus obtained was subjected to centrifugal separation at 2,000 rpm for one hour. A UV-VIS absorption spectrum of the supernatant is shown in FIG. 5 (indicated by (2)). The solubility of the 1-phenylazo-2-naphthol was 38 μM/2 mM micelle forming agent solution.

From the above results, it can be seen that when the micelle forming agent of Example 1 is used, 1-phenylazo-2-naphthol is dissolved in an amount of about 1.5 times that when the micelle forming agent of Comparative Example 1 is used.

EXAMPLE 3

In 100 ml of water, 0.02 mol of lithium sulfate as a supporting salt was dissolved, and as a micelle forming agent, 0.2 m mol of the ferrocene derivative obtained in Example 1 was added and dispersed by application of supersonic waves to form a micelle. Then, 0.2 m mol of a coloring matter (1-phenylazo-2-naphthol), which was a hydrophobic organic substance, was added and incorporated in the micelle by application of supersonic waves. After the mixture was stirred for two days and nights, an excess of the coloring matter was removed by centrifugal separation to obtain a micelle solution. Using the micelle solution as an electrolyte, ITO as the anode, platinum as the cathode, and a saturated calomel electrode as a reference electrode, electrolytic treatment was performed under the conditions of temperature 25° C., applied voltage 0.3 V, current density 36 μA/cm$^2$. After 60 minutes, a coloring matter thin film having primary particles having an average particle size of 700 to 1,000 Å was obtained on the ITO.

Figure 6:
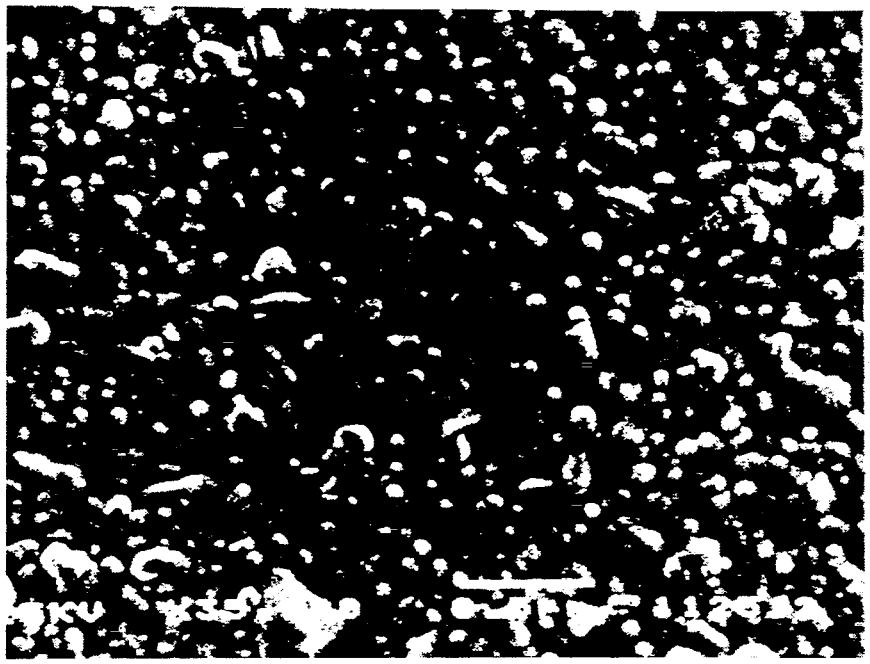
FIG. 6 is an electron micrograph showing the surface structure of the thin film formed in Example 3.

A scanning type electron microscope (SEM) photograph (magnification, 35,000 using JSM-T220 produced by Nippon Denshi Co., Ltd.) of the coloring matter thin film formed is shown in FIG. 6. A UV absorption spectrum of the thin film dissolved in ethanol is shown in FIG. 7 (Curve (3)). A UV absorption spectrum of the above coloring matter in ethanol is shown in FIG. 7 (Curve (1)). Since the absorption peaks of Curves (3) and (1) are in agreement with each other, it can be seen that the thin film on the ITO is made of the above coloring matter.

The deposited amount of the thin film was 18 nano mol/cm$^2$.

EXAMPLE 4

In 100 ml of water was dissolved 0.02 mol of lithium sulfate as a supporting salt, and as a micelle forming agent, 0.2 m mol of the same ferrocene derivative as used in Comparative Example 1 was added and dispersed by application of supersonic waves to form a micelle. Then, 0.2 m mol of a coloring matter (1-phenylazo-2-naphthol) which was a hydrophobic organic substance was added to the micelle solution and incorporated in the micelle by application of supersonic waves. After the resulting mixture was stirred for two days and nights, an excess of the coloring matter was removed by centrifugal separation to obtain a micelle solution. Using this micelle solution as an electrolyte, ITO as the anode, platinum as the cathode, and a saturated calomel electrode as a reference electrode, electrolytic treatment was performed under the conditions of temperature 25° C., applied voltage 0.3 V, current density 35 μA/cm$^2$. After 60 minutes, a coloring matter thin film having primary particles having an average particle size of 700 Å was obtained on the ITO.

Figure 8:
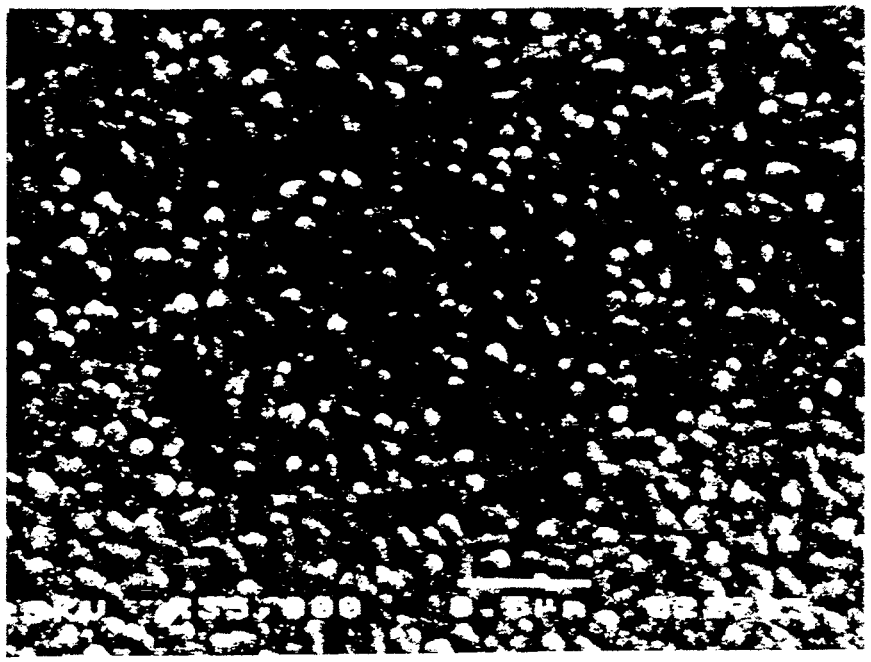
FIG. 8 is an electron micrograph showing the surface structure of the thin film formed in Example 4.

A scanning type electron microscope (SEM) photograph (magnification, 35,000, using JSM-T220 produced by Nippon Denshi Co., Ltd.) of the coloring matter thin film formed is shown in FIG. 8. A UV absorption spectrum of the thin film dissolved in ethanol is shown in FIG. 7 (Curve (2)). A UV absorption spectrum of the above coloring matter dissolved in ethanol is shown in FIG. 7 (Curve (1)). Since the absorption peaks of Curves (2) and (1) are in agreement with each other, it can be seen that the thin film on the ITO is made of the above coloring matter.

The deposited amount of the thin film was 12 nano mol/cm$^2$.

PREPARATION EXAMPLE 5

(1) 11-undecanic acid chloride prepared from 50.0 g of 11-bromoundecanic acid and 90.0 g of thionyl chloride, 37.6 g of anhydrous aluminum chloride, and 35.0 g of ferrocene were reacted at 5° C. for 3 hours in a methylene chloride solvent. After the completion of the reaction, the reaction mixture was treated with diluted hydrochloric acid and then purified with a silica gel column to obtain 56.9 g of 10-bromo undecanyl ferrocenyl ketone represented by the following formula:

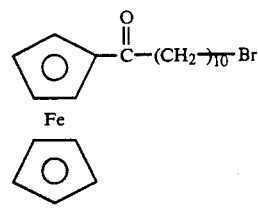

(2) In the presence of amalgam prepared from 65.4 g of zinc and 27.2 g of mercuric chloride, 56.9 g of 10-bromodecanyl ferrocenyl ketone prepared in (1) above was refluxed for 6 hours in a mixed solvent of concentrated hydrochloric acid and ethanol to perform a reduction reaction.

After the completion of the reaction, the reaction mixture was extracted with ethyl acetate and purified on a silica gel column to obtain 42.1 g of 1-ferrocenyl-11-bromoundecane represented by the following formula:

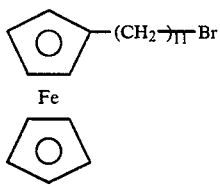

EXAMPLE 5

Figure 9:
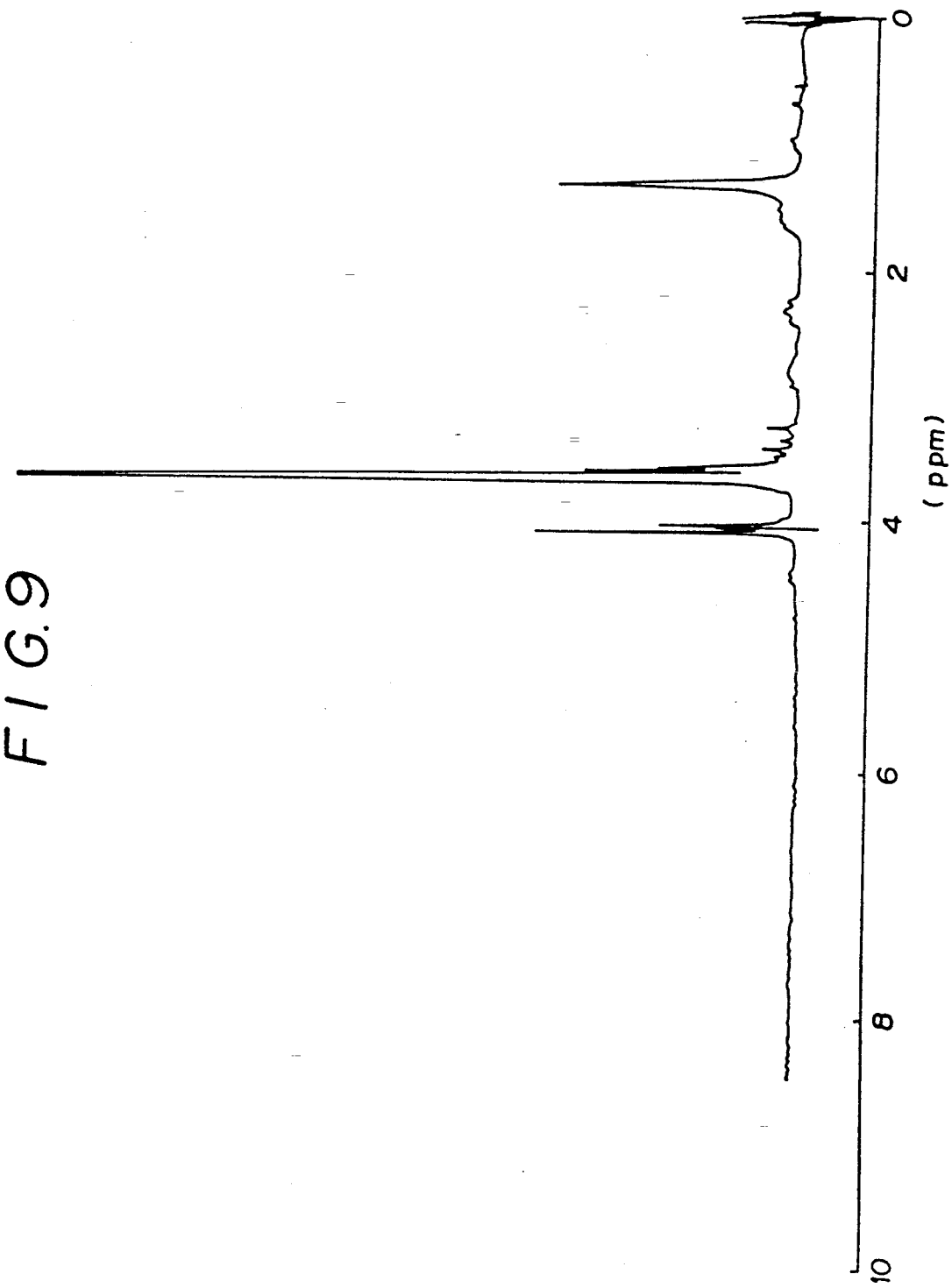
FIG. 9 is $^1$H-NMR of the ferrocene derivative obtained in Example 5.

An amount of 0.064 g of metallic sodium was added to 6.5 g of polyethylene glycol (average molecular weight, 600), and stirred at 70° C. for one day and night. Then, 1.1 g of 1-ferrocenyl-11-bromoundecane was added and reacted at 110° C. for 10 hours. This reaction solution was extracted with a 1:1 mixture of water and n-butanol. The extract was washed with water and then was subjected to chromatographic purification by developing on a silica gel column with a mixture of benzene and ethanol (benzene: ethanol=5:1) as a solvent. After drying, a purified product was obtained, and the yield was 41% and the amount was 0.96 g. The elemental analytical values of the purified product were carbon 60.21%, hydrogen 9.46%, nitrogen 0.00%. The results of measurement of the proton nuclear magnetic spectrum ($^1$HNMR) are as shown in FIG. 9.

From the above results, it can be seen that the above purified product is a ferrocene derivative having the following structure:

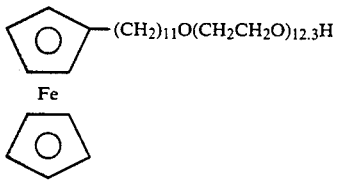

EXAMPLE 6

Figure 10:
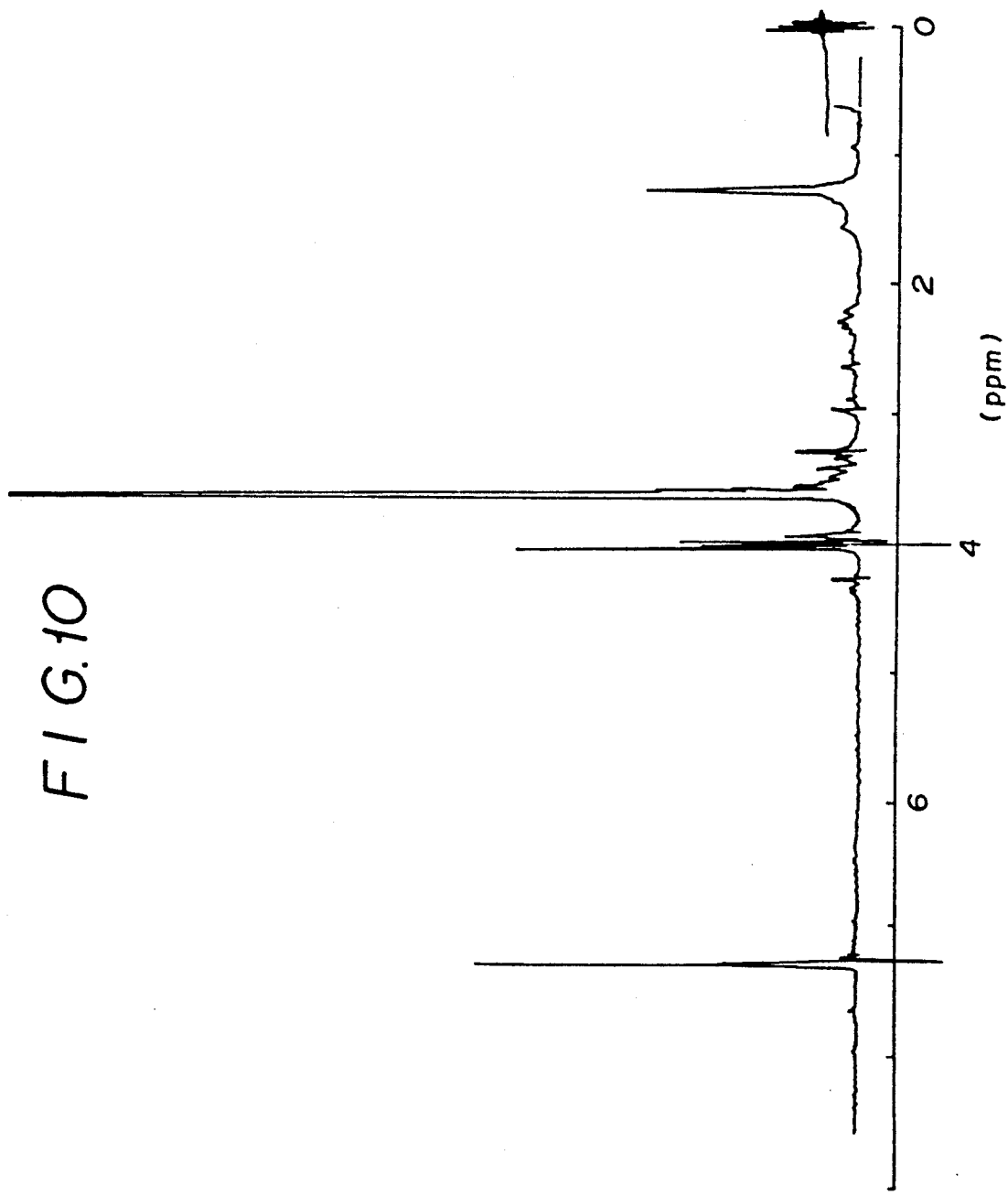
FIG. 10 is $^1$H-NMR of the ferrocene derivative obtained in Example 6.

The procedure of Example 5 was repeated with the exception that polyethylene glycol having an average molecular weight of 1,000 was used. For the purified product obtained, the yield was 31% and the amount was 2.15 g. The results of measurement of $^1$H-NMR of the purified product are as shown in FIG. 10.

From the above results, it can be seen that the above purified product is a ferrocene derivative having the following structure:

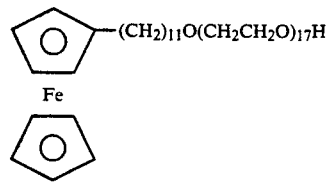

PREPARATION EXAMPLE 7

(1) In the presence of 9.6 g of anhydrous aluminum chloride, 13.5 g of ferrocene and 19.9 g of 11-ethoxycarbonylundecanic acid chloride (known as described in J. Amer. Chem. Soc., 69, 2350 (1947)) were reacted at room temperature for 2 hours in a methylene chloride solvent.

After the completion of the reaction, the reaction mixture was treated with diluted hydrochloric acid and then purified with a silica gel column to obtain 13.7 g of ethyl ferrocenoylundecanate represented by the following formula:

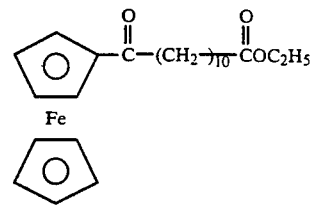

(2) An amount of 12.4 g of ethyl ferrocenoylundecanate prepared in (1) above and 2.9 g of potassium hydroxide were refluxed for 2 hours in an ethanol solvent and then was subjected to acid treatment to obtain 11.3 g of ferrocenoylundecanic acid represented by the following formula:

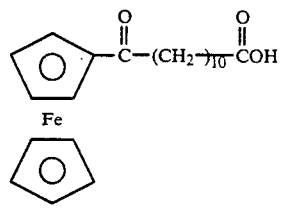

(3) In the presence of zinc amalgam prepared from 6.5 g of zinc and 2.7 g of mercuric chloride, 6.0 g of ferrocenoylundecanic acid prepared in (2) above was reacted at 80° C. for 3 hours in a mixed solvent of concentrated hydrochloric acid and ethanol.

After the completion of the reaction, the reaction mixture was extracted with ethyl acetate and purified with a silica gel column to obtain 4.8 g of ferrocenyldodecanic acid represented by the following formula:

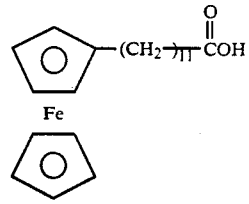

EXAMPLE 7

Figure 11:
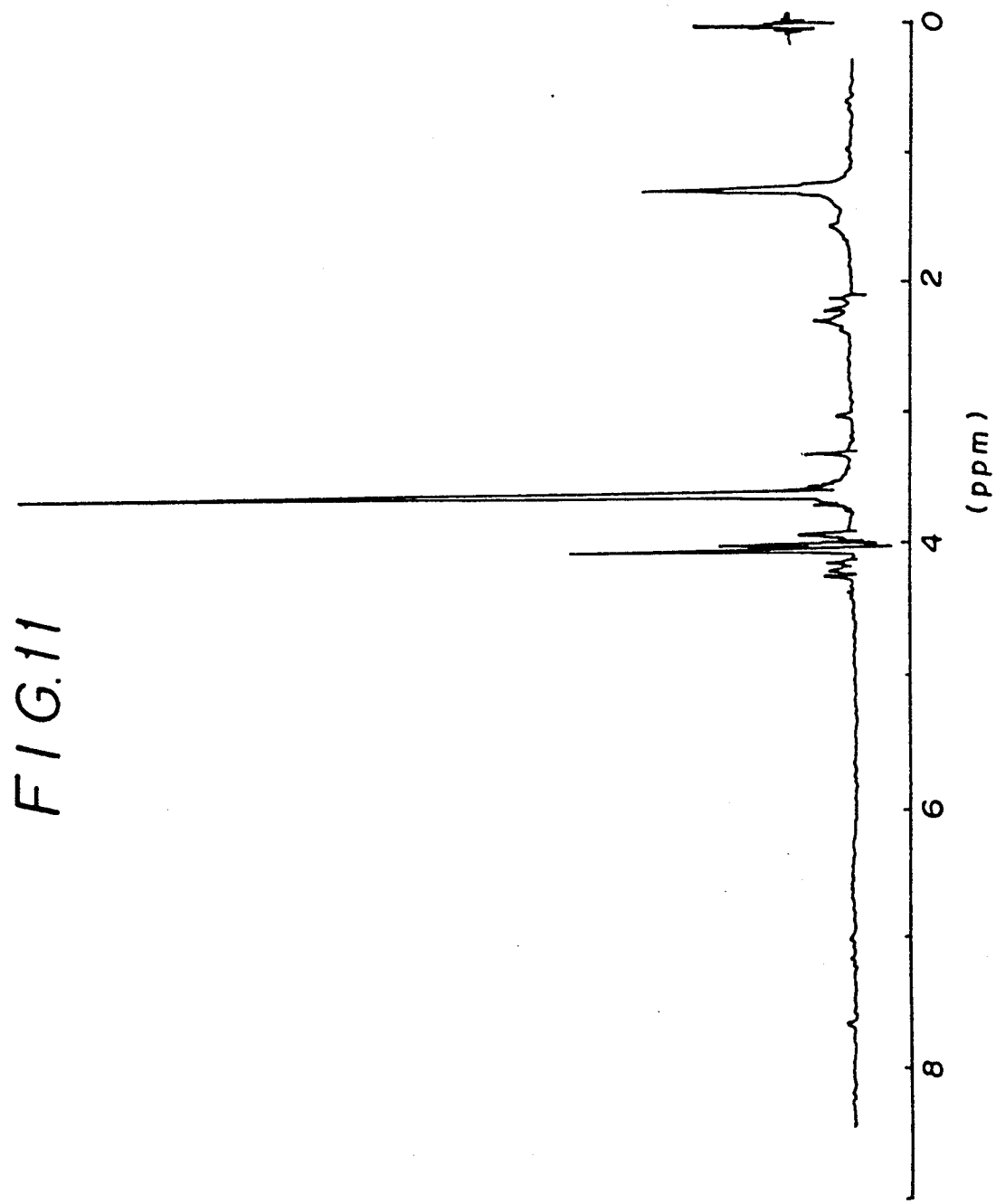
FIG. 11 is $^1$H-NMR of the ferrocene derivative obtained in Example 7.

The procedure of Example 5 was repeated with the exception that 6 g of polyethylene glycol (average molecular weight, 600) and 0.1 cc of concentrated sulfuric acid were added to 0.29 g of ferrocenyldodecanic acid (obtained in preparation Example 7) and reacted at 80° C. for 6 hours. For the purified product obtained, the yield was 62% and the amount was 0.44 g. The results of measurement of $^1$H-NMR of the purified product are as shown in FIG. 11.

From the above results, it can be seen that the above purified product is a ferrocene derivative having the following structure:

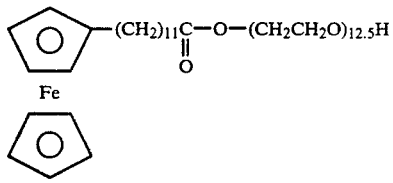

EXAMPLE 8

An amount of 1.13 mg of the ferrocene derivative obtained in Example 5 was added to 31.5 ml of water as a surfactant (micelle forming agent), and 10 mg of phthalocyanine was added and dispersed and dissolved by stirring for 10 minutes with supersonic waves. The mixture was further stirred for two days and nights by the use of a stirrer, and then the micelle solution thus obtained was subjected to centrifugal separation at 2,000 rpm for one hour. A visible absorption spectrum of the supernatant is shown in FIG. 12 (indicated by A). This confirmed that the phthalocyanine was made soluble in the micelle solution. The solution was 4.4 mM/4 mM micelle forming agent solution.

EXAMPLE 9

The procedure of Example 8 was repeated with the exception that the phthalocyanine was replaced by a phthalocyanine-iron complex. A visible absorption spectrum of the supernatant is shown in FIG. 12 (indicated by B). This confirmed that the phthalocyanine was made soluble in the micelle solution. The solubility was 0.72 mM/4 mM micelle forming agent solution.

EXAMPLE 10

The procedure of Example 8 was repeated with the exception that the phthalocyanine was replaced by a phthalocyaninecobalt complex. A visible absorption spectrum of the supernatant is shown in FIG. 12 (indicated by C). This confirmed that the phthalocyanine was made soluble in the micelle solution. The solubility was 0.22 mM/4 mM micelle forming agent solution.

EXAMPLE 11

The procedure of Example 8 was repeated with the exception that the phthalocyanine was replaced by a phthalocyanine-copper complex. A visible absorption spectrum of the supernatant is shown in FIG. 12 (indicated by D). This confirmed that the phthalocyanine was made soluble in the micelle solution. The solubility was 0.11 mM/4 mM micelle forming agent solution.

EXAMPLE 12

The procedure of Example 8 was repeated with the exception that the phthalocyanine was replaced by a phthalocyanine-zinc complex. A visible absorption spectrum of the supernatant is shown in FIG. 12 (indicated by E). This confirmed that the phthalocyanine was made soluble in the micelle solution. The solubility was 0.41 mM/4 mM micelle forming agent solution.

EXAMPLE 13

Figure 14:
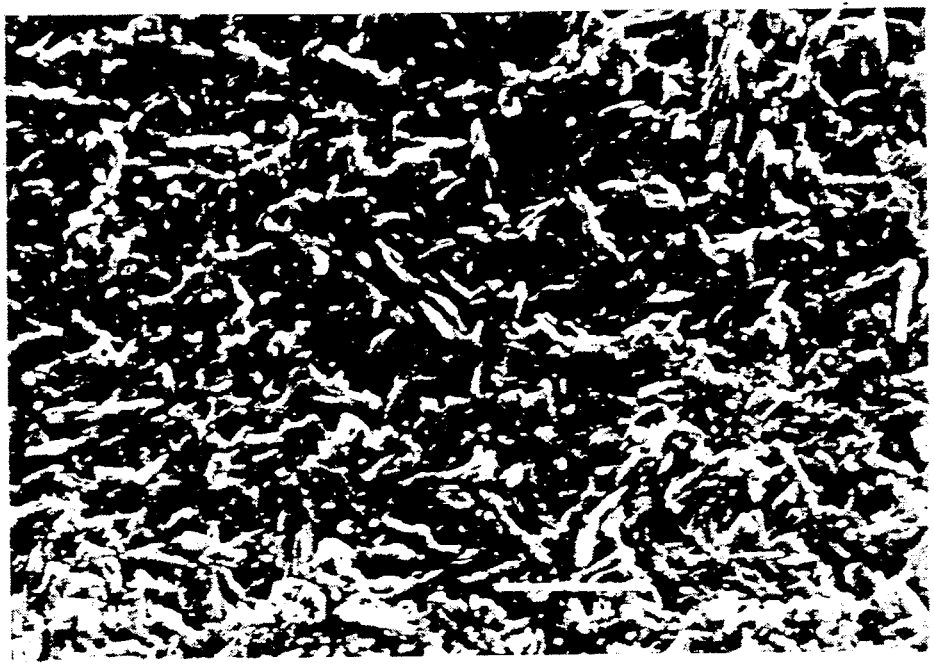
FIG. 14 is an electron micrograph showing the surface structure of the thin film formed in Example 13.

To 10 ml of the micelle solution prepared in Example 8 was added 0.22 g of lithium sulfate ($Li_2SO_4$) to obtain a 0.44 mM phthalocyanine/2 mM micelle forming agent/0.2M lithium sulfate solution. Using this solution as an electrolyte, ITO as the anode, platinum as the cathode and a saturated calomel electrode as a reference electrode, constant voltage electrolysis of applied voltage 0.5 V and current 7 μA was performed at 25° C. for 2 hours. As a result, a coloring matter thin film having primary particles having an average particle size of 1,000 Å was formed on the ITO. A SEM photograph (magnification, 20,000, using JSM-T220 produced by Nippon Denshi Co., Ltd.) of the coloring matter thin film is shown in FIG. 14.

A visible absorption spectrum of the coloring matter thin film on the ITO is shown in FIG. 13 (indicated by A). Since the visible absorption spectra shown in FIG. 13 (indicated by A) and FIG. 12 (indicated by A) were in agreement with each other, it was confirmed that the coloring matter thin film on the ITO was made of the phthalocyanine.

EXAMPLE 14

The procedure of Example 13 was repeated with the exception that the electrolytic time was changed to 40 minutes.

A visible absorption spectrum of the coloring matter thin film thus formed is shown in FIG. 13 (indicated by A). By comparison of A of FIG. 13 with B of FIG. 13, it can be seen that the thin film formed has a small absorption spectrum as compared with Example 13, and the film thickness can be controlled by the electrolytic time.

EXAMPLE 15

The procedure of Example 4 was repeated with the exception that platinum was used as the anode and the current density was changed to 38 μA/$cm^2$.

A UV absorption spectrum of the formed thin film dissolved in ethanol is shown in FIG. 15 (Curve B). A UV absorption spectrum of the coloring matter (1-phenylazo-2-naphthol) dissolved in ethanol is shown in FIG. 15 (Curve C), and a UV absorption spectrum of the thin film formed in Example 4, as dissolved in ethanol is shown in FIG. 15 (Curve D).

EXAMPLE 16

The procedure of Example 4 was repeated with the exception that glassy carbon was used as the anode and the current density was changed to 40 μA/$cm^2$.

An ultraviolet absorption spectrum of the formed thin film dissolved in ethanol is shown in FIG. 15 (Curve A).

EXAMPLE 17

Figure 16:
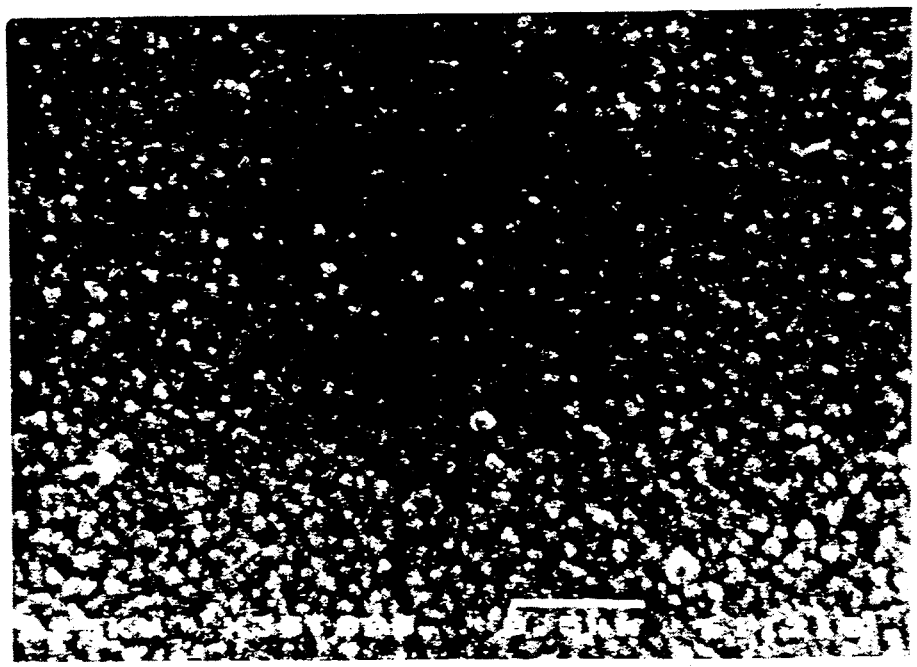
FIG. 16 is an electron micrograph showing the surface structure of the thin film formed in Example 17.

The procedure of Example 4 was repeated with the exception that as the micelle forming agent, a compound having the formula:

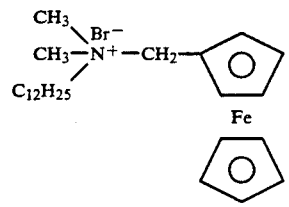

was used, and the current density was changed to 30 μA/$cm^2$. A SEM photograph (magnification, 35,000, using JSM-T220 produced by Nippon Denshi Co., Ltd.) of the thin film formed is shown in FIG. 16.

EXAMPLE 18

A thin film was formed on ITO in the same manner as in Example 4 except that as the coloring matter, 1,1'-didodecyl-4,4'-bipyridinium dibromide was used, and the current density was changed to 58 $\mu A/cm^2$.

Figure 17:
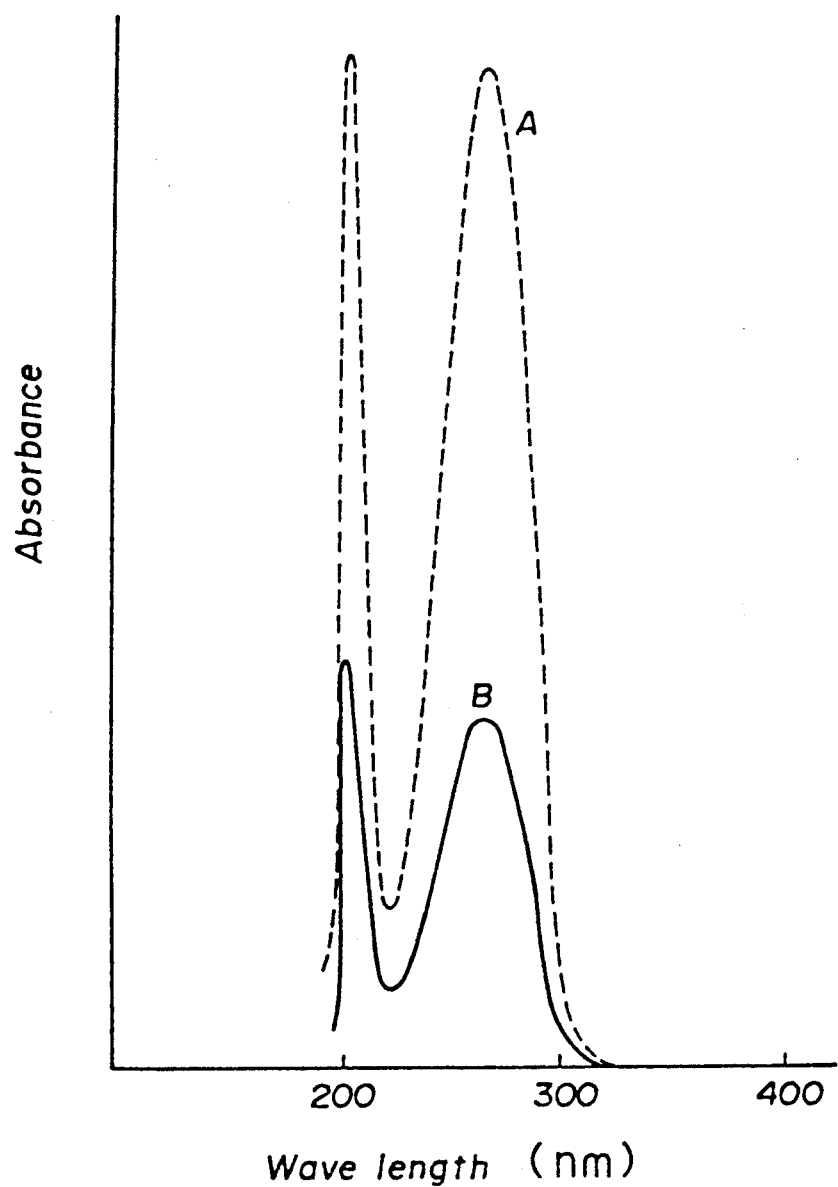
FIG. 17 is a UV absorption spectrum of the methanol solution of the thin film formed in Example 18.

A UV absorption spectrum of the formed thin film dissolved in methanol is shown in FIG. 17 (Curve B). A UV absorption spectrum of the above coloring matter dissolved in methanol (concentration, 0.042 m mol/l) is shown in FIG. 17 (Curve A). Since the absorption peaks of Curves A and B are in agreement with each other, it can be seen that the thin film on the ITO is made of the above coloring matter.

EXAMPLE 19

Figure 18:
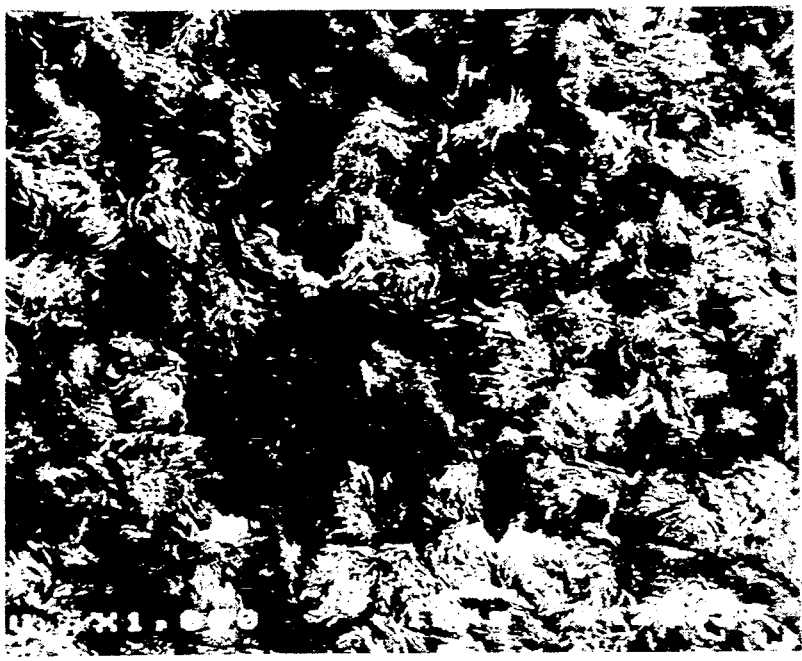
FIG. 18 is an electron micrograph showing the surface structure of the thin film formed in Example 19.

A thin film was formed in the same manner as in Example 18 except that glassy carbon was used as the anode, and the current density was changed to 60 $\mu A/cm^2$. A SEM photograph (magnification, 1,000, using JSM-T220 produced by Nippon Denshi Co., Ltd.) of the thin film is shown in FIG. 18.

EXAMPLE 20

An amount of 0.02 mol (concentration, 0.2M) of lithium sulfate as a supporting salt was dissolved in 100 cc of secondary distilled water, and 0.3 m mol (concentration, 3 mM) of the same surfactant (micelle forming agent) comprising a ferrocene derivative, as used in Comparative Example 1 was added thereto and dispersed by stirring to form a micelle.

An amount of 0.82 nano mol (concentration, 8.2 nM) of a water insoluble copolymer of methyl methacrylate and methacrylic acid (molecular weight, $1\times10^6$) was added to the micelle solution and incorporated in the micelle by application of supersonic waves and stirring for one day and night.

Using ITO as the anode, platinum as the cathode, and a saturated calomel electrode as a reference electrode, electrolytic treatment was performed under the conditions of temperature 25° C. applied voltage 0.3 V and current density 10 $\mu A/cm^2$ to obtain a polymer film on the ITO. This ITO was washed with water and then, upon application of cyclic voltammetry in an aqueous solution containing only a supporting salt (lithium sulfate, concentration 0.2M), an oxidation reduction wave due to the micelle forming agent incorporated in the film was observed. However, by sweeping continuously 20 times 0 to +0.5 V (against the saturated calomel electrode) at a sweeping speed of 20 mV/sec in the above aqueous solution, the height of the wave was decreased to 10% of the initial value. That is, 90% of the micelle forming agent incorporated in the film could be removed by this post-treatment.

Figure 19A:
FIG. 19(a) is an electron micrograph showing the surface structure of the thin film before post-treatment as formed in Example 20.
Figure 19B:
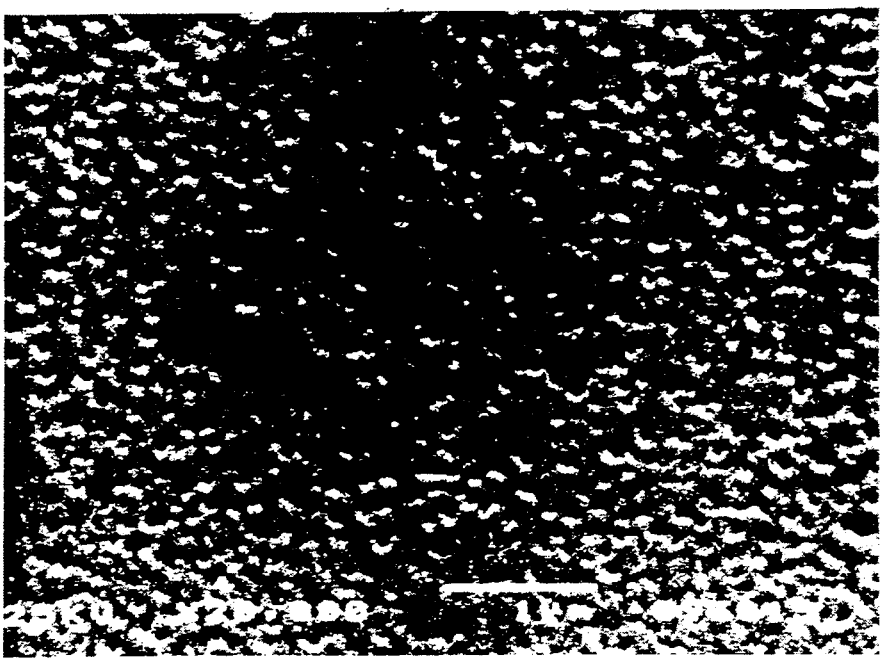
FIG. 19(b) is an electron micrograph showing the surface structure of the thin film after post-treatment as formed in Example 20.

A SEM photograph (magnification, 20,000, using JSM-T220 produced by Nippon Denshi Co., Ltd.) of the polymer film formed is shown in FIG. 19 (a), (b). FIG. 19(a) is a photograph of the film before post-treatment, and FIG. 19(b) is a photograph of the film after post-treatment (film thickness: 1,800 Å; amount of electricity: 0.1 Coulomb/$cm^2$; film area: 0.91 $cm^2$).

A Fourier transformation infrared (FT-IR) absorption spectrum of the polymer film is shown in FIG. 20 (film thickness: 5,600 Å; amount of electricity: 0.31 Coulomb/$cm^2$; film area: 1.64 $cm^2$), and an IR absorption spectrum with a KBr pellet of the polymer used as the material is shown in FIG. 21. Since the absorption peaks of FIGS. 20 and 21 are in agreement with each other, it can be seen that the film on the ITO is made of the above polymer.

Figure 22:
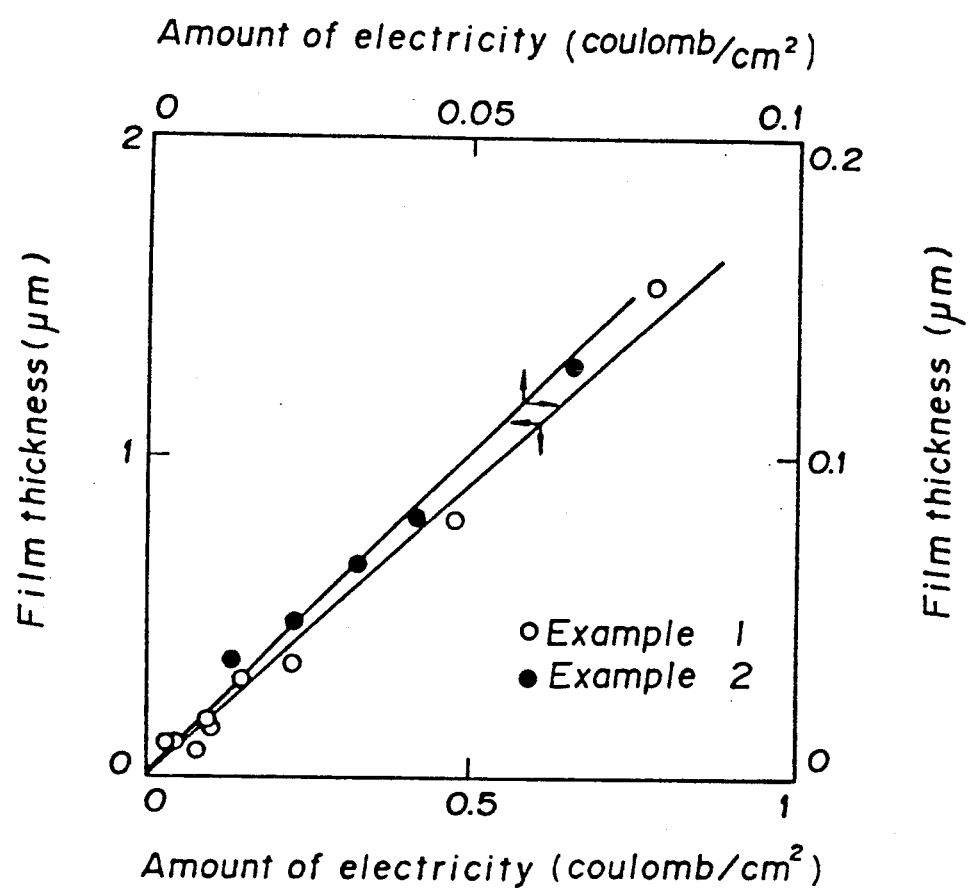
FIG. 22 is a graph showing a relation between the film thickness of the thin film formed in Examples 20 and 21, and the amount of electricity having passed per unit area of ITO.

A relation between the film thickness and the amount of electricity having passed per unit area of the ITO is shown in FIG. 22. Since, as can be seen from FIG. 22, there is a straight line relation (parallel relation) between the film thickness and the amount of electricity having passed, it can be seen that the film thickness can also be controlled at will be controlling the amount of electricity.

EXAMPLE 21

The procedure of Example 20 was repeated with the exception that as the polymer, poly(4-vinylpyridine) (molecular weight, 50,000, concentration, 7.9 $\mu M$ produced by Polyscience Inc.) was used, and the concentration of the micelle forming agent was changed to 2.0 mM.

Figure 24:
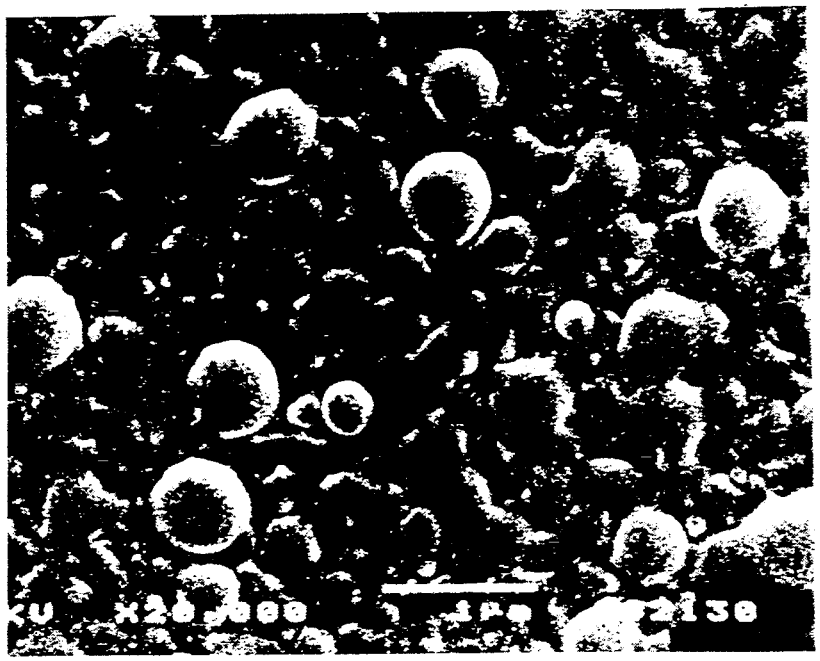
FIG. 24 is an electron micrograph showing the surface structure of the thin film formed in Example 21.
Figure 23:
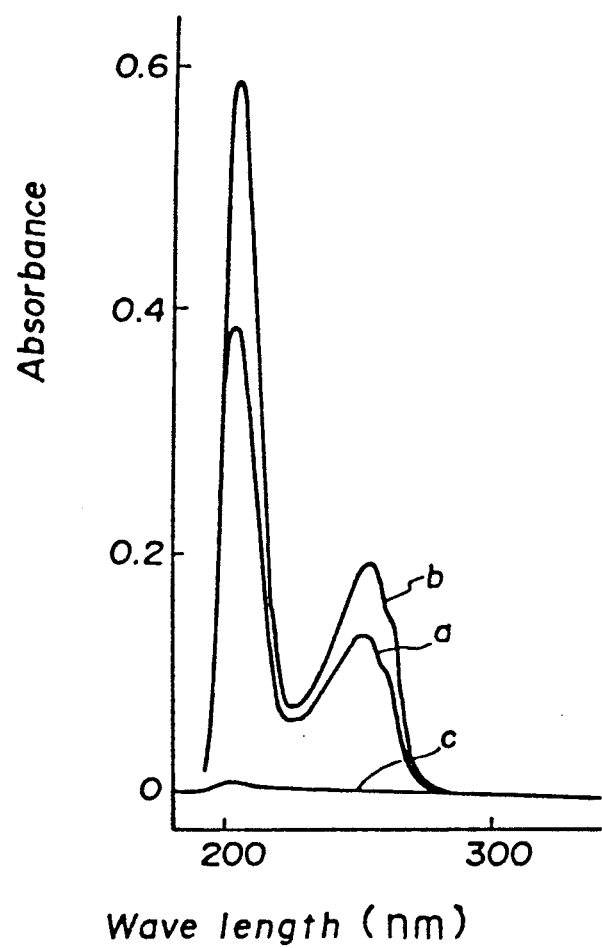
FIG. 23 is a UV absorption spectrum of the thin film formed in Example 21.

A UV absorption spectrum of the formed film (film thickness: 400 Å; amount of electricity: 0.019 Coulomb/$cm^2$; film area: 1.05 $cm^2$) dissolved in 5 ml of ethanol is shown in FIG. 23 (Curve a). A SEM photograph (magnification, 20,000, using JSM-T220 produced by Nippon Denshi Co., Ltd.) of the formed thin film is shown in FIG. 24. A UV absorption spectrum of the above polymer dissolved in ethanol (polymer concentration, 0.25 $\mu M$) is shown in FIG. 23 (Curve b). Since the absorption peaks and wave forms of Curves a and b are in agreement with each other, it can be seen that the film on the ITO is made of the above polymer. Curve c of FIG. 23 is a UV absorption spectrum of a washing liquid resulting from washing of ITO with 5 ml of ethanol, said ITO having been obtained by electrolysis of a micelle solution not containing a polymer.

A relation between the film thickness and the amount of electricity having passed through per unit area of the ITO is shown in FIG. 22. Since, as can be seen from FIG. 22, there is a straight line relation (parallel relation) between the film thickness and the amount of electricity having passed, it can be seen that the film thickness can also be controlled at will be controlling the amount of electricity.

EXAMPLE 22

To 31.5 ml of water was added 1.13 mg of the ferrocene derivative obtained in Example 7, as a surfactant (micelle forming agent), and 10 mg of phthalocyanine was added and dispersed and dissolved by stirring for 10 minutes with supersonic waves. The mixture was further stirred for two days and nights by the use of a stirrer, and micelle solution thus obtained was subjected to centrifugal separation at 2,000 rpm for one hour. A visible absorption spectrum of the supernatant confirmed that the phthalocyanine was made soluble in the micelle solution. The solubility was 8.9 mM/4 mM micelle forming agent solution.

PREPARATION EXAMPLE 23

(1) In the same manner as in Preparation Example 7 (1) except that in place of 11-ethoxycarbonylundecanic acid chloride shown in Preparation Example 7 (1), 35.0 g of 10-ethoxycarbonyldecanic acid chloride was used, and 17.7 g of anhydrous aluminum chloride was used and 24.7 g of ferrocene was reacted; 23.0 g of ethyl ferrocenoyldecanate represented by the formula shown below was obtained.

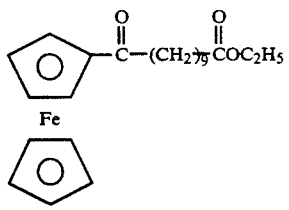

(2) In the same manner as in Preparation Example 7 (2) except that in place of ethyl ferrocenoylundecanate shown in Preparation Example 7 (2), 5.0 g of ethyl ferrocenoyldecanate (obtained in (1) above) was used, and 1.2 g of potassium hydroxide was used; 4.7 g of ferrocenoyldecanic acid represented by the formula shown below was obtained.

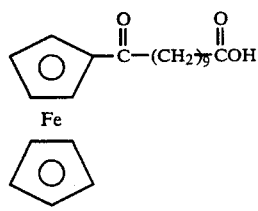

(3) In the same manner as in Preparation Example 7 (3) except that in place of ferrocenoylundecanic acid shown in Preparation Example 7 (3), 4.7 g of ferrocenoyldecanic acid (obtained in (2) above) was used, and 6.6 g of zinc and 2.7 g of mercuric chloride were used; 3.4 g of ferrocenylundecanic acid represented by the formula shown below was obtained.

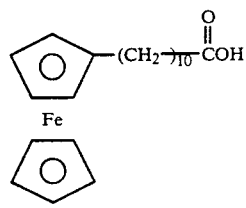

EXAMPLE 23

Figure 25:
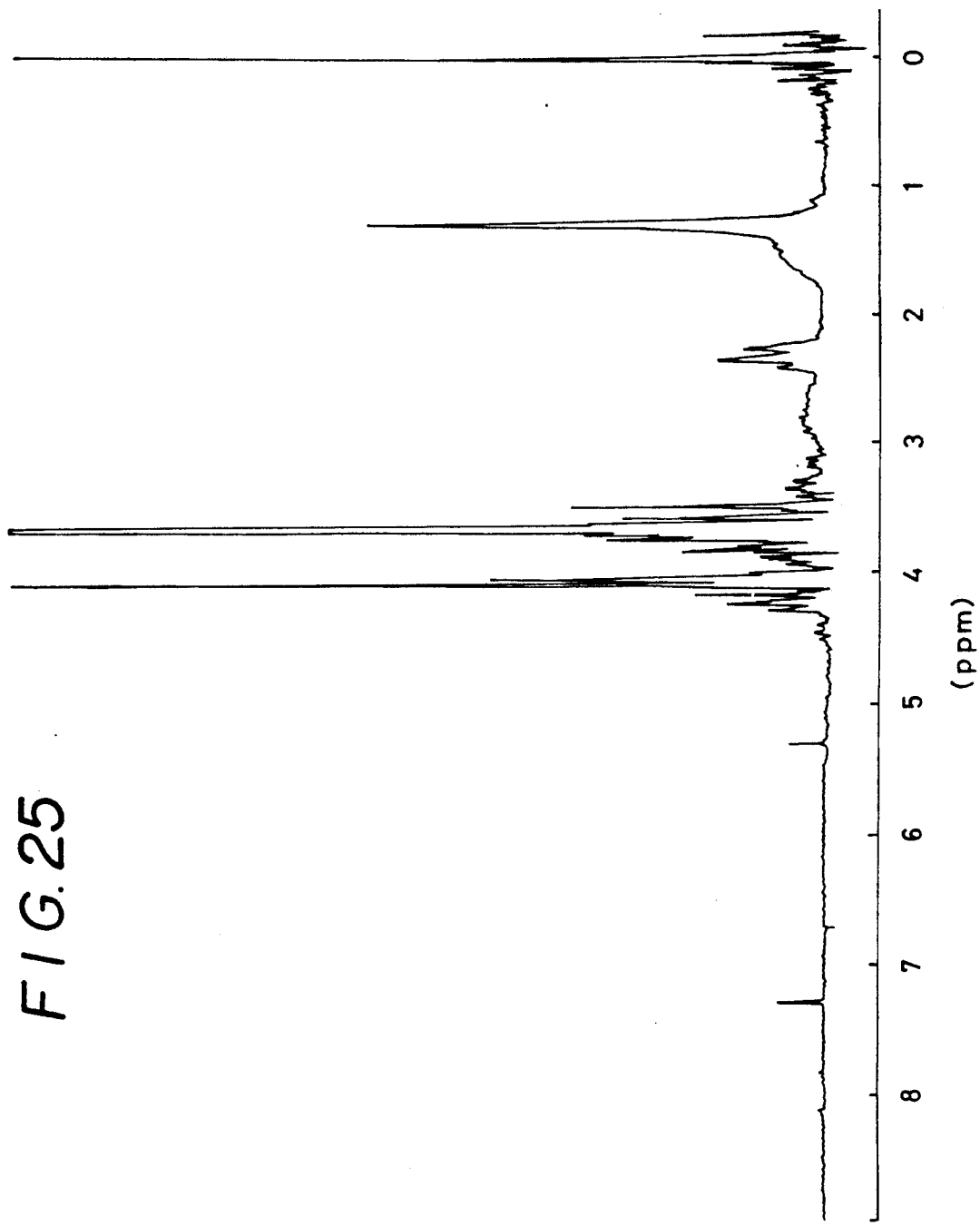
FIG. 25 is a $^1$H-NMR spectrum of the ferrocene derivative obtained in Example 23.

The procedure of Example 5 was repeated with the exception that 39.14 g of polyethylene glycol (average molecular weight, 600) and 0.1 cc of concentrated sulfuric acid were added to 3.02 g of ferrocenylundecanic acid obtained in Preparation Example 23, and reacted at 80° C. for 6 hours. For the purified product obtained, the yield was 51.5% and the amount was 4.00 g. The results of $^1$H-NMR measurement were as shown in FIG. 25. Elemental analytical values were as follows:

| Carbon | Hydrogen | Nitrogen (%) |
|---|---|---|
| 61.03 | 8.68 | 0.00 |
| 59.82 | 8.71 | 0.00 (Calculated) |

From the above results, it can be seen that the above purified product was a ferrocene derivative having the following structure.

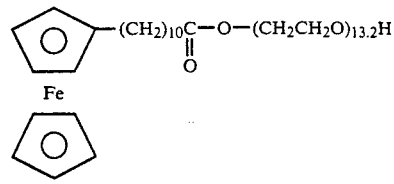

PREPARATION EXAMPLE 24

(1) In the same manner as in Preparation Example 7 (1) except that in place of 11-ethoxycarbonylundecanic acid chloride shown in Preparation Example 7 (1), 19.3 g of 9-ethoxycarbonylnonanic acid chloride was used, and 10.4 g of anhydrous aluminum chloride was used and reacted with 14.0 of ferrocene; 23.4 g of ethyl ferrocenoylnonanate represented by the formula shown below was obtained.

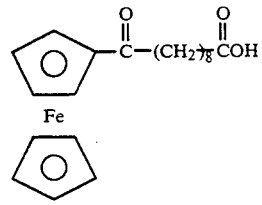

(2) In the same manner as in Preparation Example 7 (2) except that in place of ethyl ferrocenoylundecanate shown in Preparation Example 7 (2), 20.5 g of ethyl ferrocenoylnonanate (obtained in (1) above) was used, and 5.1 g of potassium hydroxide was used; 19.7 g of ferrocenoylnonanic acid represented by the formula shown below was obtained.

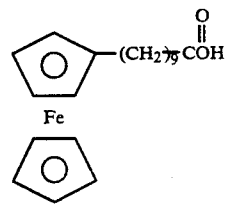

(3) In the same manner as in Preparation Example 7 (3) except that in place of ferrocenoylundecanic acid shown in Preparation Example 7 (3), 11.1 g of ferronoylnonanic acid (obtained in (2) above) was used, and 13.1 g of zinc and 5.5 g of mercuric chloride were used; 8.3 g of ferrocenyldecanic acid represented by the formula shown below was obtained.

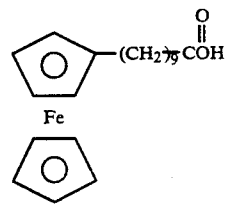

EXAMPLE 24

Figure 26:
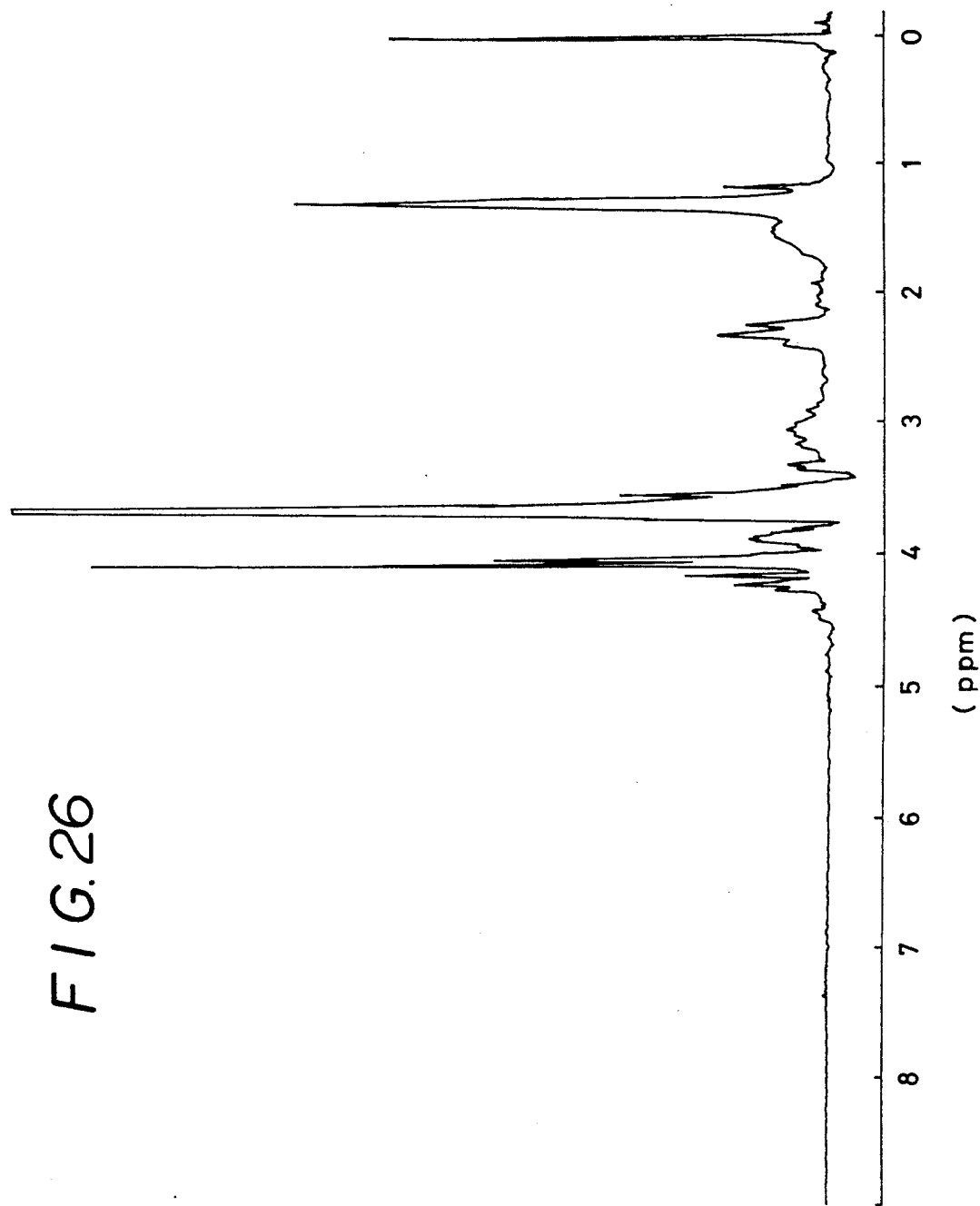
FIG. 26 is a $^1$H-NMR spectrum of the ferrocene derivative obtained in Example 24.

The procedure of Example 5 was repeated with the exception that 82.7 g of polyethylene glycol (average molecular weight, 600) and 0.1 cc of concentrated sulfuric acid were added to 8.19 g of ferrocenyldecanic acid obtained in Preparation Example 24 and reacted at 80° C. for 6 hours. For the purified product obtained, the yield was 49.2% and the amount was 10.60 g. The results of $^1$H-NMR measurement were as shown in FIG. 26. Elemental analytical values were as follows:

| Carbon | Hydrogen | Nitrogen (%) |
|---|---|---|
| 60.02 | 8.63 | 0.00 |
| 59.43 | 8.63 | 0.00 (Calculated) |

From the above results, it can be seen that the above purified product was a ferrocene derivative having the following structure:

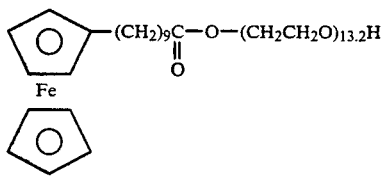

PREPARATION EXAMPLE 25

(1) In the same manner as in Preparation Example 7 (1) except that in place of 11-ethoxycarbonylundecanic acid chloride shown in Preparation Example 7 (1), 29.0 g of 5-ethoxycarbonylvaleric acid chloride was used, and 32.4 g of anhydrous aluminum chloride was used and reacted with 45.2 g of ferrocene; 44.1 g of ethyl ferrocenoylvalerate represented by the formula shown below was obtained.

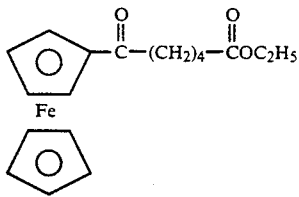

(2) In the same manner as in Preparation Example 7 (2) except that in place of ferrocenoylundecanic acid shown in Preparation Example 7 (2), 44.1 g of ethyl ferrocenoylvalerate (obtained in (1) above), and 13.3 g of potassium hydroxide was used; 36.0 g of ferrocenoylvaleric acid represented by the formula shown below was obtained.

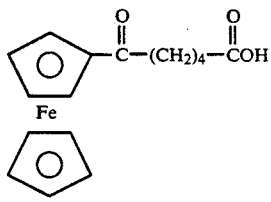

(3) In the same manner as in Preparation Example 7 (3) except that in place of ferrocenoylundecanic acid shown in Preparation Example 7 (3), 9.4 g of ferrocenoylvaleric acid (obtained in (2) above) was used, and 13.1 g of zinc and 5.5 g of mercuric chloride were used; 6.9 g of ferrocenylhexanic acid represented by the formula shown below was obtained.

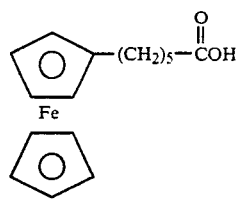

EXAMPLE 25

Figure 27:
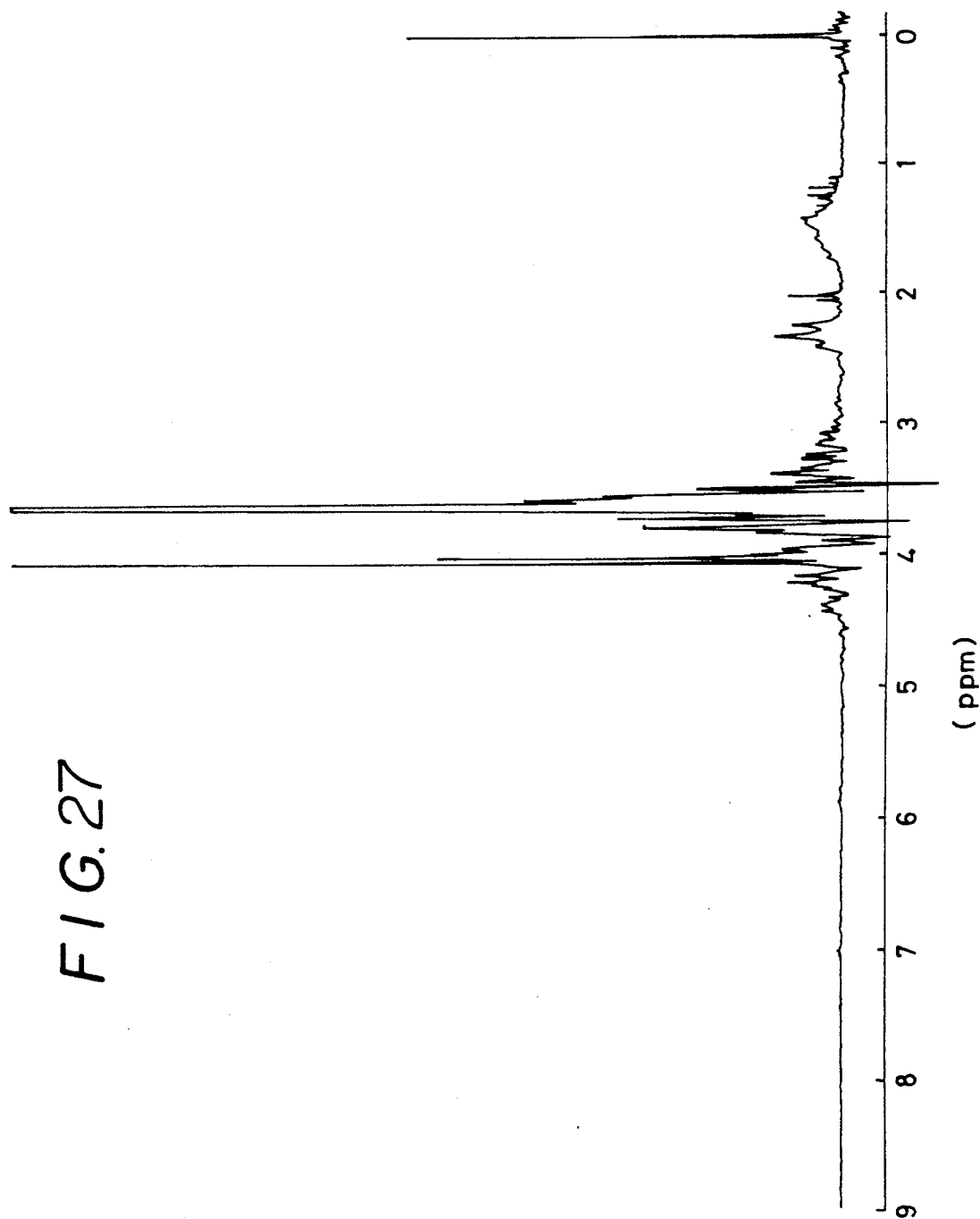
FIG. 27 is a $^1$H-NMR spectrum of the ferrocene derivative obtained in Example 25.

The procedure of Example 5 was repeated with the exception that 184.80 g of polyethylene glycol (average molecular weight, 1,000) and 0.1 cc of concentrated sulfuric acid were added to 6.90 g of ferrocenylhexanic acid obtained in Preparation Example 25 and reacted at 80° C. for 6 hours. For the purified product obtained, the yield was 39.5% and the amount was 11.68 g. The results of $^1$H-NMR measurement were as shown in FIG. 27. Elemental analytical values were as follows:

| Carbon | Hydrogen | Nitrogen (%) |
|---|---|---|
| 56.25 | 9.38 | 0.00 |
| 56.85 | 9.40 | 0.00 (Calculated) |

From the above results, it can be seen that the above purified product was a ferrocene derivative having the following structure:

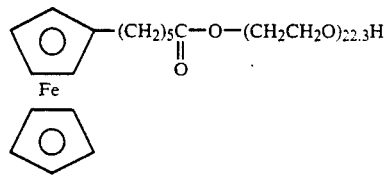

PREPARATION EXAMPLE 26

(1) In the same manner as in Preparation Example 7 (1) except that 16.0 g of octamethylferrocene (known as described in Chem. Ztg., 1976, 100 (3), 143 (Ger)) was used in place of ferrocene shown in Preparation Example 7 (1), 13.3 g of 9-ethoxycarbonylnonanic acid chloride was used in place of 11-ethoxycarbonylundecanic acid chloride, and further 7.2 g of anhydrous aluminum chloride was used and reacted with 16.1 g of ferrocene; 6.4 g of ethyl octamethylferrocenoylnonanate represented by the formula shown below was obtained.

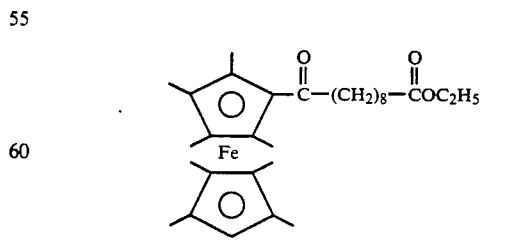

(2) In the same manner as in Preparation Example 7 (2) except that in place of ethyl ferrocenoylundecanate shown in Preparation Example 7 (2), 6.4 g of ethyl octamethylferrocenoylnonanate (obtained in (1) above)

was used, and 1.1 g of potassium hydroxide was used; 6.0 g of octamethylferrocenoylnonanic acid represented by the formula shown below was obtained.

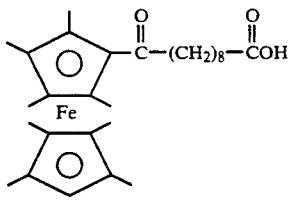

(3) In the same manner as in Preparation Example 7 (3) except that in place of ferrocenoylundecanic acid shown in Preparation Example 7 (3), 6.0 g of octamethylferrocenoylnonanic acid (obtained in (2) above) was used, and 8.1 g of zinc and 3.3 g of mercuric chloride were used; 2.1 g of octamethylferrocenyldecanic acid represented by the formula shown below was obtained.

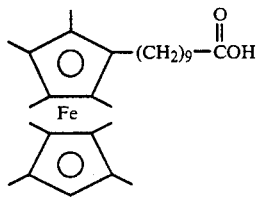

EXAMPLE 26

Figure 28:
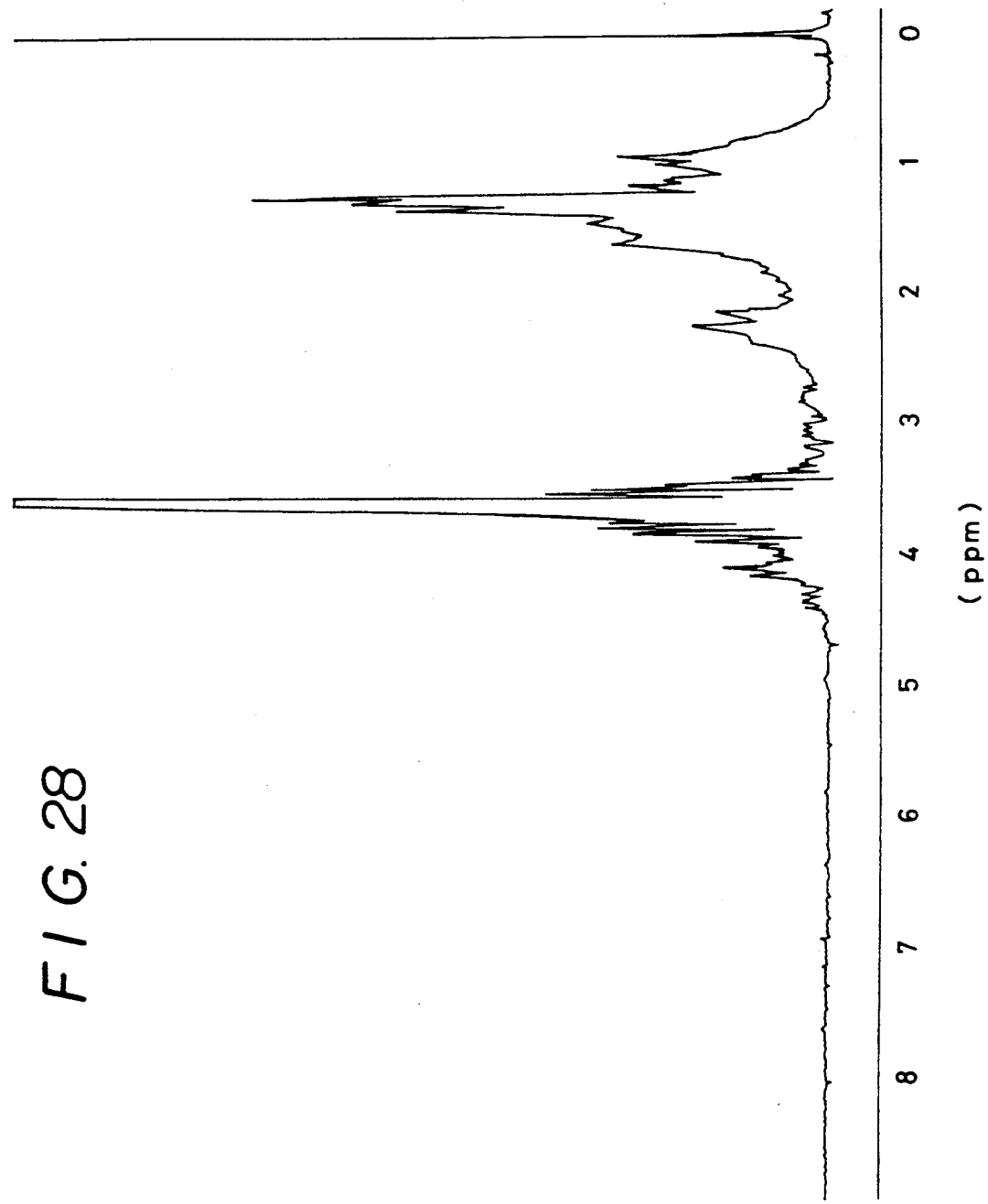
FIG. 28 is a $^1$H-NMR spectrum of the ferrocene derivative obtained in Example 26.

The procedure of Example 5 was repeated with the exception that 86.64 g of polyethylene glycol (average molecular weight, 2,000) and 0.1 cc of concentrated sulfuric acid were added to 2.03 g of octamethylferrocenyldecanic acid obtained in Preparation Example 26 and reacted at 80° C. for 6 hours. For the purified product obtained, the yield was 15.2% and the amount was 1.61 g. The results $^1$H-NMR measurement were as shown in FIG. 28. Elemental analytical values were as follows:

| Carbon | Hydrogen | Nitrogen (%) |
|---|---|---|
| 58.51 | 9.23 | 0.00 |
| 57.84 | 9.15 | 0.00 (Calculated) |

From the above results, it can be seen that the above purified product was a ferrocene derivative having the following structure.

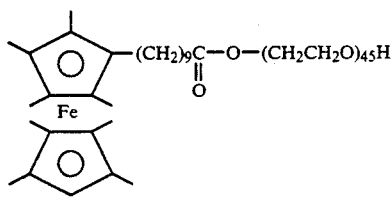

EXAMPLE 27

Figure 29:
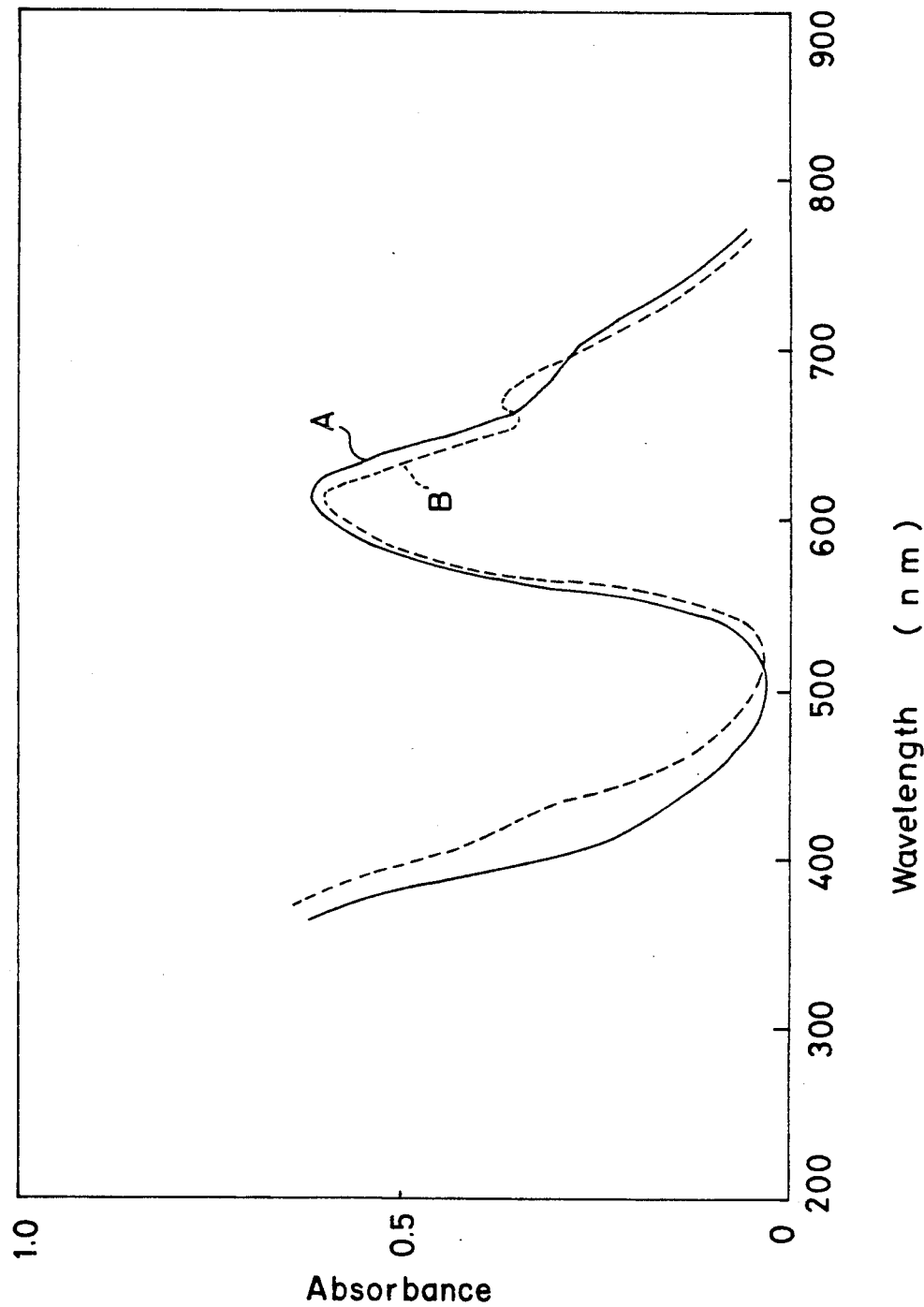
FIG. 29 indicates a visible absorption spectrum of the supernatant obtained in Example 27 and a visible absorption spectrum of the coloring matter thin film on ITO.

An amount of 0.193 g of the ferrocene derivative obtained in Example 7 was added to 100 cc of water as a surfactant (micelle forming agent), and 100 mg of phthalocyanine was added thereto and dispersed or dissolved by stirring for 10 minutes with supersonic waves. The mixture was further stirred for two days and nights with a stirrer, and then the micelle solution (dispersed solution) thus obtained was subjected to centrifugal separation at 2,000 rpm for 30 minutes. A visible absorption spectrum of the supernatant obtained is shown in FIG. 29 (Curve A). This confirmed that phthalocyanine was soluble (dispersed) in the micelle solution. The solubility was phthalocyanine 6.4 mM/2 mM micelle forming agent solution. To this solution, LiBr as a supporting salt was added in such a manner that the concentration was 0.1M and stirred for 10 minutes with a stirrer.

Using the obtained solution as an electrolyte, and an ITO transparent glass electrode as an anode, platinum as a cathode and a saturated calomel electrode as a reference electrode, constant electric potential electrolysis of applied voltage 0.5 V and current density 45 $\mu$A/cm$^2$ was carried out at 25° C. for 30 minutes. The amount of electricity passed in this case was 0.09 coulomb.

As a result, a thin film of phthalocyanine was obtained on the ITO transparent glass electrode. A visible absorption spectrum of phthalocyanine on the ITO transparent glass electrode is shown in FIG. 29 (Curve B). By agreement of FIG. 29 (Curve A) with FIG. 29 (Curve B), it was confirmed that the thin film on the ITO transparent glass electrode was phthalocyanine. An ultraviolet (UV) absorption spectrum showed that the thickness of the thin film was 0.31 $\mu$m.

Figure 36:
FIG. 36 is an SEM photograph illustrating the surface structure of the thin film formed in Example 27.

An SEM photograph (magnification: 30,000; using JSM-T220 produced by Nippon Denshi Co., Ltd.) of the thin film obtained is shown in FIG. 36.

EXAMPLE 28

Figure 30:
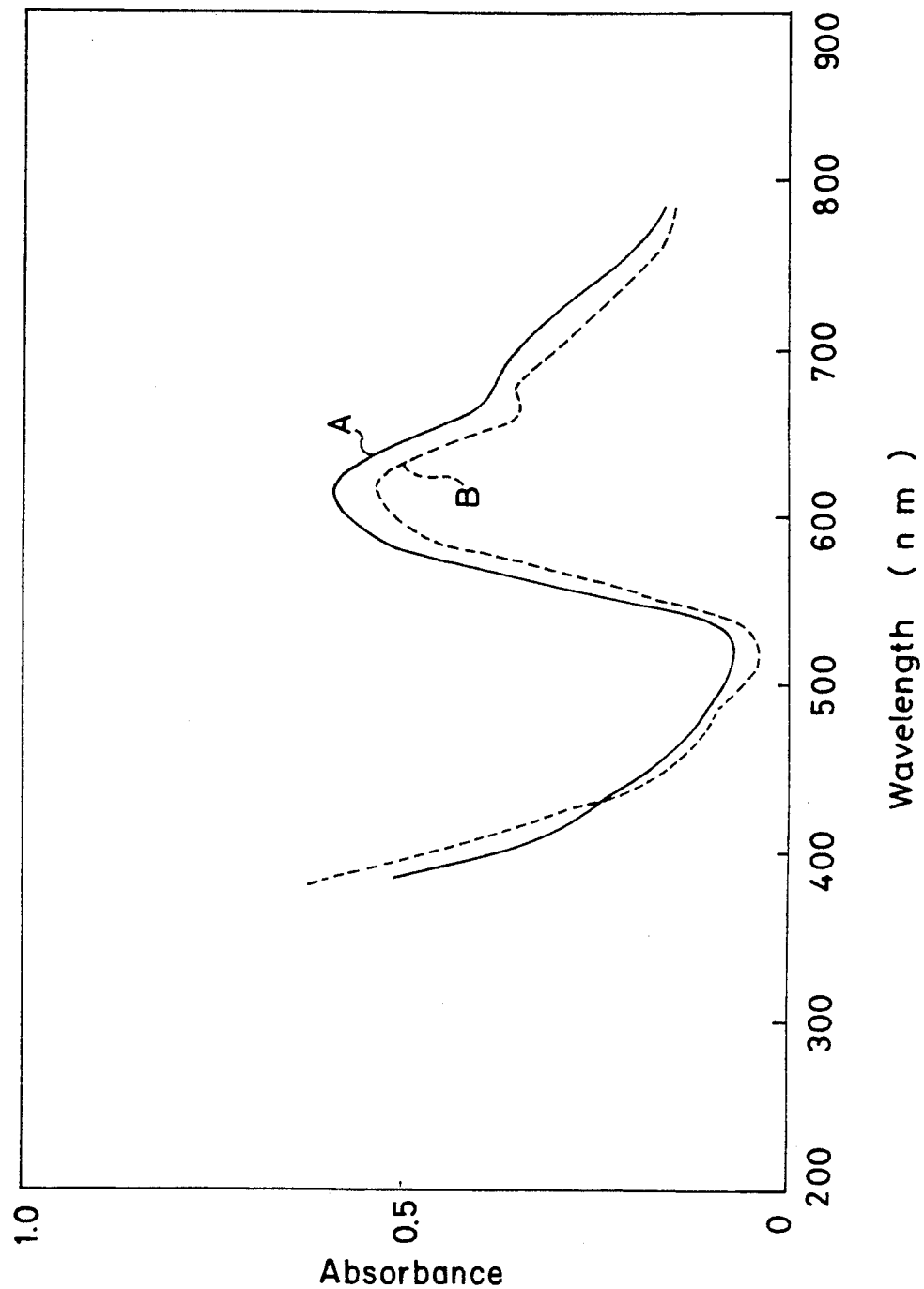
FIG. 30 indicates a visible absorption spectrum of the supernatant obtained in Example 28 and a visible absorption spectrum of the coloring matter thin film on ITO.

An amount of 0.190 g of the ferrocene derivative obtained in Example 23 was added to 100 cc of water as a surfactant (micelle forming agent), and 100 mg of phthalocyanine was added thereto and dispersed or dissolved by stirring for 10 minutes with supersonic waves. The mixture was further stirred for two days and nights with a stirrer, and then the micelle solution (dispersed solution) thus obtained was subjected to centrifugal separation at 2,000 rpm for 30 minutes. A visible absorption spectrum of the supernatant obtained is shown in FIG. 30 (Curve A). This confirmed that phthalocyanine was soluble (dispersed) in the micelle solution. The solubility was phthalocyanine 7.8 mM/2 mM micelle forming agent solution. To this solution, LiBr as a supporting salt was added in such a manner that the concentration was 0.1M and stirred for 10 minutes with a stirrer.

Using the obtained solution as an electrolyte, and an ITO transparent glass electrode as an anode, platinum as a cathode and a saturated calomel electrode as a reference electrode, constant electric potential electrolysis of applied voltage 0.5 V and current density 48 $\mu$A/cm$^2$ was carried out at 25° C. for 30 minutes. The amount of electricity passed in this case was 0.09 coulomb.

As a result, a thin film of phthalocyanine was obtained on the ITO transparent glass electrode. A visible absorption spectrum of phthalocyanine on the ITO transparent glass electrode is shown in FIG. 30 (Curve B). By agreement of FIG. 30 (Curve A) with FIG. 30 (Curve B), it was confirmed that the thin film on the ITO transparent glass electrode was phthalocyanine.

An UV absorption spectrum showed that the thickness of the thin film was 1.05 μm.

Figure 37:
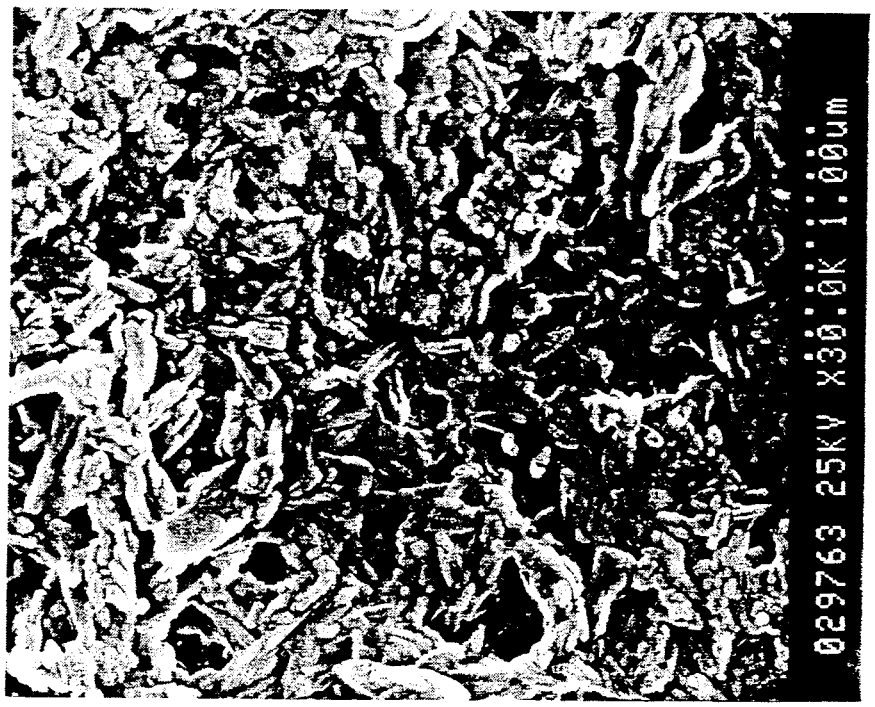
FIG. 37 is an SEM photograph illustrating the surface structure of the thin film formed in Example 28.

An SEM photograph (magnification: 30,000; using JSM-T220 produced by Nippon Denshi Co., Ltd.) of the thin film obtained is shown in FIG. 37.

EXAMPLE 29

Figure 31:
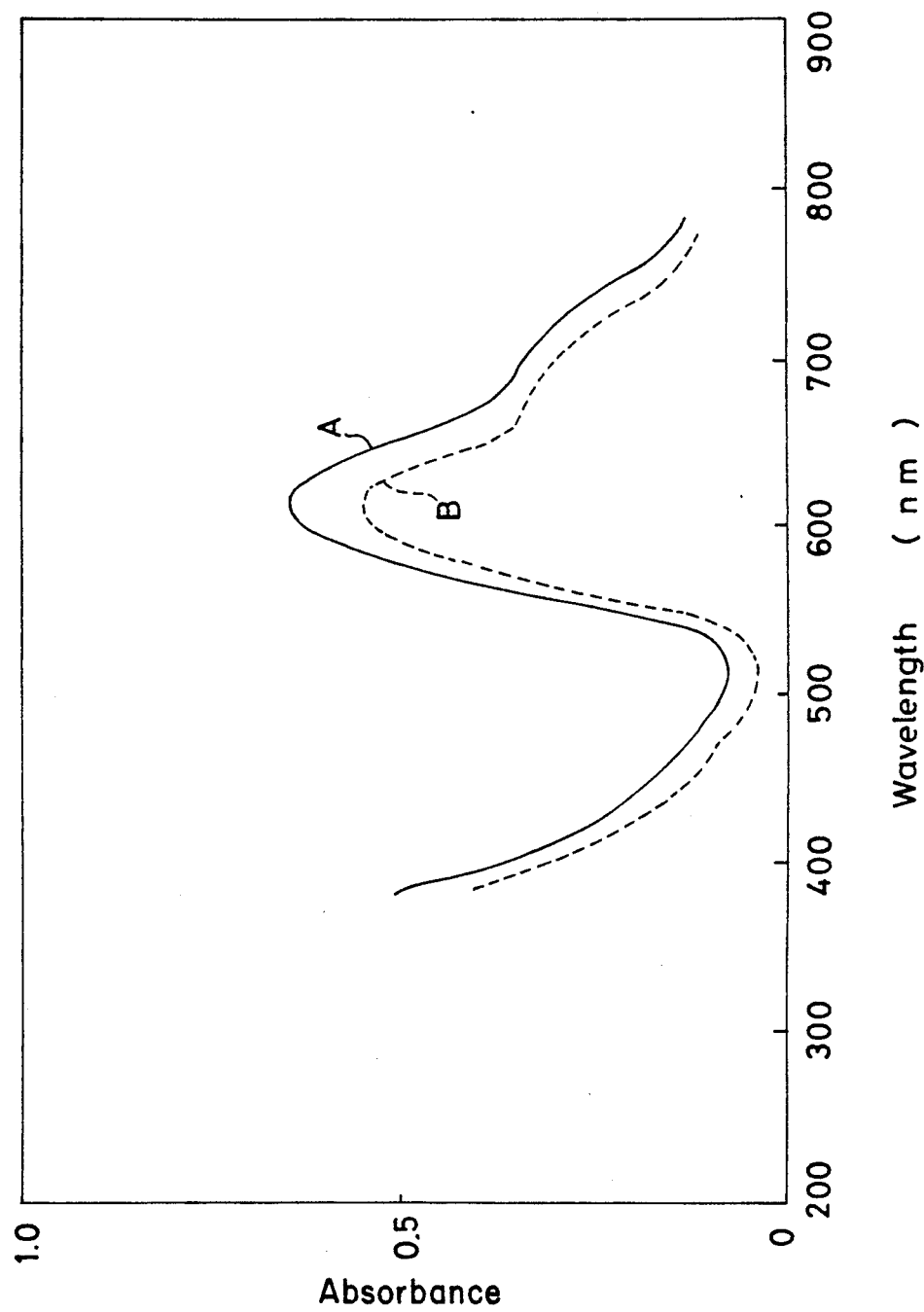
FIG. 31 indicates a visible absorption spectrum of the supernatant obtained in Example 29 and a visible absorption spectrum of the coloring matter thin film on ITO.

An amount of 0.187 g of the ferrocene derivative obtained in Example 24 was added to 100 cc of water as a surfactant (micelle forming agent), and 100 mg of phthalocyanine was added thereto and dispersed or dissolved by stirring for 10 minutes with supersonic waves. The mixture was further stirred for two days and nights with a stirrer, and then the micelle solution (dispersed solution) thus obtained was subjected to centrifugal separation at 2,000 rpm for 30 minutes. A visible absorption spectrum of the supernatant obtained is shown in FIG. 31 (Curve A). This confirmed that phthalocyanine was soluble (dispersed) in the micelle solution. The solubility was phthalocyanine 8.2 mM/2 mM micelle forming agent solution. To this solution, LiBr as a supporting salt was added in such a manner that the concentration was 0.1M and stirred for 10 minutes with a stirrer.

Using the obtained solution as an electrolyte, and an ITO transparent glass electrode as an anode, platinum as a cathode and a saturated calomel electrode as a reference electrode, constant electric potential electrolysis of applied voltage 0.5 V and current density 72 μA/cm$^2$ was carried out at 25° C. for 30 minutes. The amount of electricity passed in this case was 0.13 coulomb.

As a result, a thin film of phthalocyanine was obtained on the ITO transparent glass electrode. A visible absorption spectrum of phthalocyanine on the ITO transparent glass electrode is shown in FIG. 31 (Curve B). By agreement of FIG. 31 (Curve A) with FIG. 31 (Curve B), it was confirmed that the thin film on the ITO transparent glass electrode was phthalocyanine. An UV absorption spectrum showed that the thickness of the thin film was 1.85 μm.

Figure 38:
FIG. 38 is an SEM photograph illustrating the surface structure of the thin film formed in Example 29.

An SEM photograph (magnification: 30,000; using JSM-T220 produced by Nippon Denshi Co., Ltd.) of the thin film obtained is shown in FIG. 38.

EXAMPLE 30

Figure 32:
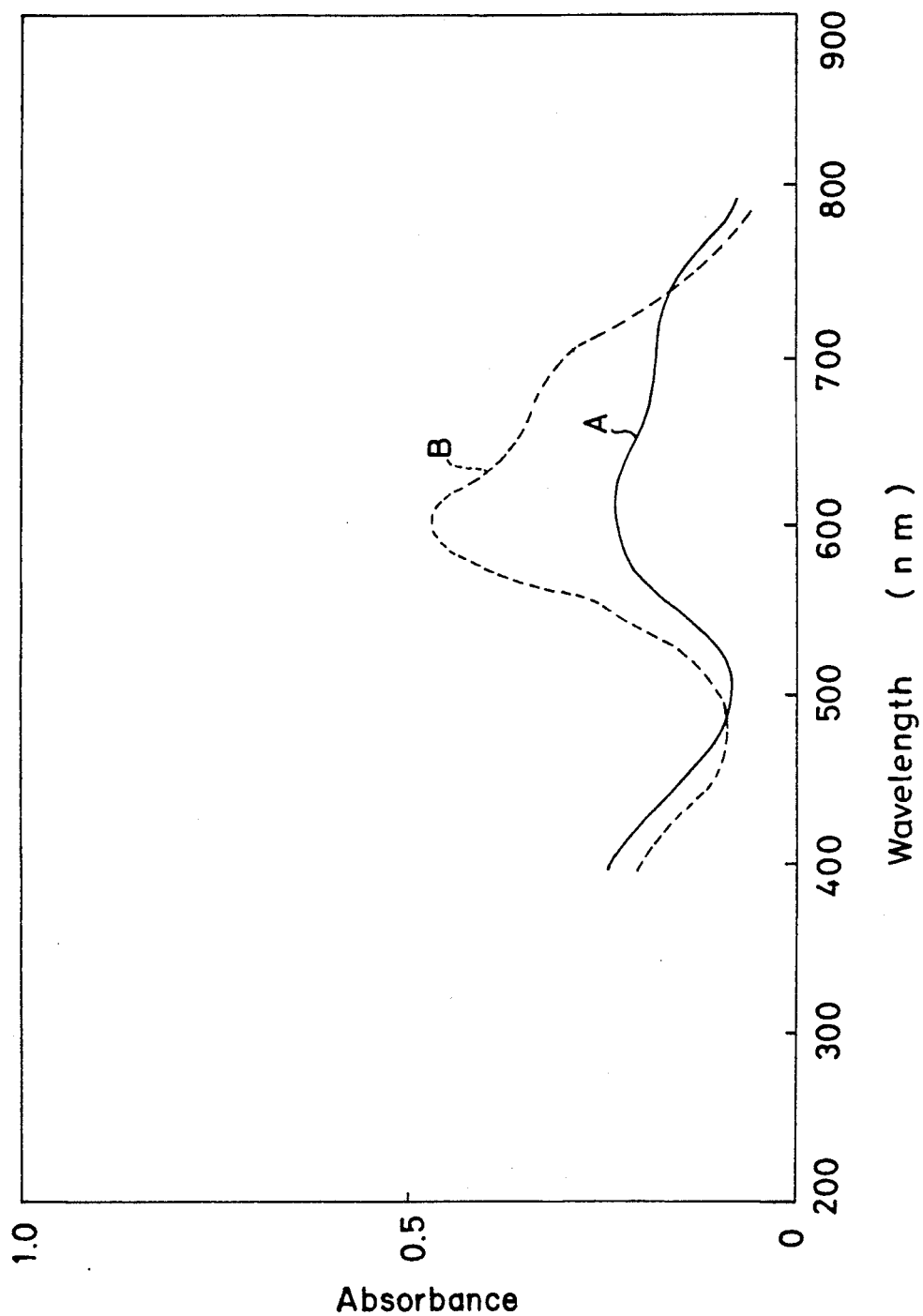
FIG. 32 indicates a visible absorption spectrum of the supernatant obtained in Example 30 and a visible absorption spectrum of the coloring matter thin film on ITO.

An amount of 0.176 g of the ferrocene derivative obtained in Example 25 was added to 100 cc of water as a surfactant (micelle forming agent), and 100 mg of phthalocyanine was added thereto and dispersed or dissolved by stirring for 10 minutes with supersonic waves. The mixture was further stirred for two days and nights with a stirrer, and then the micelle solution (dispersed solution) thus obtained was subjected to centrifugal separation at 2,000 rpm for 30 minutes. A visible absorption spectrum of the supernatant obtained is shown in FIG. 32 (Curve A). This confirmed that phthalocyanine was soluble (dispersed) in the micelle solution. The solubility was phthalocyanine 1.8 mM/2 mM micelle forming agent solution. To this solution, LiBr as a supporting salt was added in such a manner that the concentration was 0.1M and stirred for 10 minutes with a stirrer.

Using the obtained solution as an electrolyte, and an ITO transparent glass electrode as an anode, platinum as a cathode and a saturated calomel electrode as a reference electrode, constant electric potential electrolysis of applied voltage 0.5 V and current density 17 μA/cm$^2$ was carried out at 25° C. for 30 minutes. The amount of electricity passed in this case was 0.04 coulomb.

As a result, a thin film of phthalocyanine was obtained on the ITO transparent glass electrode. A visible absorption spectrum of phthalocyanine on the ITO transparent glass electrode is shown in FIG. 32 (Curve B). By agreement of FIG. 32 (Curve A) with FIG. 32 (Curve B), it was confirmed that the thin film on the ITO transparent glass electrode was phthalocyanine. An UV absorption spectrum showed that the thickness of the thin film was 0.04 μm.

EXAMPLE 31

Figure 33:
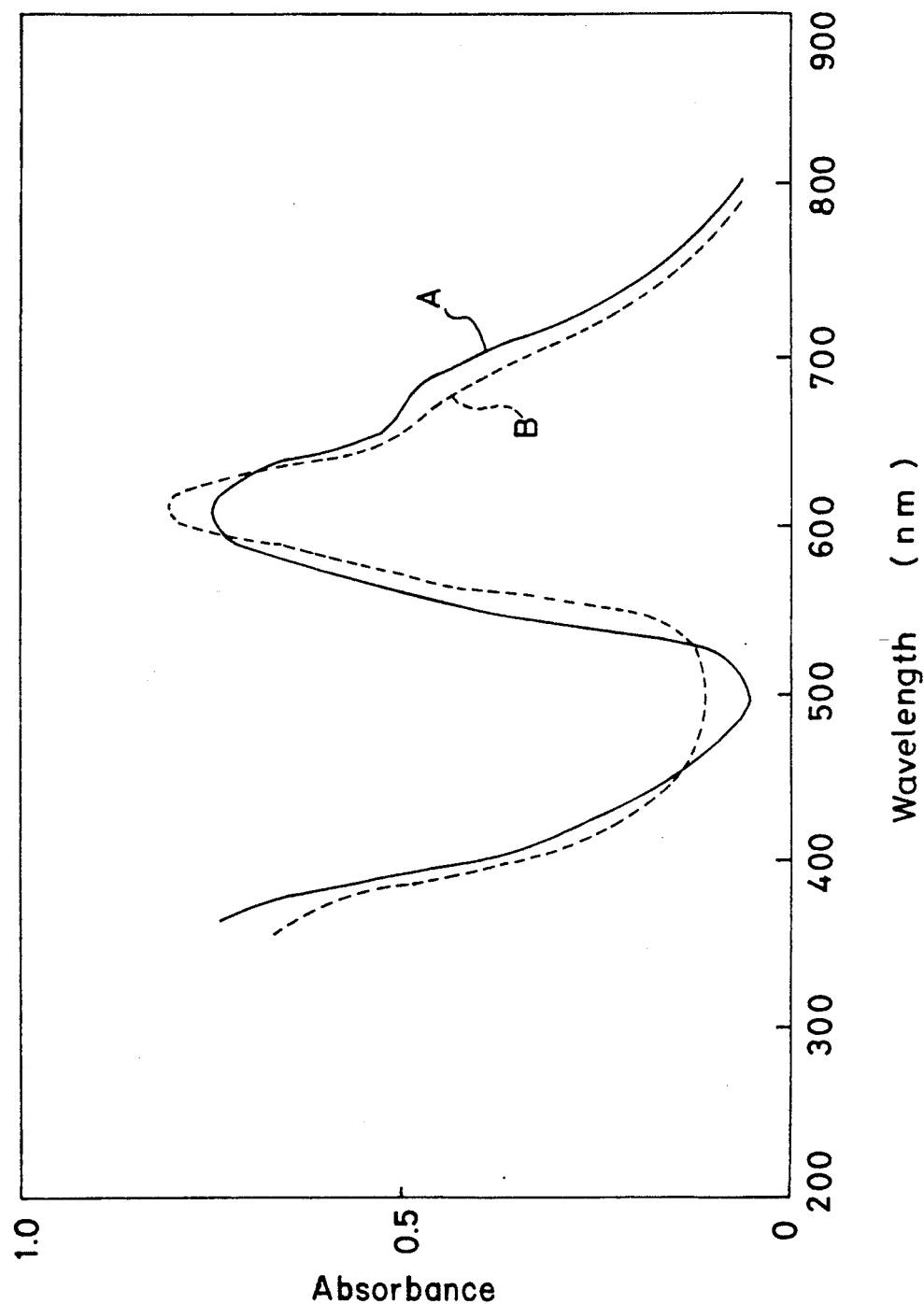
FIG. 33 indicates a visible absorption spectrum of the supernatant obtained in Example 31 and a visible absorption spectrum of the coloring matter thin film on ITO.

An amount of 0.210 g of the ferrocene derivative obtained in Example 26 was added to 100 cc of water as a surfactant (micelle forming agent), and 100 mg of phthalocyanine was added thereto and dispersed or dissolved by stirring for 10 minutes with supersonic waves. The mixture was further stirred for two days and nights with a stirrer, and then the micelle solution (dispersed solution) thus obtained was subjected to centrifugal separation at 2,000 rpm for 30 minutes. A visible absorption spectrum of the supernatant obtained is shown in FIG. 33 (Curve A). This confirmed that phthalocyanine was soluble (dispersed) in the micelle solution. The solubility was phthalocyanine 4.0 mM/2 mM micelle forming agent solution. To this solution, LiBr as a supporting salt was added in such a manner that the concentration was 0.1M and stirred for 10 minutes with a stirrer.

Using the obtained solution as an electrolyte, and an ITO transparent glass electrode as an anode, platinum as a cathode and a saturated calomel electrode as a reference electrode, constant electric potential electrolysis of applied voltage 0.5 V and current density 124 μA/cm$^2$ was carried out at 25° C. for 30 minutes. The amount of electricity passed in this case was 0.23 coulomb.

As a result, a thin film of phthalocyanine was obtained on the ITO transparent glass electrode. A visible absorption spectrum of phthalocyanine on the ITO transparent glass electrode is shown in FIG. 33 (Curve B). By agreement of FIG. 33 (Curve A) with FIG. 33 (Curve B), it was confirmed that the thin film on the ITO transparent glass electrode was phthalocyanine. An UV absorption spectrum showed that the thickness of the thin film was 4.6 μm.

EXAMPLE 32

Figure 34:
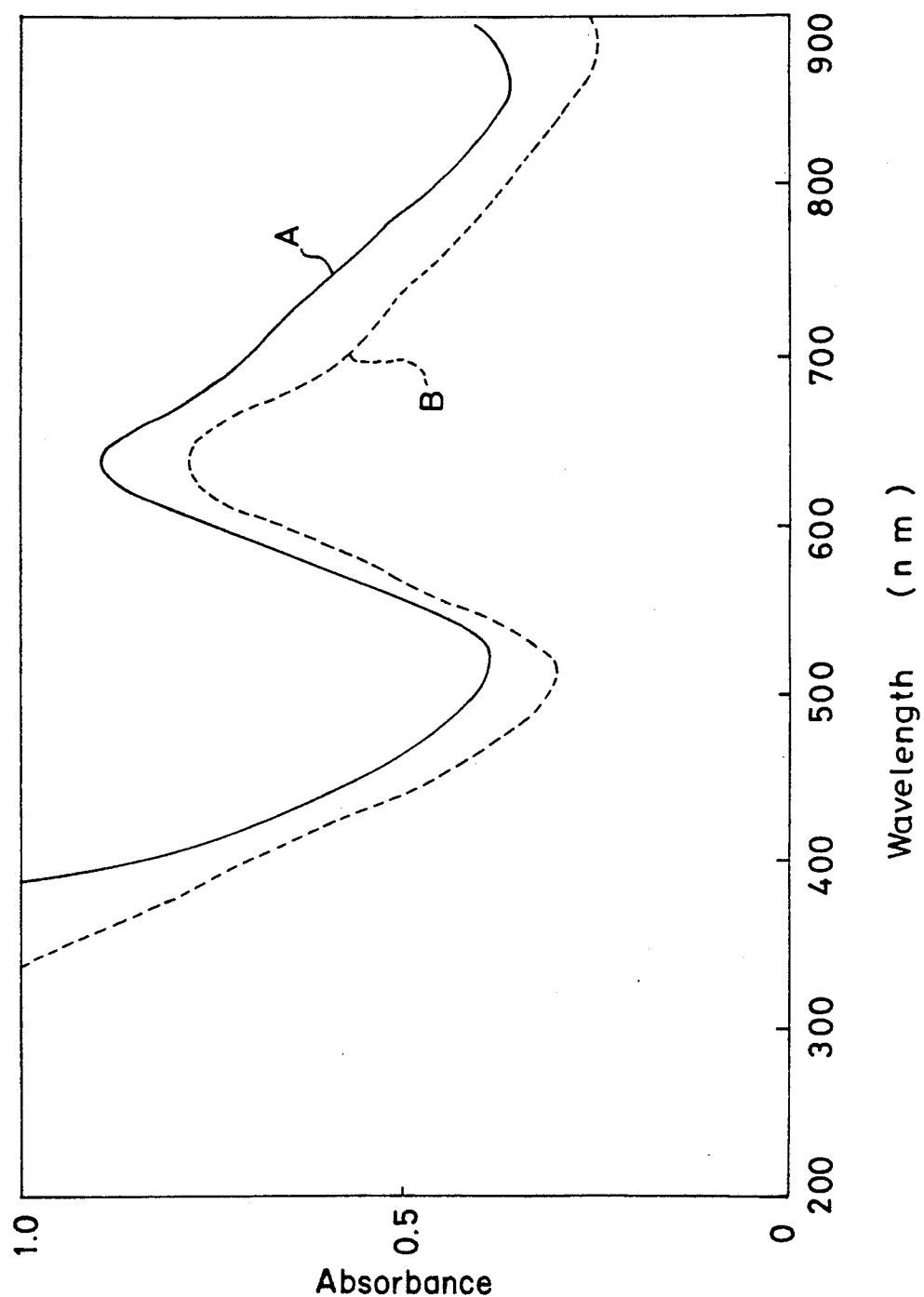
FIG. 34 indicates a visible absorption spectrum of the supernatant obtained in Example 32 and a visible absorption spectrum of the coloring matter thin film on ITO.

An amount of 0.188 g of the ferrocene derivative obtained in Example 5 was added to 100 cc of water as a surfactant (micelle forming agent), and 100 mg of phthalocyanine iron complex was added and dispersed or dissolved by stirring for 10 minutes with supersonic waves. The mixture was further stirred for two days and nights with a stirrer, and then the micelle solution (dispersed solution) thus obtained was subjected to centrifugal separation at 2,000 rpm for 30 minutes. A visible absorption spectrum of the supernatant obtained is shown in FIG. 34 (Curve A). This confirmed that the phthalocyanine iron complex was soluble (dispersed) in the micelle solution. The solubility was phthalocyanine iron complex 4.1 mM/2 mM micelle forming agent solution. To this solution, LiBr as a supporting salt was added in such a manner that the concentration was 0.1M and stirred for 10 minutes with a stirrer.

Using the obtained solution as an electrolyte, and an ITO transparent glass electrode as an anode, platinum as a cathode and a saturated calomel electrode as a reference electrode, constant electric potential electrolysis of applied voltage 0.5 V and current density 14 μA/cm² was carried out at 25° C. for 30 minutes.

As a result, a thin film of phthalocyanine iron complex was obtained on the ITO transparent glass electrode. A visible absorption spectrum of the phthalocyanine iron complex on the ITO transparent glass electrode is shown in FIG. 34 (Curve B). Because of agreement of FIG. 34 (Curve A) with FIG. 34 (Curve B), it was confirmed that the thin film on the ITO transparent glass electrode was the phthalocyanine iron complex. An UV absorption spectrum showed that the thickness of the thin film was 0.16 μm.

EXAMPLE 33

Figure 35:
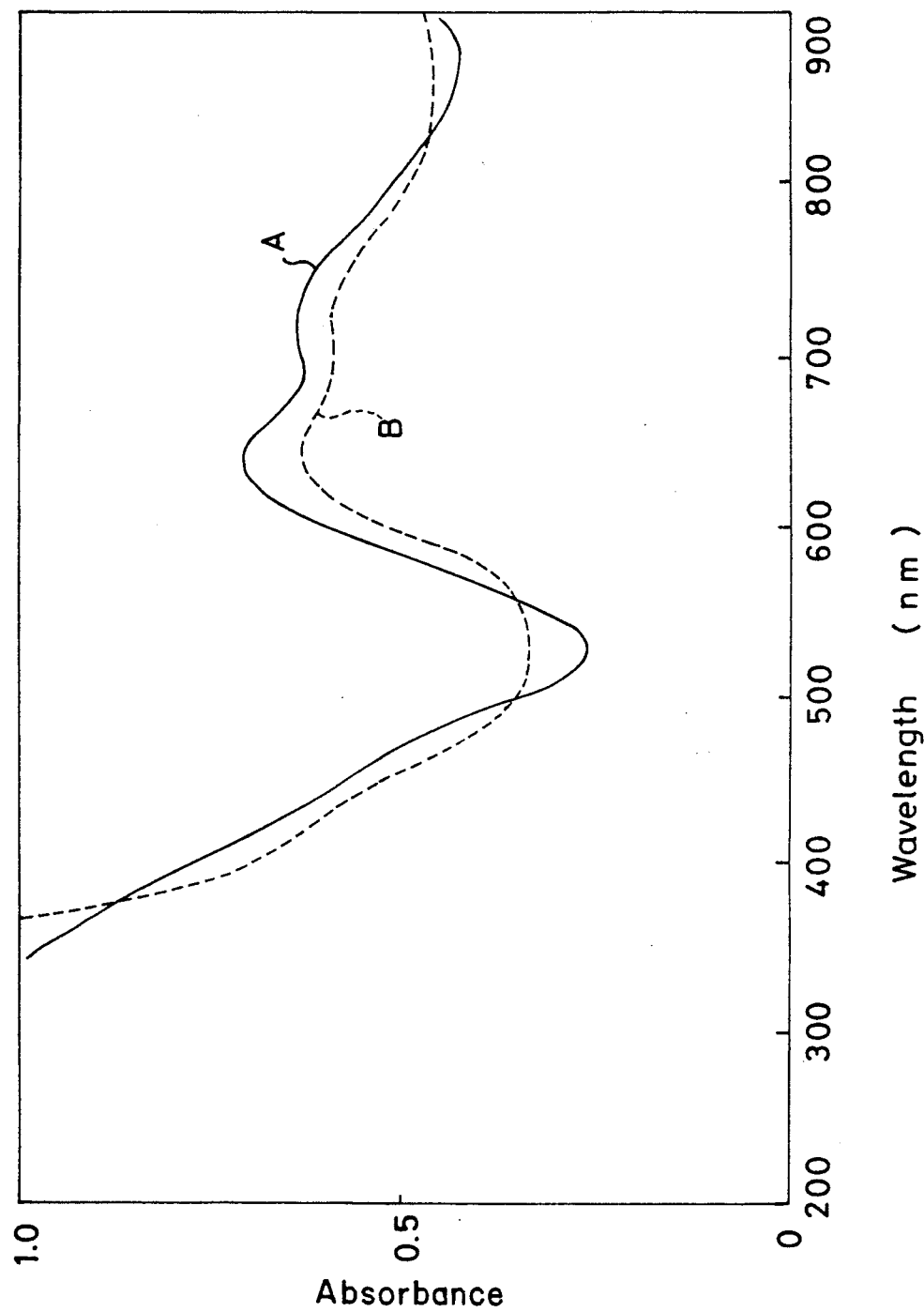
FIG. 35 indicates a visible absorption spectrum of the supernatant obtained in Example 33 and a visible absorption spectrum of the coloring matter thin film on ITO.

An amount of 0.188 g of the ferrocene derivative obtained in Example 5 was added to 100 cc of water as a surfactant (micelle forming agent), and 100 mg of phthalocyanine copper complex was added thereto and dispersed or dissolved by stirring for 10 minutes with supersonic waves. The mixture was further stirred for two days and nights with a stirrer, and then the micelle solution (dispersed solution) thus obtained was subjected to centrifugal separation at 2,000 rpm for 30 minutes. A visible absorption spectrum of the supernatant obtained is shown in FIG. 35 (Curve A). This confirmed that phthalocyanine copper complex was soluble (dispersed) in the micelle solution. The solubility was phthalocyanine copper complex 3.8 mM/2 mM micelle forming agent solution. To this solution, LiBr as a supporting salt was added in such a manner that the concentration was 0.1M and stirred for 10 minutes with a stirrer.

Using the obtained solution as an electrolyte, and an ITO transparent glass electrode as an anode, platinum as a cathode and a saturated calomel electrode as a reference electrode, constant electric potential electrolysis of applied voltage 0.5 V and current density 43 μA/cm² was carried out at 25° C. for 30 minutes. The amount of electricity passed in this case was 0.11 coulomb.

As a result, a thin film of phthalocyanine copper complex was obtained on the ITO transparent glass electrode. A visible absorption spectrum of the phthalocyanine copper complex on the ITO transparent glass electrode is shown in FIG. 35 (Curve B). Because of agreement of FIG. 35 (Curve A) with FIG. 35 (Curve B), it was confirmed that the thin film on the ITO transparent glass electrode was the phthalocyanine copper complex. An UV absorption spectrum showed that the thickness of the thin film was 0.08 μm.

INDUSTRIAL APPLICABILITY

The ferrocene derivatives of the present invention are novel compounds and can be used in various applications, for example, as surfactants, catalysts, auxiliary fuels, depressors, dispersants and the like. The novel ferrocene derivatives, when used as surfactants, form micelles in an aqueous solution system and, therefore, coloring matters such as phthalocyanine, having a wide variety of applications and water-insoluble polymers can be made soluble.

If the process of the present invention is carried out using the novel ferrocene derivatives or other ferrocene derivatives as surfactants (micelle forming agents), an organic thin film greatly small in thickness can be formed by aqueous solution electrolysis and utilizing the gathering or scattering of micelles. This process for production of an organic thin film can be utilized, as well as coating and coloring of various products, in production of electronic materials such as photoconductor materials, solar batteries, secondary batteries, electric power apparatus materials, display device materials and the like, and further in production of light-sensitive materials, insulating materials, light memory materials, light sensor materials, gas sensor materials and the like.

We claim:

1. A ferrocene derivative represented by the general formula:

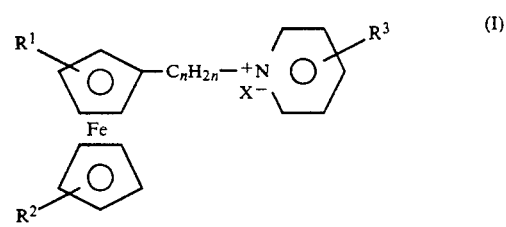

wherein $R^1$ and $R^2$ are each independently a hydrogen, a methyl group, an ethyl group, a methoxy group or a carbomethoxy group, $R^3$ is a hydrogen, a methyl group, an ethyl group, a methoxy group, a carbomethoxy group, a hydroxyl group, carboxyl group or a sulfonic acid group, X is a halogen, and $C_nH_{2n}$ is a straight or branched hydrocarbon group having 4 to 16 carbon atoms; or the general formula:

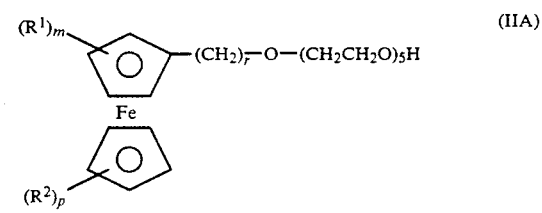

wherein m is an integer of 1 to 4, p is an integer of 1 to 5, r is an integer of 11 to 18, s is a real number of 2.0 to 70, and $R^1$ and $R^2$ are the same as described above; or the general formula:

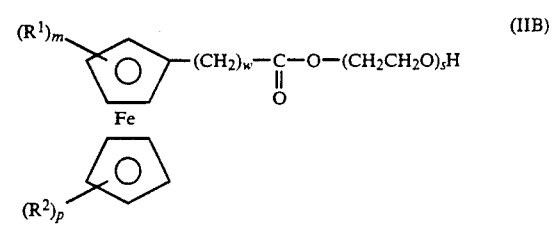

wherein w is an integer of 2 to 18, and m, p, s, $R^1$ and $R^2$ are the same as described above.

2. The ferrocene derivative according to claim 1 of the formula:

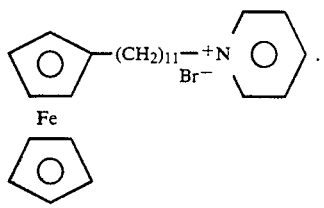

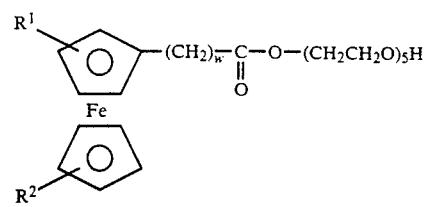

3. The ferrocene derivative according to claim 1 wherein in formula (I), $R^1$, $R^2$ and $R^3$ are independently methyl, ethyl or methoxy groups.

4. The ferrocene derivative according to claim 1 wherein in formula (I), $R^3$ is a carbomethoxy group, carboxyl group or sulfonic acid group.

5. The ferrocene derivative according to claim 1 wherein in formula (I) X is Br.

6. The ferrocene derivative according to claim 1 wherein in formula (I), the group $C_nH_{2n}$ is a tetramethylene group, a pentamethylene group, an octamethylene group, an undecamethylene group, a dodecamethylene group, a hexadecamethylene group, a 2-methylundecamethylene group or a 4-ethylundecamethylene group.

7. The ferrocene derivative according to claim 1 of the formula:

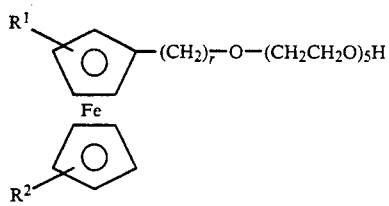

wherein s is a real number from 2 to 50, and r is 11 to 15.

8. The ferrocene derivative according to claim 7 of the formula:

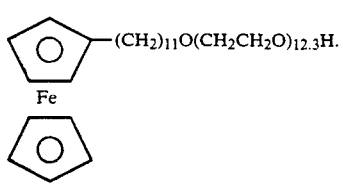

9. The ferrocene derivative according to claim 7 of the formula:

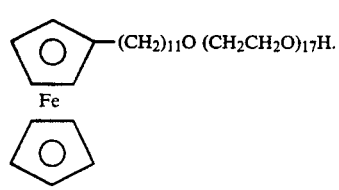

10. The ferrocene derivative according to claim 1 of the formula:

wherein s is a real number from 2 to 50 and w is 7 to 15.

11. The ferrocene derivative according to claim 10 of the formula:

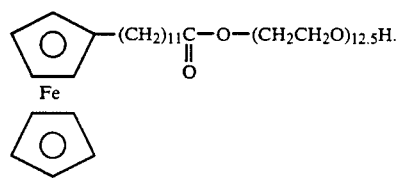

12. The ferrocene derivative according to claim 10 of the formula:

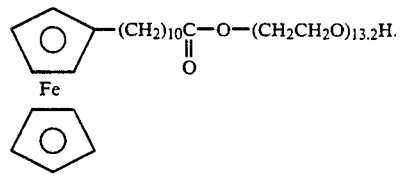

13. The ferrocene derivative according to claim 10 of the formula:

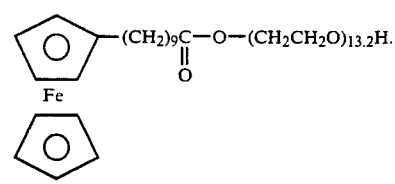

14. The ferrocene derivative according to claim 1 of the formula:

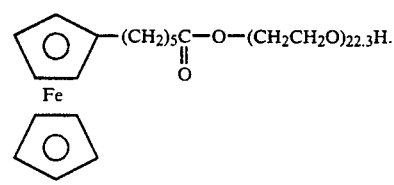

15. The ferrocene derivative according to claim 1 of the formula:

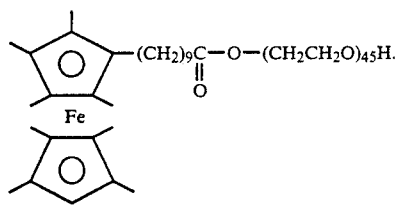

16. A surfactant comprising a ferrocene derivative represented by the general formula:

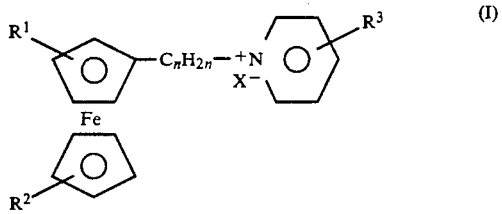

wherein $R^1$ and $R^2$ are each independently a hydrogen, a methyl group an ethyl group, a methoxy group or a carbomethoxy group, $R^3$ is a hydrogen, a methyl group, an ethyl group, a methoxy group, a carbomethoxy group, a hydroxyl group, carboxyl group or a sulfonic acid group, X is a halogen, and $C_nH_{2n}$ is a straight or branched hydrocarbon group having 4 to 16 carbon atoms; or the general formula:

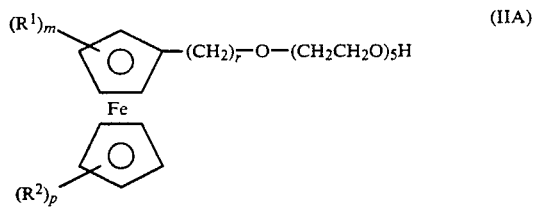

wherein m is an integer of 1 to 4, p is an integer of 1 to 5, r is an integer of 11 to 18, s is a real number of 2.0 to 70, and $R^1$ and $R^2$ are the same as described above, or the general formula:

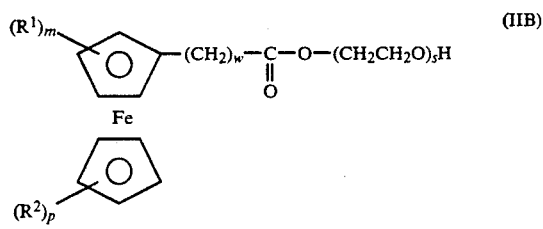

wherein w is an integer of 2 to 18, and m, p, s, $R^1$ and $R^2$ are the same as described above.

17. The surfactant comprising a ferrocene derivative according to claim 16, wherein the ferrocene derivative is of the formula:

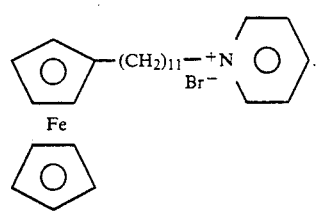

18. The surfactant comprising a ferrocene derivative according to claim 2, wherein in formula (I), $R^1$, $R^2$ and $R^3$ are independently methyl, ethyl or methoxy groups, $R^3$ is a carbomethoxy group, a carboxyl group or a sulfonic acid group, X is Br and $C_nH_{2n}$ is a tetramethylene group, a pentamethylene group, an octamethylene group, an undecamethylene group, a dodecamethylene group, or a hexadecamethylene group.

19. The surfactant comprising a ferrocene derivative according to claim 2, wherein the ferrocene derivative is of the formula:

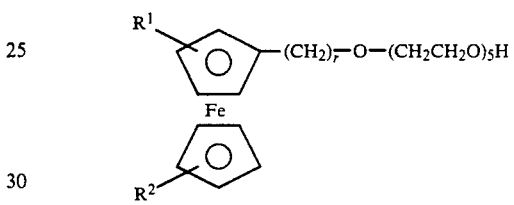

wherein s is a real number from 2 to 50.

20. The surfactant comprising a ferrocene derivative according to claim 19, wherein the ferrocene derivative is of a formula selected from the group consisting of

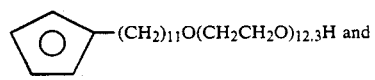

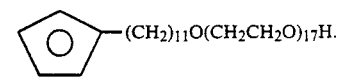

21. The surfactant comprising a ferrocene derivative according to claim 2, wherein the ferrocene derivative is of the formula:

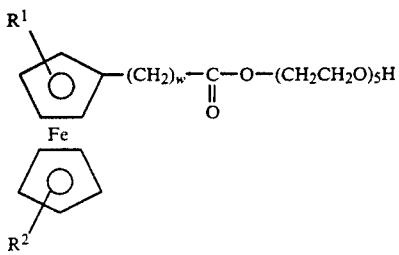

wherein s is a real number from 2 to 50.

22. The surfactant comprising a ferrocene derivative according to claim 21, wherein the ferrocene derivative is of a formula selected from the group consisting of

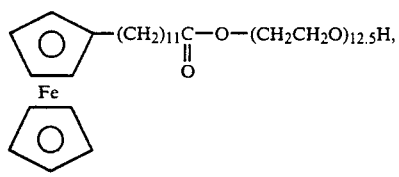

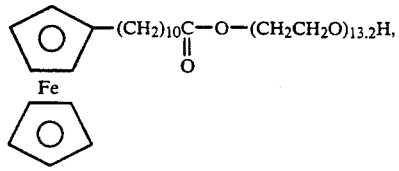

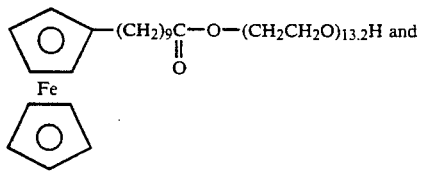

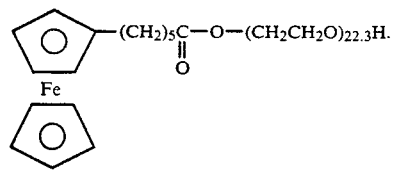

23. The surfactant comprising a ferrocene derivative according to claim 16, wherein the ferrocene derivative is of the formula:

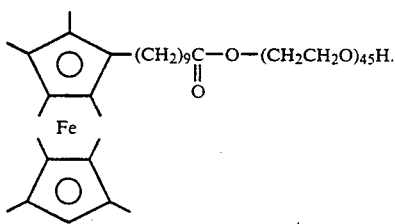

24. A method of producing an organic thin film of a hydrophobic substance comprising:
forming an aqueous phase of (a) the hydrophobic substance and (c) a ferrocene derivative represented by the general formula:

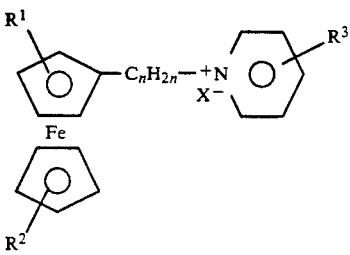

wherein $R^1$ and $R^2$ are each independently a hydrogen, a methyl group an ethyl group, a methoxy group or a carbomethoxy group, $R^3$ is a hydrogen, a methyl group, an ethyl group, a methoxy group, a carbomethoxy group, a hydroxyl group, carboxyl group or a sulfonic acid group, X is a halogen, and $C_nH_{2n}$ is a straight or branched hydrocarbon group having 4 to 16 carbon atoms; or the general formula:

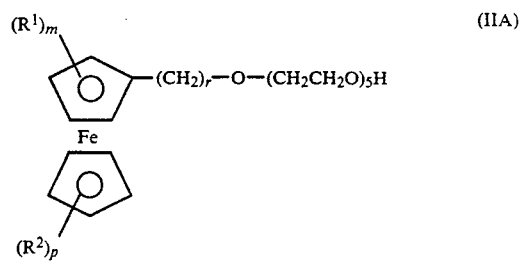

wherein m is an integer of 1 to 4, p is an integer of 1 to 5, r is an integer of 11 to 18, s is a real number of 2.0 to 70, and $R^1$ and $R^2$ are the same as described above; or the general formula:

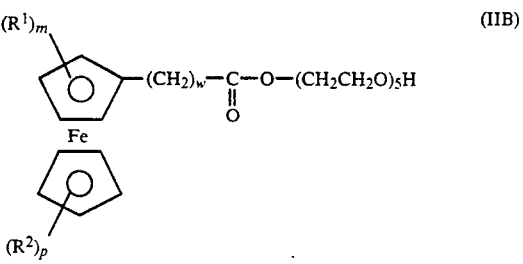

wherein w is an integer of 2 to 18, and m, p, s, $R^1$ and $R^2$ are the same as described above or the general formula:

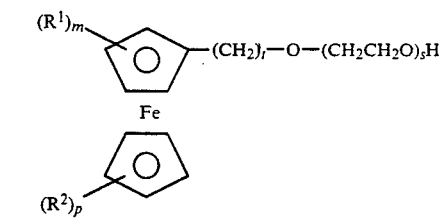

wherein t is an integer of 2 to 10, and $R^1$, $R^2$, m, p and s are the same as above;
providing an electrode in contact with the aqueous phase; and
electrolyzing the aqueous phase to form a thin film of the hydrophobic substance on a surface of the electrode.

25. The method according to claim 24, wherein the electrolyzing is conducted at a temperature of the aqueous phase of 0° to 70° C., a voltage of 0.03 to 1.5 V and a current density of not more than 10 mA/cm².

26. The method according to claim 24 wherein the electrode is of a metal more noble than ferrocene.

27. The method according to claim 26, wherein the electrode is selected from the group consisting of a mixed oxide of indium oxide and tin oxide, platinum, gold, silver, glassy carbon, an electrically conductive metal oxide, and an electrically conductive organic polymer.

28. The method according to claim 24, wherein the electrolyzing is conducted at a temperature of the aqueous phase of 20° to 30° C., a voltage of 0.1 to 0.5 V and a current density of 50 to 300 µA/cm².

29. A method of producing an organic thin film of a hydrophobic substance comprising:

forming an aqueous phase of (a) the hydrophobic substance, (b) a salt and (c) a ferrocene derivative represented by the general formula:

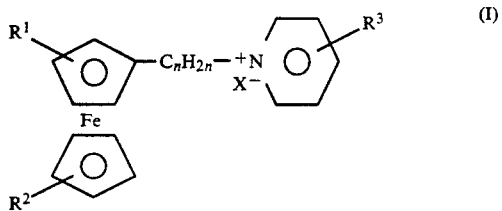

wherein $R^1$ and $R^2$ are each independently a hydrogen, a methyl group an ethyl group, a methoxy group or a carbomethoxy group, $R^3$ is a hydrogen, a methyl group, an ethyl group, a methoxy group, a carbomethoxy group, a hydroxyl group, carboxyl group or a sulfonic acid group, X is a halogen, and $C_nH_{2n}$ is a straight or branched hydrocarbon group having 4 to 16 carbon atoms; or the general formula:

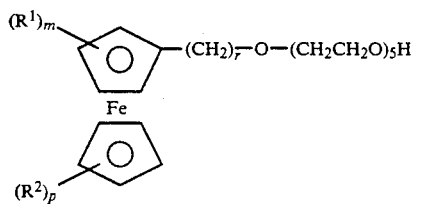

wherein m is an integer of 1 to 4, p is an integer of 1 to 5, r is an integer of 11 to 18, s is a real number of 2.0 to 70, and $R^1$ and $R^2$ are the same as described above; or the general formula:

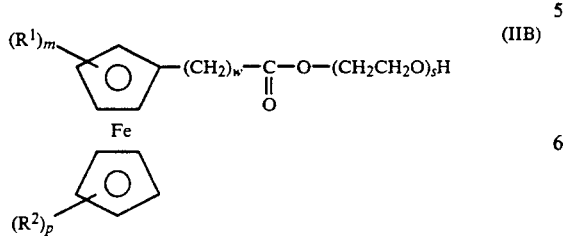

wherein w is an integer of 2 to 18, and m, p, s, $R^1$ and $R^2$ are the same as described above or the general formula:

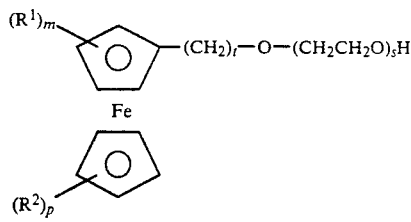

wherein t is an integer of 2 to 10, and $R^1$, $R^2$, m, p and s are the same as above;

providing an electrode in contact with the aqueous phase; and electrolyzing the aqueous phase to form a thin film of the hydrophobic substance on a surface of the electrode.

30. The method according to claim 29, wherein the electrolyzing is conducted at a temperature of the aqueous phase of 0° to 70° C., a voltage of 0.03 to 1.5 V and a current density of not more than 10 mA/cm².

31. The method according to claim 29 wherein the electrode is of a metal more noble than ferrocene.

32. The method according to claim 29, wherein (a), (b) and (c) are dispersed in the aqueous phase by supersonic waves, a homogenizer, or a stirrer.

33. The method according to claim 32, wherein the salt is lithium sulfate.

34. The method according to claim 33, wherein the electrolyzing is conducted to a temperature of the aqueous phase of 20° to 30° C., a voltage of 0.1 to 0.5 V and a current density of 50 to 300 µA/cm².

35. The method according to claim 29, wherein the film formed on the electrode surface comprises particles 600 to 900 Å in size.

36. The method according to claim 29, further comprising controlling a thickness of the film by controlling current density during electrolyzing.

37. The method according to claim 29, wherein the ferrocene derivative is of the formula:

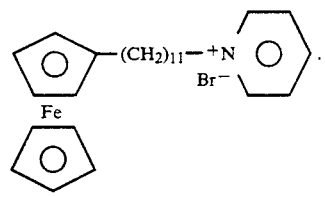

38. The method according to claim 29, wherein the ferrocene derivative is of the formula:

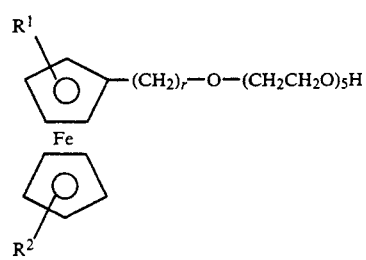

wherein s is a real number from 2 to 50 and r is 11 to 15.

39. The method according to claim 38, wherein the ferrocene derivative is of the formula:

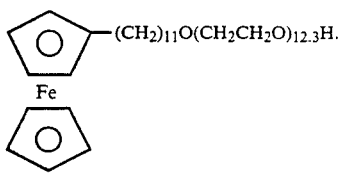

40. The method according to claim 29, wherein the ferrocene derivative is of the formula:

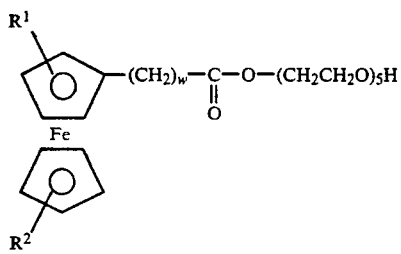

wherein s is a real number from 2 to 50 and w is 7 to 15.

41. The method according to claim 40, wherein the ferrocene derivative is of a formula selected from the group consisting of

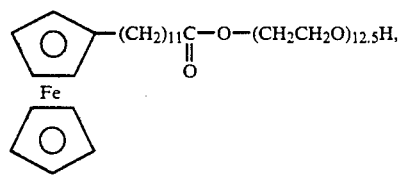

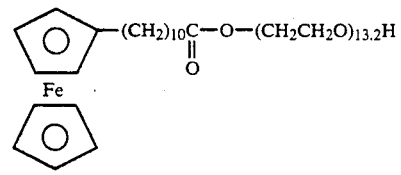

and

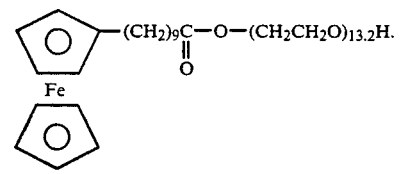

42. The method according to claim 29, wherein the ferrocene derivative is of a formula selected from the group consisting of

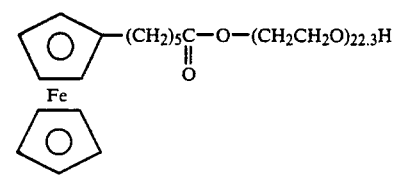

and

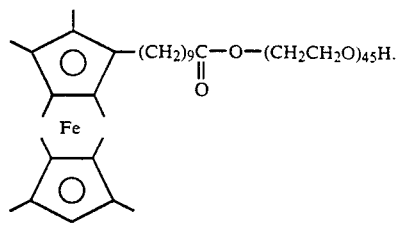

43. The method according to claim 29, wherein the hydrophobic substance is selected from the group consisting of phthalocyanine and 1-phenylazo-2-naphthol.

44. The method according to claim 29, wherein the hydrophobic substance is a phthalocyanine complex of a metal selected from the group consisting of iron, zinc, copper and cobalt.

45. The method according to claim 29, wherein the salt is at least one of a sulfuric acid salt of lithium, potassium, sodium, rubidium, or aluminum or an acetic acid salt of lithium, potassium, sodium, rubidium, aluminum, beryllium, magnesium, strontium or barium and wherein the amount of salt is 10 to 300 times the amount of the ferrocene derivative.

46. The method according to claim 45, wherein the amount of salt is 50 to 200 times the amount of the ferrocene derivative and wherein the salt is lithium sulfate or lithium bromide.

47. A method of improving the solubility of a hydrophobic substance comprising:

forming an aqueous phase of (a) the hydrophobic substance, and (b) a ferrocene derivative represented by the general formula:

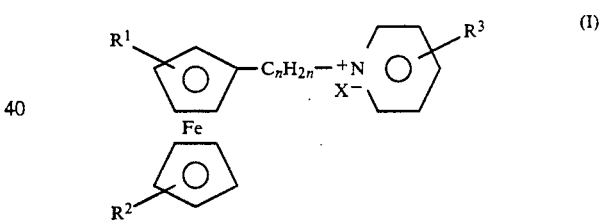

wherein $R^1$ and $R^2$ are each independently a hydrogen, a methyl group an ethyl group, a methoxy group or a carbomethoxy group, $R^3$ is a hydrogen, a methyl group, an ethyl group, a methoxy group, a carbomethoxy group, a hydroxyl group, carboxyl group or a sulfonic acid group, X is a halogen, and $C_nH_{2n}$ is a straight or branched hydrocarbon group having 4 to 16 carbon atoms; or the general formula:

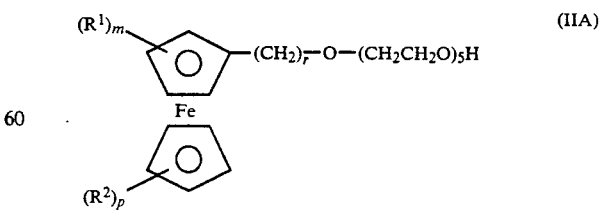

wherein m is an integer of 1 to 4, p is an integer of 1 to 5, r is an integer of 11 to 18, s is a real number of 2.0 to 70, and $R^1$ and $R^2$ are the same as described above; or the general formula:

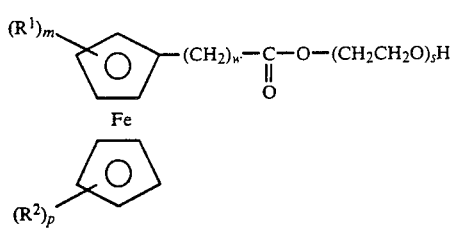
(IIB)

wherein w is an integer of 2 to 18, and m, p, s, $R^1$ and $R^2$ are the same as described above; or the general formula:

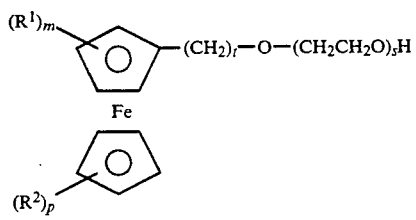

wherein t is an integer of 2 to 10, and $R^1$, $R^2$, m, p and s are the same as above; and dispersing (a) and (b) in the aqueous phase.

48. The method according to claim 47, wherein the dispersing is by means of supersonic waves, a homogenizer, or a stirrer, wherein the aqueous phase comprises a salt and wherein the aqueous phase is at a temperature of 0° to 70° C.

49. The method according to claim 48, wherein the salt is at least one of a sulfuric acid salt of lithium, potassium, sodium, rubidium, or aluminum or an acetic acid of lithium, potassium, sodium, rubidium, aluminum, beryllium, magnesium, strontium or barium and wherein the amount of salt is 10 to 300 times the amount of the ferrocene derivative.

50. The method according to claim 48, wherein the amount of salt is 50 to 200 times the amount of the ferrocene derivative and wherein the salt is lithium sulfate or lithium bromide.

51. The method according to claim 47, wherein the ferrocene derivative is of the formula:

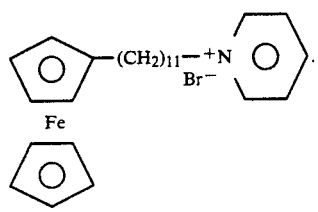

52. The method according to claim 47, wherein the ferrocene derivative is of the formula:

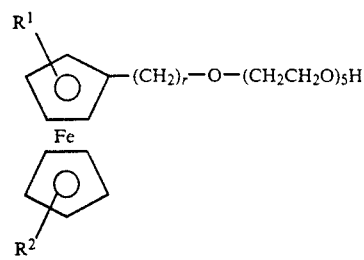

wherein s is a real number from 2 to 50 and r is 11 to 15.

53. The method according to claim 52, wherein the ferrocene derivative is of the formula:

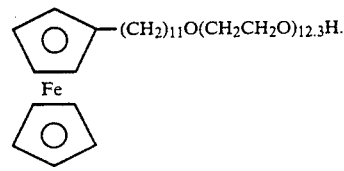

54. The method according to claim 47, wherein the ferrocene derivative is of the formula:

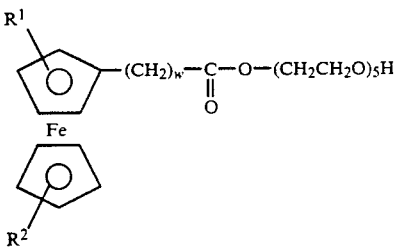

wherein s is a real number from 2 to 50 and w is 7 to 15.

55. The method according to claim 54, wherein the ferrocene derivative is of a formula selected from the group consisting of

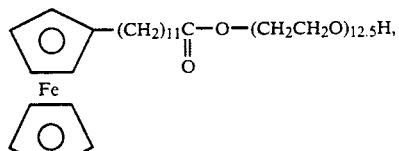

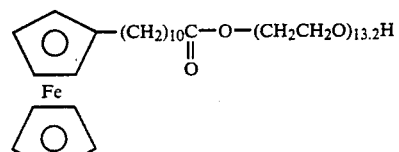

and

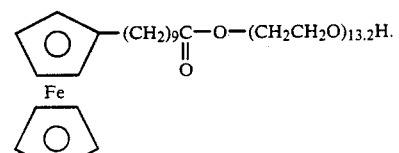

56. The method according to claim 47, wherein the ferrocene derivative is of a formula selected from the group consisting of

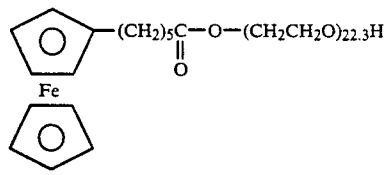

and

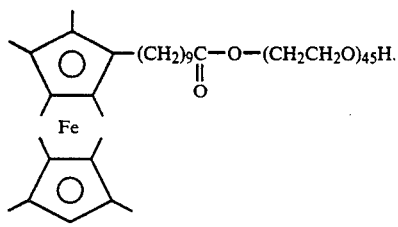

57. The method according to claim 47, wherein the hydrophobic substance is selected from the group consisting of phthalocyanine and 1-phenyhlazo-2-napthol.

58. The method according to claim 47, wherein the hydrophobic substance is a phthalocyanine complex of a metal selected from the group consisting of iron, zinc, copper, and cobalt.

59. A method of producing an organic thin film of a hydrophobic substance comprising:

forming an aqueous solution of (a) the hydrophobic substance, (b) a salt and (c) a ferrocene derivative of the general formula:

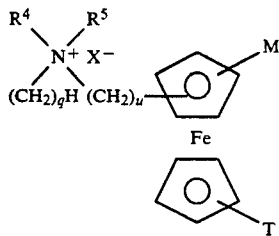

wherein $R^4$ and $R^5$ are each a hydrogen or an alkyl group having 1 to 4 carbon atoms but not exceeding q as described hereinafter, M and T are each a hydrogen or a substituent, X is a halogen, and q and u are integers satisfying the requirements: $q \geq 0$, $u \geq 0$, and $4 \leq q+u \leq 16$; the general formula:

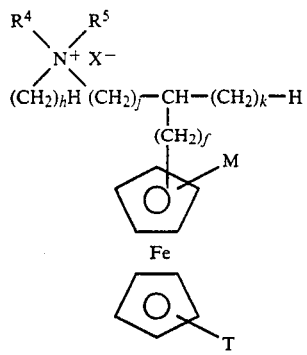

wherein $R^4$, $R^5$, X, M and T are the same as described above provided that the number of carbon atoms of $R^4$ and $R^5$ does not exceed h as described hereinafter, and f, h, j and k are integers satisfying the requirements: $h \geq 0$, $j \geq 0$, $k \geq 1$, $0 \leq f \leq k-1$ and $3 \leq h+j+k \leq 15$; the general formula:

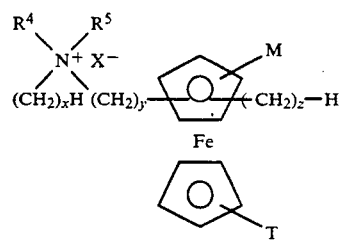

wherein $R^4$, $R^5$, X, M and T are the same as described above provided that the number of carbon atoms of $R^4$ and $R^5$ does not exceed x as described hereinafter, and x, y and z are integers satisfying the requirements: $x \geq 0$, $y \geq 0$, $z \geq 1$, and $4 \leq x+y+z \leq 16$; or the general formula:

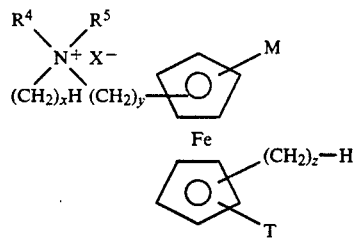

wherein $R^4$, $R^5$, M, T, x, y and z are the same as described above;

providing an electrode in contact with the aqueous phase; and electrolyzing the aqueous phase to form a thin film of the hydrophobic substance on a surface of the electrode.

60. The method according to claim 59, wherein the ferrocene derivative is of the formula selected from the group consisting of

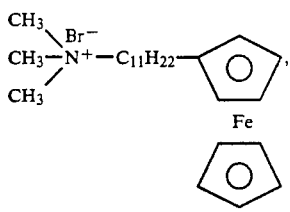

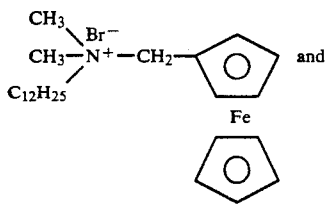 and

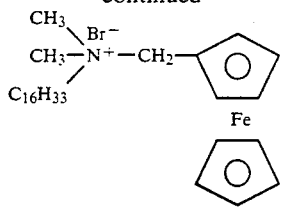

61. The method according to claim 60, wherein the salt is lithium sulfate, the hydrophobic substance is a copolymer of methacrylate and methacrylic acid and the electrode is an anode of a mixed oxide of indium oxide and tin oxide.

62. The method according to claim 60, wherein the hydrophobic substance is selected from the group consisting of poly(4-vinylpyridine), phthalocyanine and 1,1'-didodecyl-4,4'-bipyridiniumdibromide and wherein the electrode is an anode of glassy carbon or platinum.

* * * * *

UNITED STATES PATENT AND TRADEMARK OFFICE
CERTIFICATE OF CORRECTION

PATENT NO. : 5,082,539

DATED : January 21, 1992

INVENTOR(S) : SAJI et al

It is certified that error appears in the above-identified patent and that said Letters Patent is hereby corrected as shown below:

Column 34, line 13 (claim 18), delete "2", and insert --16--.

Column 34, line 21 (claim 19), delete "2", and insert --16--.

Column 34, line 55 (claim 21), delete "2" and insert --16--.

Signed and Sealed this

Twenty-seventh Day of September, 1994

Attest:

BRUCE LEHMAN

Attesting Officer

Commissioner of Patents and Trademarks